US012800571B2

(12) United States Patent
Niazi et al.

(10) Patent No.: US 12,800,571 B2
(45) Date of Patent: Nov. 17, 2026

(54) INTERFEROMETRY BASED SYSTEMS TO DETECT SMALL MASS CHANGES OF AN OBJECT IN A SOLUTION

(71) Applicant: NantBio, Inc., Culver City, CA (US)

(72) Inventors: Kayvan Niazi, Agoura Hills, CA (US); Krsto Sbutega, Redondo Beach, CA (US)

(73) Assignee: NantBio, Inc., Culver City, CA (US)

( * ) Notice: Subject to any disclaimer, the term of this patent is extended or adjusted under 35 U.S.C. 154(b) by 261 days.

(21) Appl. No.: 18/643,490

(22) Filed: Apr. 23, 2024

(65) Prior Publication Data

US 2024/0272141 A1 Aug. 15, 2024

Related U.S. Application Data

(62) Division of application No. 17/325,448, filed on May 20, 2021, now Pat. No. 12,019,067.

(60) Provisional application No. 63/028,183, filed on May 21, 2020, provisional application No. 63/028,264, filed on May 21, 2020.

(51) Int. Cl.
*G01N 33/00* (2006.01)
*G01G 9/00* (2006.01)
*G01N 33/50* (2006.01)

(52) U.S. Cl.
CPC .......... *G01N 33/5011* (2013.01); *G01G 9/00* (2013.01); *G01N 2500/10* (2013.01)

(58) Field of Classification Search
CPC ... G01N 33/5011; G01N 2500/10; G01G 9/00
See application file for complete search history.

(56) References Cited

U.S. PATENT DOCUMENTS 7,168,953 B1 1/2007 Poggio et al.
7,416,893 B2 * 8/2008 DeBernardi .......... G16H 10/40 436/64
10,314,909 B2 * 6/2019 Dransfield ....... A61K 39/39558
2009/0169051 A1 7/2009 Ioannou et al.
(Continued)

OTHER PUBLICATIONS

Non-Final Office Action from U.S. Appl. No. 17/325,448 dated Feb. 27, 2024.

*Primary Examiner* — Khai M Nguyen
(74) *Attorney, Agent, or Firm* — Harness Dickey & Pierce P.L.C.

(57) ABSTRACT

A computer-implemented method of using interferometry to detect mass changes of objects in a solution includes obtaining a time series of images using interferometry, and performing background correction on each image by classifying pixels of the image as background pixels or object pixels, fitting only the background pixels of the image to a function to generate a background fitted function, and subtracting the background fitted function from the image to generate a background corrected image. The method includes performing segmentation on the background corrected images to resolve boundaries of one or more objects, performing motion tracking on the objects to track changes in position of the objects, determining respective masses of the motion tracked objects and determining, for each image in the time series, an aggregate mass based on the respective masses to determine whether the aggregate mass of the motion tracked objects is increasing or decreasing.

20 Claims, 83 Drawing Sheets

(56) References Cited

U.S. PATENT DOCUMENTS

| | | | | |
|---|---|---|---|---|
| 2014/0178865 | A1* | 6/2014 | Reed | G01B 11/0675 435/6.1 |
| 2020/0225239 | A1* | 7/2020 | Weinstock | G01N 33/5011 |
| 2021/0278393 | A1* | 9/2021 | Reed | A61P 35/00 |
| 2021/0364496 | A1 | 11/2021 | Niazi et al. | |
| 2022/0276250 | A1 | 9/2022 | Yasuda | |
| 2024/0000842 | A1* | 1/2024 | Parks | A61P 35/00 |
| 2025/0025045 | A1* | 1/2025 | Tran | A61B 3/16 |

* cited by examiner

Bead Diameter

| | $D_{avg}$ [μm] | CV |
|---|---|---|
| **Calculated** | 10.42 | 3.2 % |
| **Actual** | 10.12 | 0.9 % |
| %Δ | 4.21 | |

Bead Mass

| | $M_{avg}$ [pg] | CV |
|---|---|---|
| **Calculated** | 549.48 | 3.22 % |
| **Actual** | 569.81 | 2.70 % |
| Δ | 3.57 % | |

FIG. 4

Phase Image

- STD = 0.33 um
- Range = 1 um

| N | Thermo | Ibidi | % Δ |
|---|---|---|---|
| 1 | 0.0350 | 0.0339 | 3.2% |
| 2 | 0.0350 | 0.0340 | 2.9% |
| 3 | 0.0350 | 0.0340 | 2.9% |
| 4 | 0.0332 | 0.0312 | 6.0% |
| Mean | 0.0345 | 0.0333 | 3.7% |
| CV | 1.9% | 3.1% | |

FIG. 9A

1. Initial Flattening: Fit entire image (background and cells) with low order polynomial (n=2 or 3) Subtracted fitted curve to image for first approximation 2. Clustering: k-means algorithm after first approximation to classify pixels as background vs foreground 3. Fit higher order polynomial (n=5) only to background pixels

| Cell Line | Bortezomib Conc [nM] | N | Normalized Growth Rate [1/h] | Δ [%] |
|---|---|---|---|---|
| H929 | 40 | 1044 | -0.01103 | -165.4 |
| H929 | 10 | 740 | 0.00297 | -82.4 |
| H929 | 2.5 | 578 | 0.01726 | 2.3 |
| H929 | 0.625 | 1586 | 0.01701 | 0.9 |
| H929 | 0.15625 | 1092 | 0.01709 | 1.4 |
| H929 | 0.039063 | 781 | 0.01776 | 5.3 |
| H929 | 0 | 500 | 0.01686 | 0.0 |
| Totals | | 6321 | | |

FIG. 22A

| Cell Line | Bortezomib Conc [nM] | N | Normalized Growth Rate [1/h] | Δ [%] |
|---|---|---|---|---|
| MM.1S | 40 | 1603 | -0.007218 | -203.0 |
| MM.1S | 10 | 1661 | -0.002845 | -140.6 |
| MM.1S | 2.5 | 1438 | 0.007555 | 7.8 |
| MM.1S | 0.625 | 1555 | 0.008715 | 24.3 |
| MM.1S | 0.15625 | 1633 | 0.007863 | 12.2 |
| MM.1S | 0.0390625 | 1479 | 0.007973 | 13.8 |
| MM.1S | 0 | 1661 | 0.007009 | 0.0 |
| Totals | | 11030 | | |

FIG. 23A

| | N | Average Mass [pg] | Normalized Growth Rate [1/h] | Δ |
|---|---|---|---|---|
| MM1S DMSO | 2078 | 107.4 | 0.01206 | 0.0 |
| MM1S DEX 200nM | 2538 | 106.8 | 0.00235 | -80.5 |
| MM1S BORT 10nM | 1192 | 106.7 | -0.00905 | -175.0 |
| MM1R DMSO | 1992 | 157.6 | 0.01136 | -5.9 |
| MM1R DEX 200nM | 2043 | 156.3 | 0.01142 | -5.3 |
| MM1R BORT 10nM | 2256 | 170.8 | -0.01220 | -201.1 |

FIG. 24C

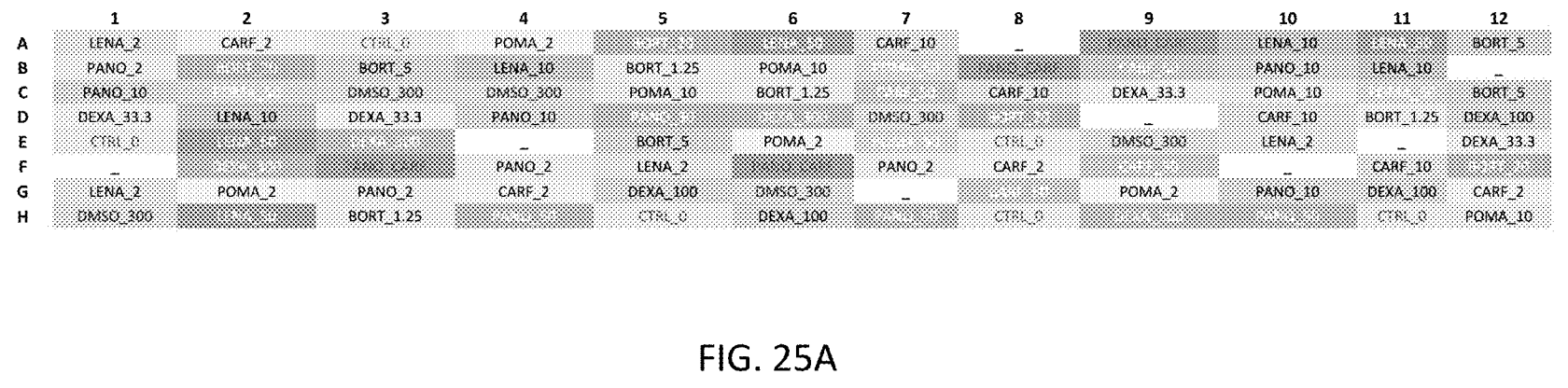

| | 1 | 2 | 3 | 4 | 5 | 6 | 7 | 8 | 9 | 10 | 11 | 12 |
|---|---|---|---|---|---|---|---|---|---|---|---|---|
| A | LENA_2 | CARF_2 | CTRL_0 | POMA_2 | [illegible] | [illegible] | CARF_10 | _ | [illegible] | LENA_10 | [illegible] | BORT_5 |
| B | PANO_2 | [illegible] | BORT_5 | LENA_10 | BORT_1.25 | POMA_10 | [illegible] | [illegible] | [illegible] | PANO_10 | LENA_10 | _ |
| C | PANO_10 | [illegible] | DMSO_300 | DMSO_300 | POMA_10 | BORT_1.25 | [illegible] | CARF_10 | DEXA_33.3 | POMA_10 | [illegible] | BORT_5 |
| D | DEXA_33.3 | LENA_10 | DEXA_33.3 | PANO_10 | [illegible] | [illegible] | DMSO_300 | [illegible] | _ | CARF_10 | BORT_1.25 | DEXA_100 |
| E | CTRL_0 | [illegible] | [illegible] | _ | BORT_5 | POMA_2 | [illegible] | CTRL_0 | DMSO_300 | LENA_2 | _ | DEXA_33.3 |
| F | _ | [illegible] | [illegible] | PANO_2 | LENA_2 | [illegible] | PANO_2 | CARF_2 | [illegible] | _ | CARF_10 | [illegible] |
| G | LENA_2 | POMA_2 | PANO_2 | CARF_2 | DEXA_100 | DMSO_300 | _ | [illegible] | POMA_2 | PANO_10 | DEXA_100 | CARF_2 |
| H | DMSO_300 | [illegible] | BORT_1.25 | [illegible] | CTRL_0 | DEXA_100 | [illegible] | CTRL_0 | [illegible] | [illegible] | CTRL_0 | POMA_10 |

FIG. 25A

| Condition | N | Average Mass | Normalized Growth Rate | Δ |
|---|---|---|---|---|
| **CTRL (no drug)** | 1011 | 123.2652008 | 0.010704564 | 0 |
| **CTRL (DMSO)** | 897 | 123.9592386 | 0.011044596 | 3.176517196 |
| **BORT 1.25nM** | 622 | 122.5395348 | 0.011162132 | 4.274518793 |
| **BORT 5nM** | 404 | 123.5473674 | -0.000575137 | -105.3728212 |
| **BORT 20nM** | 356 | 123.0741057 | -0.0098557 | -192.0700755 |
| **CARF 2nM** | 511 | 112.5854 | 0.010424307 | -2.618109786 |
| **CARF 10nM** | 445 | 128.6176799 | 0.004928343 | -53.96036123 |
| **CARF 50nM** | 380 | 118.4025343 | -0.011729049 | -209.5705444 |
| **DEX 33.3nM** | 507 | 115.9266535 | 5.84E-05 | -99.45480348 |
| **DEX 100nM** | 556 | 118.1720421 | -0.000791284 | -107.3920263 |
| **DEX 300nM** | 464 | 112.5122088 | -0.000564187 | -105.270527 |
| **LENA 2nM** | 526 | 114.9148472 | 0.010406001 | -2.789120444 |
| **LENA 10nM** | 489 | 119.1351558 | 0.010771125 | 0.621806231 |
| **LENA 50nM** | 561 | 117.6143157 | 0.009872213 | -7.77566673 |
| **PANO 2nM** | 585 | 113.9219185 | 0.003024045 | -71.74994618 |
| **PANO 10nM** | 742 | 126.3943574 | 0.003322667 | -68.96027987 |
| **PANO 50nM** | 806 | 130.2428267 | 0.003426557 | -67.98975363 |
| **PANO CARF** | 514 | 119.2946353 | 0.005458881 | -49.00416991 |
| **POMA_2nm** | 464 | 114.5715694 | 0.010083063 | -5.805939152 |
| **POMA_10nm** | 530 | 120.0230523 | 0.009619973 | -10.13203999 |
| **POMA_50nm** | 618 | 119.7971477 | 0.008807258 | -17.72426645 |

FIG. 25D

| Exp | Calc | Rel. Δ |
|---|---|---|
| 0.361 | 0.323 | 11.6% |
| 0.542 | 0.447 | 21.3% |
| 0.655 | 0.570 | 15.0% |

Image of haNK cells which have recently undergone mitosis and LCI measures of initial mass.

LCI capable of imaging without Poly-D-Lysine; results are comparable

Pluronic F68 prevents clumping of haNKs and has no discernable effect on growth rates

| | *Training Set* |
|---|---|
| **Accuracy** | 0.99 |
| **Precision** | 0.92 |
| **Recall** | 0.97 |
| **F1 Score** | 0.94 |

FIG. 35

INTERFEROMETRY BASED SYSTEMS TO DETECT SMALL MASS CHANGES OF AN OBJECT IN A SOLUTION

CROSS-REFERENCE TO RELATED APPLICATIONS

This application is a divisional of U.S. patent application Ser. No. 17/325,448, filed on May 20, 2021. This application claims the benefit of U.S. Provisional Application No. 63/028,183, filed on May 21, 2020, and the benefit of U.S. Provisional Application No. 63/028,264, filed on May 21, 2020. The entire disclosures of the above applications are incorporated herein by reference.

FIELD

The present disclosure generally relates to interferometry-based techniques for detecting small mass changes of an object in a solution using novel image processing techniques, and imaging techniques for rapidly detecting small mass changes in single cells.

BACKGROUND

Interferometry is a microscopy-based technique involving transforming a phase difference in light (e.g., occurring from changes in the speed of light from traveling through different media) into an intensity difference. Interferometry, which includes phase contrast and differential interference contrast (DIC) microscopy, may be applied to objects, e.g., living cells, or other systems that may change mass as a function of time and are observable using microscopy. Traditionally, quantitative interferometry may involve measuring phase differences from light passed through a grating, and evaluating the resulting patterns, e.g., using Fourier transforms and inverse Fourier transforms, etc., to determine phase differences.

Live cell interferometry (LCI) may be performed on living cells by quantifying the phase change of light in living cells. In some aspects, based on the index of refraction, the dry mass of an object (e.g., a cell) can be determined. However, the resolution of such techniques is limited by various artifacts, including background noise from media and plates, from the optical system, as well as computational limitations from image processing techniques to determine mass changes. Thus, there is a need for improved techniques to rapidly detect mass changes in objects that are observable by microscopic techniques such as interferometry.

Traditional approaches for the treatment of cancer include chemotherapy, radiation therapy, and surgery. More recently, immunotherapy has emerged as a therapeutic option, wherein the patient's own immune system is directed to detect and destroy cancer cells, for example, using Natural Killer (NK) cells, chimeric T cells, monoclonal antibodies, etc. Other approaches to the treatment of cancer include reactivating the immune system or enhancing the immune system through the use of checkpoint inhibitors, chemokines, or other regulatory molecules.

In 2015, more than half of cancer clinical trials included immunotherapy. However, even with these recent advances, many of the clinical trials utilizing immunotherapy have only shown about a 20% complete and durable remission (see, e.g., Gorman, C., Scientific American, (Oct. 1, 2015)). Cancer cells from different individuals may have different mutations, and may respond differently to particular therapeutics. For example, a lung cancer isolated from a particular individual may respond well to gemcitabine, while a lung cancer isolated from a different individual may respond well to methotrexate and be resistant to gemcitabine. Additionally, distinguishing whether a particular therapeutic is capable of treating the entire population of cancer cells is difficult. For example, while a particular therapeutic may rapidly eliminate a subpopulation of cancer cells, this therapeutic may not be effective on other subpopulations of cancer cells, allowing a more resistant type of cancer to repopulate and spread, which may be ultimately more difficult to treat.

Traditional assays for assessing the effectiveness of a particular drug on a particular type of cancer in order to determine an optimal therapeutic are time consuming, requiring days and even weeks to assess the effectiveness of a therapeutic. These techniques are often impractical, as lengthy delays in treatment may result in progression of the disease and/or mortality of the patient.

While a variety of cancer treatments exist, there is still a need for improved techniques to identify optimal therapeutic(s) to treat a specific patient, in order to improve treatment outcomes with regard to decreasing remission and resistance while improving efficacy.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

Some example systems and methods provided herein are directed to various image processing techniques to detect small or minute changes in the mass of an object in a solution. In some cases, the object may be a cell or a population of cells. Interferometry (quantitative phase contrast, DIC, etc.) may be used to back calculate phase delay in light from the passage of light through the object.

In some embodiments, novel image processing techniques are applied to detect small changes in individual object masses for a population of objects as a function of time.

In some aspects, an image or a portion of an image, may undergo an initial flattening process, in which the image or portion thereof is fit to a first function to generate an initial fitted function. In some aspects, the first function may be a polynomial. The initial fitted function may be subtracted from the image, or a portion thereof, to generate a first approximation of a background subtracted image or a portion thereof.

In order to separate the background regions from the object regions, a clustering technique based on a k-means algorithm may be used to classify pixels of the image or portion thereof as background pixels or object pixels. After classification, the object pixels are excluded, and only the background pixels are fit to a second function to generate a background fitted function. In some aspects, the second function is a higher order polynomial than the first function. The background fitted function is used to remove background noise from the image or portion thereof, leaving the intensity values for the objects.

In general, regarding background correction, a function (e.g., a first function, a second function, etc.) may be fit to the entire image, or a portion of the image (e.g., a region/area of the image, or a profile of the image such as a single row of pixels). For example, the background may be non-uniform along sides of the image, and therefore, it may be desirable to use different functions in different portions of the image to account for such non-uniformity. Thus, the present techniques are not to be limited and may be applied to any area of the image (e.g., a single row of pixels, regions of pixels, or the entire image).

In some aspects, the image processing techniques track movement of an object as a function of time, and based on this information, compute a corresponding object mass as a function of time. In other aspects, the image processing techniques track individual movements of a population of objects as a function of time, and compute corresponding object masses for the individual objects within the population as a function of time.

In some aspects, the object does not comprise a fluorophore. In another aspect, the object comprises one type of fluorophore. In still another aspect, the object comprises two different types of fluorophores. In still another aspect, the object comprises three different types of fluorophores. In still another aspect, the object comprises four or more different types of fluorophores.

In some aspects, the objects may be distributed over an area (e.g., on a surface of a plate, on a slide, etc.), such that motorized or robotic components of a microscope are used to change the position of the plate (e.g., by moving the microscope stage, moving a slide, etc.) or may change the position of the microscope, so that the entire area (or nearly the entire area) may be imaged as a function of time. Thus, in some embodiments, the system may be configured to scan the area using a predefined trajectory, with images taken at particular positions along the predefined trajectory. In further aspects, this process may be repeated to generate sequences of images over the entire area (or nearly the entire area) as a function of time at particular positions along the predefined trajectory.

In some aspects, the image processing techniques utilize autofocus techniques to determine optimal focus in an automated manner. Once optimal focus has been attained, images may be taken at particular positions along a predefined trajectory.

In some aspects, the stage on which the objects are placed is temperature and/or atmospheric controlled. In cases in which the object is a cell, the temperature and/or atmosphere conditions may be optimized relative to the specific cell type.

In other aspects, machine learning may be used as part of the LCI techniques provided herein. In particular, machine learning may be used for various aspects of image analysis (e.g., classifying pixels in images as background or object pixels during the process of background correction) improving separation of multiple cells (e.g., during segmentation) improving function fits as part of the process of background correction, as well as automatically identifying good object tracks and bad object tracks (e.g., tracks of moving cells) to improve the quality of object mass determination as a function of time.

In other aspects, mass changes for a population of objects exposed to a condition, which decreases, increases, or has no effect on the mass of the object, may be determined and compared to a control state absent the condition for the population of objects. For example, cell mass changes may be compared for control and non-control conditions. When mass changes between the control cells and the non-control cells are statistically distinct, a notification may be provided to the user of the system. In some cases, the notification may include the minimum time at which a statistical difference may be detected for control and non-control conditions.

Some example techniques and devices provided herein are directed to various methods of applying software based techniques to detect small changes in the volume of single cells across a population of cells.

In some embodiments, novel imaging techniques and systems are used to detect small changes in individual cell masses across a population of cells. In some embodiments, the cells may be cancer cells. In other embodiments, the cancer cells may be divided into subpopulations, each subpopulation exposed to one or more therapeutics for treatment of the cancer. In some aspects, the therapeutic may include a chemotherapeutic, an immunotherapeutic, a checkpoint inhibitor, a NK cell, a chimeric T cell, a cytokine, a chemokine, etc. or a combination thereof.

In other embodiments, the cells may be normal cells, and the imaging techniques may be used to assess growth under various media conditions. In still other cases, the cells may be immune cells undergoing activation via CD3/CD28 receptors, and the imaging techniques may be used to assess activation under various conditions.

The present techniques may also be used to assess tumor cell heterogeneity and immune cell response heterogeneity. For example, tumor cells may have subpopulations of cells, with a first subpopulation of cells responding well to a therapeutic and a second population of cells responding poorly to the same therapeutic. Some example techniques presented herein may be used to identify various subpopulations, and to identify optimal therapeutics or combinations of therapeutics for treatment of multiple subpopulations of cancer cells. Similarly, immune cells may have subpopulations of cells, with a first subpopulation of cells responding well to a ligand for activation and a second population of cells responding poorly to the same ligand. Some techniques presented herein may be used to identify various subpopulations, and to identify optimal ligands or combinations thereof for activation of immune cells.

In some aspects, example techniques provided herein may be used for the treatment of cancer in an individual in need thereof. Methods of selecting optimal therapeutics for treatment (e.g., for reducing the size of, for inhibiting the growth of, or for inhibiting the metastasis of cancer and/or tumor cells) are provided herein. Optimal combinations of compositions may be administered to a patient in need thereof in an effective amount to reduce the size of, inhibit the growth of, and/or inhibit the metastasis of cancer and/or tumor cells.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 4 shows experimental results of determination of volume and mass changes using interferometry based systems (including percent error), according to embodiments of the present disclosure.

FIGS. 9A-9B show optimization of environmental conditions using interferometry based systems, according to embodiments of the present disclosure.

FIGS. 22A, 22B, 22C and 22D show growth of H929 cells with or without bortezomib in a 96 well plate, according to aspects of the present disclosure.

FIGS. 23A, 23B, 23C and 23D show growth of MM.1S H929 cells with or without bortezomib, according to aspects of the present disclosure.

FIGS. 24A, 24B, 24C and 24D show growth of MM.1S and MM.1R cells with bortezomib or dexamethasone, according to aspects of the present disclosure.

FIGS. 25A, 25B, 25C and 25D show growth for cells incubated with various therapeutics, according to aspects of the present disclosure.

FIG. 35 is a table illustrating example results of using a machine learning model for background identification and removal.

In the drawings, reference numbers may be reused to identify similar and/or identical elements.

DETAILED DESCRIPTION

Techniques are provided herein to utilize interferometry (including LCI) to detect minute/small changes in object mass (e.g., cell mass) in a small amount of time. The LCI system may include a computer/server or other computer-based processing device, a microscopy system, as well as a structure to contain objects undergoing imaging.

In an embodiment, novel image processing techniques may be applied to detect small changes in individual object masses, and may be applied to a population of objects. Data processing techniques involving novel background correction techniques, automated autofocusing, cellular segmentation, and probabilistic models for movement as a function of time may be utilized to obtain mass changes of an object in solution as a function of time (from a time series of interferometry based images). The time series may be analyzed to determine volume changes and corresponding changes in mass. Example techniques for determining object features using volumetric descriptors are described in U.S. Published Application No. 2019/0294918, titled "Volumetric descriptors," which published on Sep. 26, 2019 and is incorporated herein by reference. The time series may be compared to another time series representing a control condition for the same type(s) of object(s), and evaluated to determine whether differences in mass between the two populations of objects (control and non-control) are statistically significant.

The systems and techniques presented herein allow for statistically significant changes to be detected in a population of objects within hours, which is a substantial improvement over prior techniques. In some cases, a statistically significant difference may be detected in as little as three hours, four hours, five hours, six hours, seven hours, etc., instead of days or weeks as in other systems. Additionally, the present techniques and systems provide for high-throughput screening of a population of objects to detect small mass changes as a function of time. The present techniques allow for potentially thousands of individual objects to be analyzed in a small time period, thereby consuming fewer computing resources than other techniques that need longer time periods to obtain significant results.

By combining various features, including cell movement tracking, background correction, interferometry, autofocusing, and segmentation, the present techniques facilitate high throughput screening of a large number of objects (e.g., cells) in a short period of time. Traditional techniques for determining cell mass changes are typically performed over longer periods of time (e.g., days or weeks instead of hours), and typically involve fewer trajectories under limited conditions. Longer incubation times may lead to results that are no longer reflective of the system being studied, as cells may adapt to different conditions, thereby, confounding analysis results.

Figure 1:
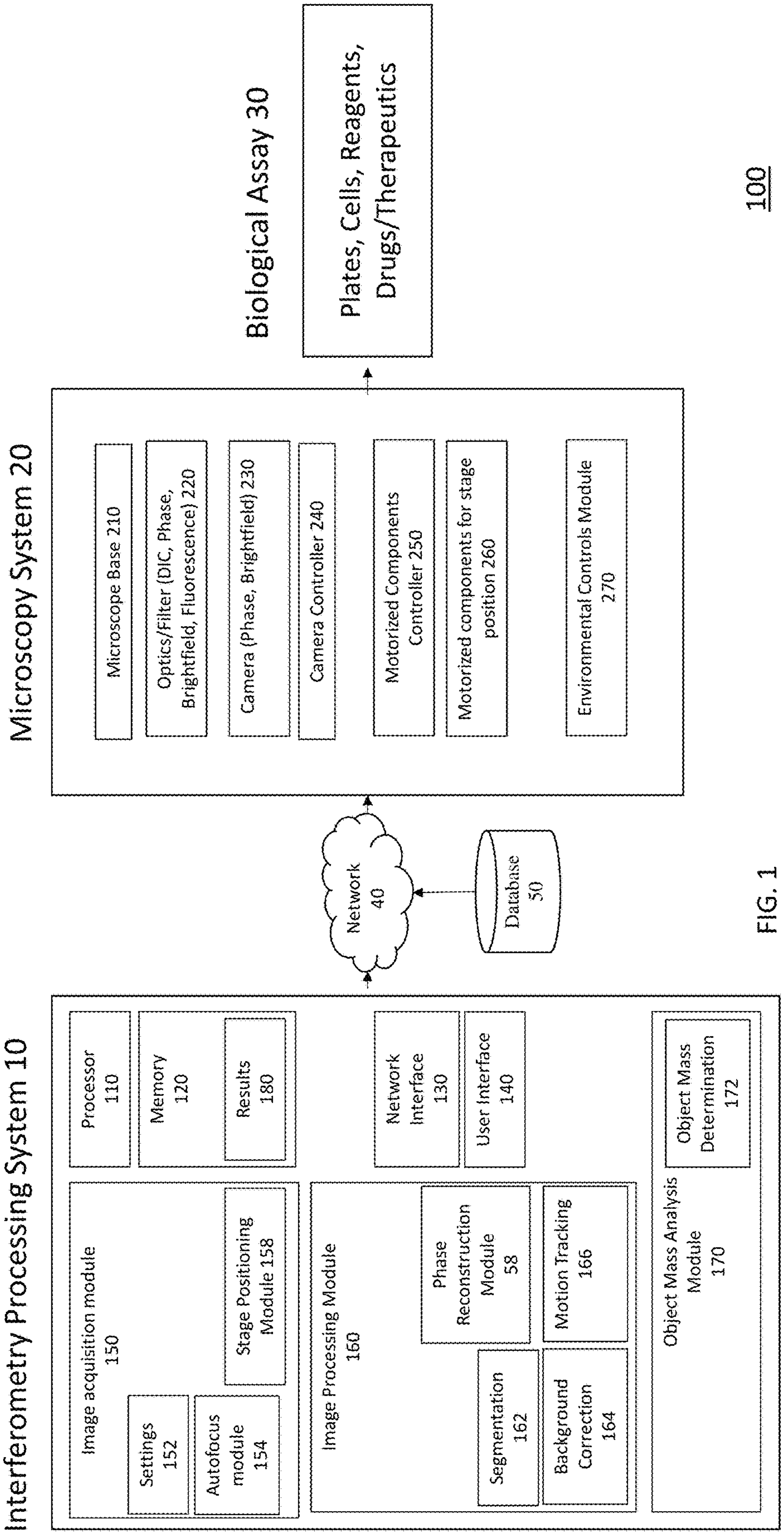
FIG. 1 is a block diagram of an example computing environment for interferometry-based mass determination in accordance with embodiments of the present disclosure.

An example LCI system 100 for interferometry based systems is illustrated in FIG. 1. The LCI system 100 includes interferometry processing system 10, microscopy system 20, and biological assay 30. In some embodiments, interferometry processing system 10 and microscopy system 20 may be remote from each other and may communicate over network 40. The network may include a wide area network (WAN), Internet, etc. In other aspects, the interferometry processing system 10 and the microscopy system 20 may be local to each other, and network 40 may comprise a local area network (LAN), Intranet, a wireless link, etc. In still other cases, interferometry processing system 10 and microscopy system 20 may be connected via a hardwire connection or any other suitable connection.

LCI system 100 enables a user to analyze mass changes in objects in a small period of time using novel data processing techniques. Interferometry processing system 10 may comprise a single stand-alone computer or may be a server system accessible through a client system. Further, processing system 10 can comprise a suite of software executing on processors working alone or collectively. Interferometry processing system 10 may comprise a variety of modules including image acquisition module 150 (e.g., one or more sensors, etc.), image processing module 160, and object mass analysis model 170. Additionally, interferometry processing system 10 may comprise processor 110, memory 120, network interface 130, and user interface 140 as described below. Image acquisition module 150 may govern parameters and processes associated with collection of images. The acquired images can be interferometry-based (e.g., DIC, phase contrast, etc.), may include fluorescent images of labeled objects, or any other suitable type of image. The phase difference between light entering the object and light exiting the object can be used to determine the index of refraction of the object. This may be determined on a per pixel level to obtain a per pixel index of refraction for the object. Based on this intensity, the phase may be back-calculated.

Image acquisition module 150 may comprise settings 152, autofocus module 154, and stage positioning module 158. Settings 152 may comprise various settings for microscopy system 20, and may include the type of imaging to be performed (e.g., DIC, phase contrast, florescence, etc.). Settings 152 may also include parameters for selection of a particular optical lens (10×, 20×, 40×, etc.), filter(s) for the type of imaging selected, the length of time of image acquisition, the time interval at which images are collected, trajectories, and any other settings needed to configure microscopy system 20 for collection of images. Autofocus module 154 and stage positioning module 158 automate focusing in an optimal manner so that image acquisition can be performed automatically across a designated area (e.g., a 12, 24, 36, 96, etc. well plate). This feature allows automated collection of images along specific positions of a trajectory, in which a position along the trajectory applies autofocusing techniques prior to image collection for that position. By automatically determining the optimal focus for image collection at specific positions along the trajectory, the system may repeat image collection along the trajectory to generate a time series at each position. Autofocus module 154 may include any suitable algorithm to assess focus.

Stage positioning module 158 may communicate with motorized components controller 250 to control stage position. Module 250 may execute commands to generate an output provided to motorized components 260 to horizontally and vertically control stage positioning (e.g., movement of the stage on which the objects are placed, incrementally over a vertical distance and/or horizontally over a trajectory). The autofocus module 154 may interface with camera controller 240 and motorized components controller 250, in microscopy system 20 to coordinate image acquisition.

The autofocus module 154 determines the vertical position of the microscope stage for optimal focus, based on the microscope objective height that maximizes or minimizes a measure of focus. Techniques to measure the focus for phase images were developed for the present system. These autofocus techniques include: (1) acquiring an image and calculating a focus score; (2) using a minimization technique to determine the next vertical position that provides a better focus score; and (3) exiting/ending the minimization technique when the vertical position does not change on subsequent minimization operations. Accurate autofocus is needed to obtain optimal results, as focus drift can introduce error into the results.

The minimization technique may use a derivative-free minimization algorithm (e.g., included in a software package such as MATLAB, etc.) and/or may use standard functions for minimizing objective functions over a bounded interval. In some embodiments, the autofocus module may utilize a Gaussian derivative (GDER) to generate a focus measure for interferograms generated with the present system. In some aspects, the focus position is defined as a position at which the GDER is at a minimum (with the least contrast).

In some embodiments, automated autofocus techniques may include: (1) obtaining two to three images or more; (2) generating a GDER; (3) extrapolating a new minimum; (4) evaluating the GDER at the new minimum; and (5) repeating this process until a change in the GDER (or z position) is below a specified tolerance.

Image processing module 160 governs analysis of the images acquired by image acquisition module 150. Module 160 analyzes trajectories of individual cells or objects as a function of time, applies background correction techniques to improve accuracy of mass calculations, and performs segmentation. Each of these functions are discussed in additional detail as follows.

Image processing model 160 may comprise segmentation module 162, background correction module 164, motion tracking module 166, and phase reconstruction module 58. Each of these modules operates on images that have been collected by image acquisition model 150. Segmentation module 162 identifies individual objects, both alone and in physical contact with other objects (e.g., clusters of cells which are adhered or proximal to each other). Background correction model 164 may use a multistep fitted polynomial approach to subtract background noise from the images or a portion thereof, which increases computational accuracy for computing mass changes. In some aspects, background correction may include an initial fitting step and a secondary more precise fitting step only on the background portion (and not the object portion). Motion tracking module 166 utilizes algorithms to track objects as a function of time. To determine mass changes, the objects are typically monitored over a period of time, and therefore, motion tracking accounts for objects that change positions as a function of time, thereby allowing the same object to be referenced in a time series so as to avoid object mix ups. For example, masses of cells may be significantly conserved over time even as cell morphology may change. Therefore, mass can be used to track movement of cells as a function of time, even if cell morphology changes for the cells over time (which would make it difficult to track cells over time based on shape alone, etc.). Phase reconstruction module 58 may overlay acquired images (e.g., obtained with light of different polarizations (such as 0° and 90°)), to generate interferometry-based images. The image processing module 160 may utilize any suitable commercial (e.g., MATLAB, OpenCV, Python, etc.), custom image analysis software, or any combination thereof to perform image processing functions.

Object mass analysis module 170 involves determination of object mass for individual objects and/or populations of objects and may comprise object mass determination module 172. For cells, the object mass determination module 172 may integrate the index of refraction over the cell to determine the mass of the cell. Since this technique relies on changes in the index of refraction, this technique is insensitive to changes in water volume. In some cases the cell mass change may be determined for individual cells and in other cases, the cell mass change may be determined in aggregate for a population of cells.

Microscopy system 20 may comprise microscopy base 210, optics and filters 220, camera 230, camera controller 240, motorized components controller 250, motorized components for stage position 260, and environmental controls module 270. Microscope base 210 includes core components of the microscope, including the stage, objective holders, camera mount interfaces, manual focusing controls, as well as other standard components of a microscope. Optics and filter module 220 includes various filters and optical lenses to collect the various types of images described herein, including DIC, phase contrast, bright field and fluorescent images.

Camera 230, or other sensor, may be connected to the frame of microscope base 210 as well as to system 10 via network 40. The camera may be provided settings from settings 152 pertaining to image acquisition, and may send acquired images to system 10 for analysis. Camera controller 240 may control operations of the camera. Motorized or robotic components controller 250 may control the X, Y, and Z positioning of the microscope stage relative to the lens, and therefore, may also be involved in autofocus and trajectory functionality. Motorized components for stage position 260 move the stage in response to input from controller 250 (e.g., as part of the autofocusing process and trajectory control) to allow images to be collected across the entire area. In some aspects, the camera may employ quadiwave lateral shearing interferometry to create a phase map (e.g., quantitative phase imaging cameras by Phasics Corp.; See URL www.phasicscorp.com/application/innovative-phase-imaging-techniques/#What-is-quantitative-phase-imaging) to form the interferometry based images.

In various implementations, one or more robots may be designed, implemented, deployed, etc., to control movement of one or more of the camera 230, another sensor, the microscope base 210, the stage position 260, etc. For example, the controller 250 or camera controller 240 may control movement of one or more robotic arms, conveyors, etc. to position the camera to perform image acquisitions at various locations, to position the microscope at various locations, to move the stage position 260 to various locations for image capture, etc. The one or more robots may be tuned to optimize the speed of image capture at different locations, to provide efficient and steady movement through a sequence of positions, etc.

Environmental controls module 270 may accept inputs from interferometry processing system 10 to regulate aspects of the environment, including temperature, humidity, $CO_2$, etc. Alternatively, environmental control module 270 may have manual controls attached to its structure allowing a user to adjust temperature, $CO_2$, humidity, etc. For example, controls module 270 may include a temperature control, a $CO_2$ control, an active humidity control, etc., each of which may be attached to an enclosed chamber in which the objects are placed. In some aspects the incubation temperature may range from 35 to 37° C. In some aspects, temperature uniformity may vary less than +0.3° C. from the set value. In other aspects, the temperature stability may vary from +0.1° C. of the set value. In some aspects, the enclosed chamber may be a stage-top incubator having a control system to maintain a desired thermal temperature. To ensure a uniform and constant temperature, heaters may be embedded in the top and bottom plates of the enclosed chamber. Typical environmental conditions for mammalian cells include 37° C., 93% humidity and 5% $CO_2$ content.

Biological assay 30 includes the objects, solution that the object(s) are placed into, components on which the objects are placed, as well as chemicals (e.g., enzymes, drugs and/or therapeutics, reagents, etc.) added to the solution to create a condition different from a control condition. When the object is a cell, the component may be well plates into which the cells are placed, and drugs, therapeutics, or other molecules may be added to the solutions that the cells are placed into.

Results 180 of the mass determination may be stored in memory 120 of system 10, or externally in database 50. The database system 50 may be local to or remote from system 10 and may communicate via any appropriate communication medium (e.g., local area network (LAN), wide area network (WAN), Internet, Intranet, wireless, hardwire, etc.).

System 10 may be implemented by any conventional or other computer system and may comprise at least one hardware processor 110 (e.g., microprocessor, multi-core processor, controller, central processing unit (CPU), GPU, etc.), one or more memories 120, internal or external network interfaces or communications devices 130 (e.g., modem, network cards, serial or parallel communication, FireWire, USB, etc.), a display or monitor for displaying results, optional input devices (e.g., a keyboard, mouse or other input device), and any commercially available and/or custom software (e.g., browser/interface software, software suite, image acquisition module 150, image processing module 160, object mass analysis module 170, etc.).

In some embodiments, the results may be provided to the user via user interface 140, including a graphical user interface (e.g., GUI, etc.) or other interface (e.g., command line prompts, menu screens, etc.). System 10 may include various modules (e.g., image acquisition module 150, image processing module 160, object mass analysis module 170, etc.) that may be implemented by any combination of software and/or hardware modules or units, and may reside within memory 120 of the system 10 for execution by processor 110. For example, combining aspects of software and hardware may allow for increased technical functionality of the system 10 in terms of device control (e.g., designing a software algorithm to control movement of the image acquisition module 150 among various positions by taking into account the capabilities and/or limitations of the hardware of the image acquisition module 150), and image analysis (e.g., designing the software algorithm that focuses and processes images by taking into account the capabilities and/or limitations of the hardware of the image processing module 160 and object mass analysis module 170, etc.).

Many such configurations are possible, and all such configurations are contemplated for use herein. For example, the functions of interferometry processing system 10 may be distributed across a plurality of computing systems, and the results may be available to one or more (remote) client systems. In other aspects, the controller functionality (e.g., camera control 240, motorized components controller 250, etc.) may be software based and may reside within interferometry processing system 10.

Figure 2A:
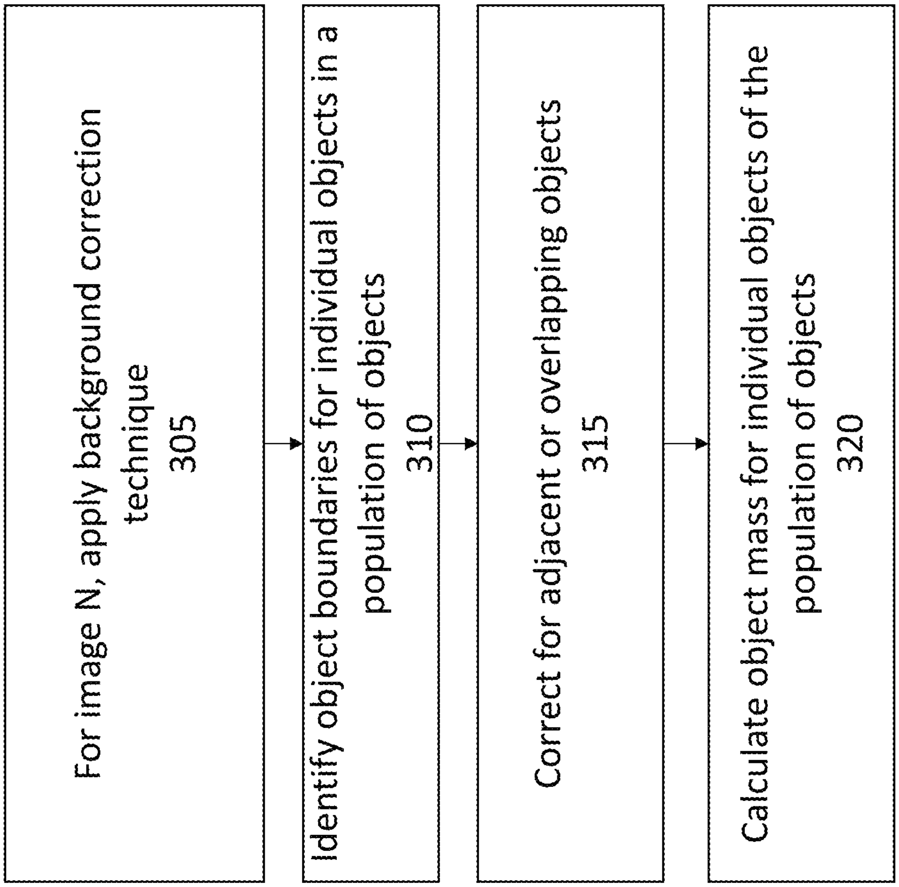
FIGS. 2A-2B are flowcharts of example operations for determining small mass changes using interferometry-based systems, according to embodiments of the present disclosure.
Figure 2B:
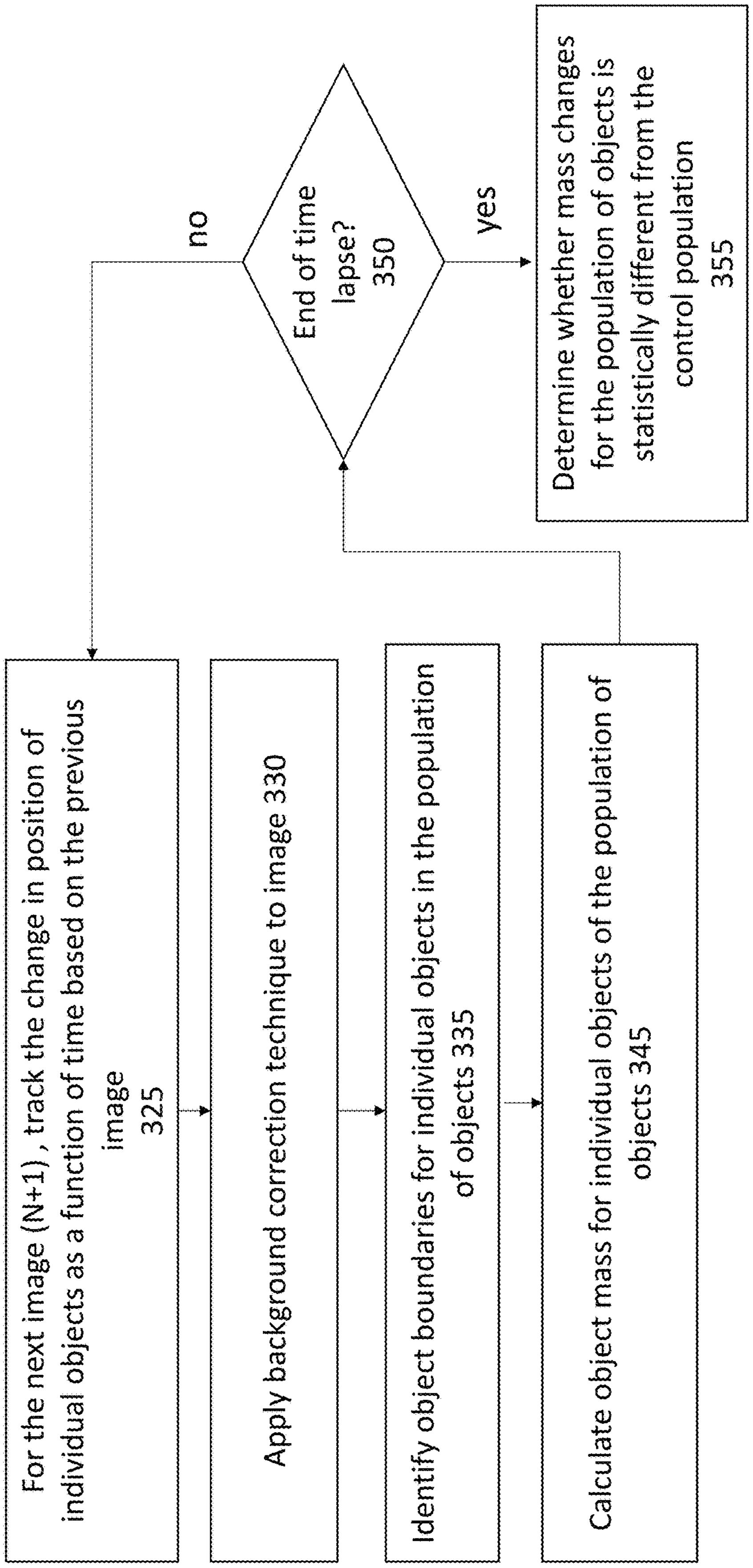

FIGS. 2A-2B are flowcharts of example operations for small mass determinations using interferometry based systems, according to embodiments of the present disclosure. These operations may be applied to each image of a time series of images at particular locations along a trajectory.

For the first image in a time series, the following operations may be performed. At operation 305, a background correction technique is applied to the image. At operation 310, object boundaries are identified for individual objects among a population of objects. At operation 315, adjacent or overlapping objects are identified using segmentation techniques. At operation 320, object mass is calculated for individual objects of the population of objects.

For subsequent images in a time series, the following operations 325-355 may be performed. At operation 325, for the next image (N+1) in the time series, the change in position of individual objects is tracked as a function of time relative to the previous image. At operation 330, a background correction technique is applied to the (N+1) image of the time series of images.

At operation 335, object boundaries of individual objects are identified for the population of objects. For example, segmentation techniques maybe used to identify boundaries of overlapping or adjacent objects, in order to correct for adjacent or overlapping objects. For example, mass changes of two adjacent cells should be determined for each cell, and the adjacent cells should not be treated as a single cell, as this may skew mass determinations. At operation 345, object mass is calculated for individual objects of the population of objects. At operation 350, if there are additional images in the time lapse, the system may proceed to operation 325, to analyze the next image in the time series. If the last image in the time series has been analyzed, the system may proceed to operation 355 to calculate mass changes for the population of objects. For example, individual mass changes may be combined to generate an aggregate mass change for the population of objects. The aggregate mass for the population of objects may be compared to the aggregate mass for a control population of objects to determine whether the aggregate mass of the population of objects is statistically different from the aggregate mass of the control objects.

Figure 3:
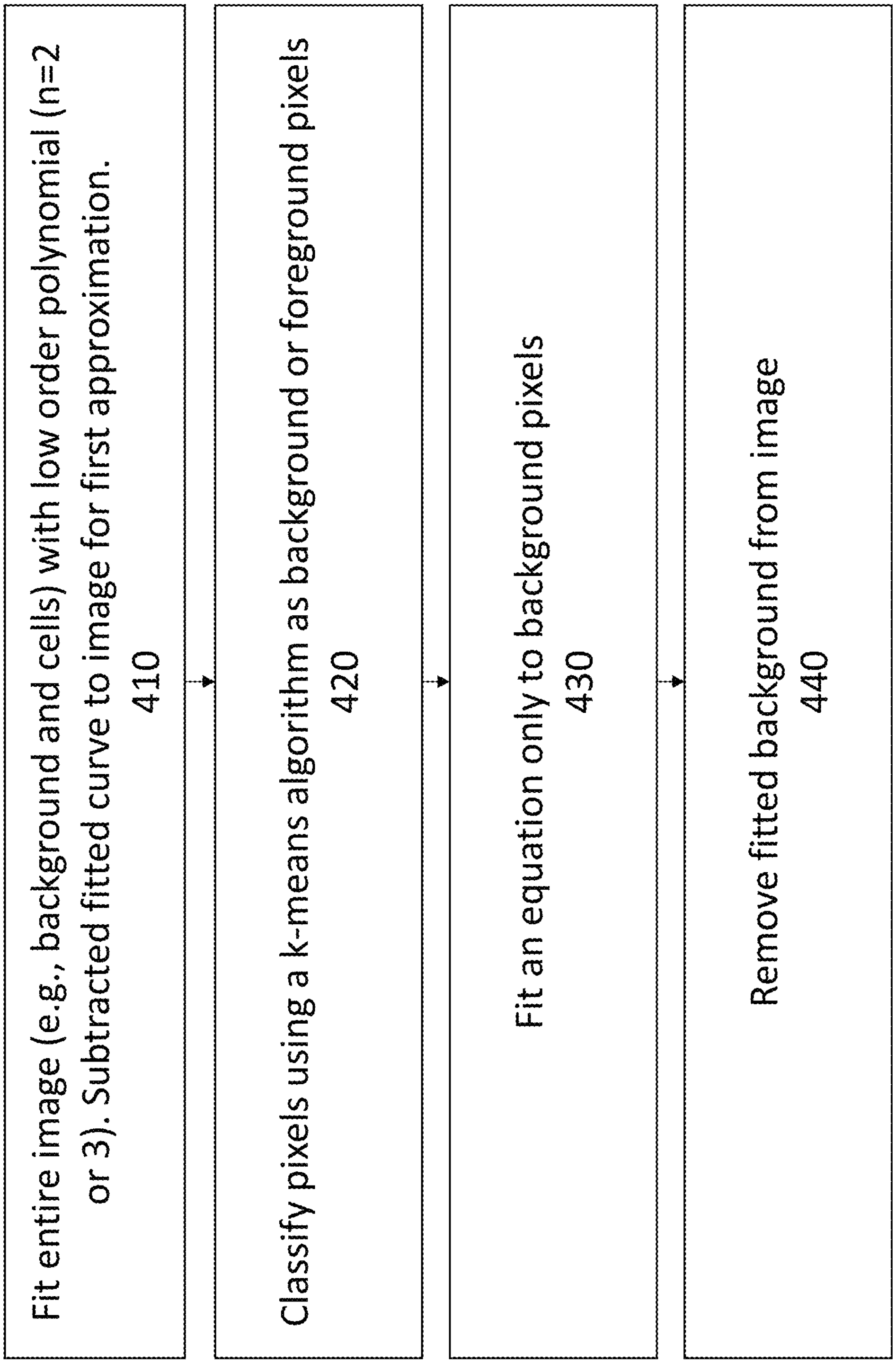
FIG. 3 is a more detailed flowchart of example operations involving background correction of images, according to embodiments of the present disclosure.

FIG. 3 is a more detailed flowchart of operations involving background correction techniques for images, according to embodiments of the present disclosure. At operation 410, the entire image or a portion thereof (e.g., including background and objects) may be fit with a low order polynomial (n=2 or 3). For example, the image or portion thereof may undergo an initial flattening process, in which the image or portion thereof is fit to a first function (e.g., an initial fitted function). In order to separate the background from the object, a clustering technique based on a k-means algorithm may be used to classify the pixels as background or non-background (e.g., object) pixels, at operation 420. At operation 430, a function may be fit only to background pixels. After classification, the non-background pixels are excluded, and only the background pixels are fit to a second function to generate a background fitted function. In some aspects, the second function may be a higher order polynomial than the first function. In this example, polynomial functions are used for fitting background intensities, however, any suitable function may be used. At operation 440, the background fitted function is subtracted from the image or portion thereof. Thus, the background fitted function is used to remove background noise from the image or portion thereof, leaving the intensity values for the objects. In some cases, the background intensity may vary over an area of an image (e.g., as a function of an x or y position of the image). Therefore, the present embodiments also cover cases in which different functions may be used to fit different areas or regions of the image (instead of using one function to fit the entire image).

Major sources of error in the LCI system 100 may include: (1) optics (light source/camera noise/table vibration); (2) environmental controls (temperature non-uniformity); (3) image analysis software (background correction); or (4) biological variations. The overall system accuracy and precision may be improved by minimizing error from these, or other, sources.

Present techniques may be applied to any application involving mass change as a function of time. For biological processes, the techniques may be used to measure increases in mass (e.g., growing cells), decreases in mass, or constant mass. For biological systems, factors that may influence cell mass include but are not limited to a type of growth media, temperature, humidity, $CO_2$ levels, growth factors or other molecules that interact with the cell to trigger growth. For biological processes involving mass changes, the present techniques may be used to quantify such changes. In various implementations, mass determinations may be used as an indicator for an amount of genomic material (e.g., a determined mass for a populations of cells in a sample may be used to determine whether a desired amount of genomic material is present in the sample, etc.).

In some aspects, well plates or any other multi-chambered device may be used to test various therapeutics or combinations thereof to determine which therapeutics or combinations thereof affect object mass as a function of time. In some aspects, a well plate with any suitable dimensions may be used, including but not limited to: a 12 well plate, a 24 well plate, a 48 well plate, a 96 well plate, etc. In some aspects, each well may contain a different therapeutic or combination of therapeutics. In other aspects, the wells may be grouped, such that each group of wells contain the same therapeutic or combination of therapeutics. In still other aspects, each well may contain a different concentration of a therapeutic. In some aspects, the concentrations may range from 0.01 nM up to 100 mM, from 0.01 nM up to 1 mM, from 0.01 nM up to 100 μM, from 0.01 nM up to 100 nM, or from 0.02 nM up to 40 nM. For example, in one aspect, concentrations may vary from, e.g., 0.04 nM, 0.15 nM, 0.62 nM, 2.5 nM, 10 nM, to 40 nM, etc., allowing a minimum effective concentration of the therapeutic to be determined. In other aspects, multiple therapeutics may be present, with each well containing a different concentration of one or more therapeutics. For example, in some aspects, a first therapeutic may be kept at a constant concentration while the concentration of a second therapeutic may be varied, or vice versa. In other aspects, the individual wells may be grouped, with each group having a different concentration of a therapeutic.

In some aspects, the well plates may be manufactured using different materials with different optical characteristics, and therefore, having different optical clarities for distortion free images. Materials may include but are not limited to: polystyrene, polyolefin acrylate, polypropylene, polyethylene, polycarbonate, etc.

Machine Learning Applications

Machine learning/artificial intelligence techniques may be used for various aspects of image analysis. As referenced herein, it is understood that the term "machine learning" refers to artificial intelligence systems configured to learn from data without being explicitly programmed. Such systems are understood to be necessarily rooted in computer technology, and in fact, cannot be implemented or even exist in the absence of computing technology. While machine learning systems may utilize various types of statistical analyses, machine learning systems are distinguished from statistical analyses by virtue of their ability to learn from digital data without explicit programming and such systems are reliant upon computing technology through execution of software implementations of one or more machine learning algorithms on one or more processors.

Figure 34:
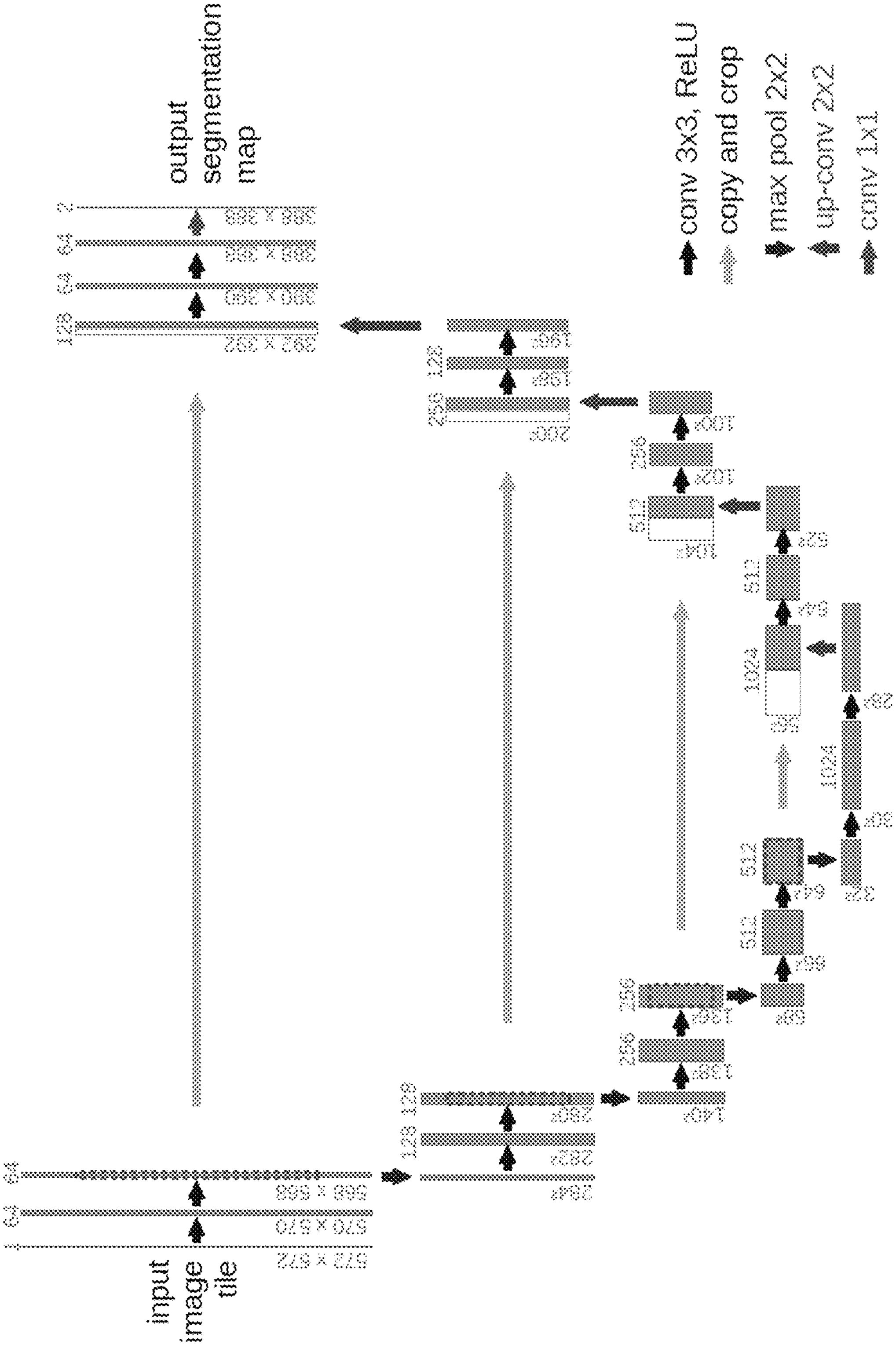
FIG. 34 is an illustration of an example machine learning network architecture that may be used for background versus foreground classification.

Classification of background pixels versus non-background pixels may account for up to 75% of overall error. Accordingly, machine learning techniques may be used to classify background pixels from non-background pixels, e.g., to minimize classification error in interferometry-based images. An example machine learning network architecture for classifying background pixels is illustrated in FIG. 34, which may include any suitable elements such as input image tiles, output segmentation maps, one or more convolution layers, up-conversion layers, ReLU blocks, pool operations, etc. In various implementations, a training data set may be provided in which background and object pixels are identified for an image. The machine learning system may generate a classifier based on the training data, and the performance of the classifier may be evaluated based on classification of other images not included in the training data set.

Machine learning techniques may also be used to improve separation of multiple objects due to overlap or adjacency. For example, a training data set may be provided in which the boundaries of objects that are adjacent to each other are identified. The machine learning system may utilize training data to generate a trained classification model, which may be evaluated based on performance metrics of analyzing images not included in the training data set.

Machine learning may also be used to automatically identify good tracks and bad tracks, and to discard bad tracks to improve the quality of the mass determinations. For example, trajectories may be eliminated if objects appear for too short of a period of time in a time series, if the image of the object is too noisy (out of focus), or if the object appears to move too rapidly.

Machine learning techniques may also be used to improve function fits for background correction. In some aspects, fitting may be parametric, but other functions may be used to improve classification and increase accuracy of object mass determinations.

Any suitable machine learning algorithm (e.g., support vector machine, neural network, decision tree, random forest, deep learning neural network, logistic regression, etc.) may be used for classifying background pixels and object pixels, for identifying fitting functions (e.g., initial fitting function and background fitted function), identifying object boundaries, and identifying bad object tracks.

The machine learning engine may create a trained model as a function of the training data, and optionally, input(s) from the user. Once trained, the trained model will have one or more model parameters or metrics that describe the trained model (e.g., accuracy, accuracy gain, sensitivity, sensitivity gain, performance metrics, weights, learning rate, epochs, kernels, number of nodes, number of layers, etc.).

Machine learning algorithms may include different types of algorithms including implementations of a classification algorithm, a neural network algorithm, a regression algorithm, a decision tree algorithm, a clustering algorithm, a genetic algorithm, a supervised learning algorithm, a semi-supervised learning algorithm, an unsupervised learning algorithm, a deep learning algorithm, or other types of algorithms. More specifically, machine learning algorithms can include implementations of one or more of the following algorithms: a support vector machine, a decision tree, a nearest neighbor algorithm, a random forest, a ridge regression, a Lasso algorithm, a k-means clustering algorithm, a boosting algorithm, a spectral clustering algorithm, a mean shift clustering algorithm, a non-negative matrix factorization algorithm, an elastic net algorithm, a Bayesian classifier algorithm, a RANSAC algorithm, an orthogonal matching pursuit algorithm, bootstrap aggregating, temporal difference learning, backpropagation, online machine learning, Q-learning, stochastic gradient descent, least squares regression, logistic regression, ordinary least squares regression (OLSR), linear regression, stepwise regression, multivariate adaptive regression splines (MARS), locally estimated scatterplot smoothing (LOESS) ensemble methods, clustering algorithms, centroid based algorithms, principal component analysis (PCA), singular value decomposition, independent component analysis, k nearest neighbors (kNN), learning vector quantization (LVQ), self-organizing map (SOM), locally weighted learning (LWL), apriori algorithms, eclat algorithms, regularization algorithms, ridge regression, least absolute shrinkage and selection operator (LASSO), elastic net, classification and regression tree (CART), iterative dichotomiser 3 (ID3), C4.5 and C5.0, chi-squared automatic interaction detection (CHAID), decision stump, M5, conditional decision trees, least-angle regression (LARS), naive bayes, gaussian naive bayes, multinomial naive bayes, averaged one-dependence estimators (AODE), bayesian belief network (BBN), bayesian network (BN), k-medians, expectation maximisation (EM), hierarchical clustering, perceptron back-propagation, hopfield network, radial basis function network (RBFN), deep boltzmann machine (DBM), deep belief networks (DBN), convolutional neural network (CNN), stacked auto-encoders, principal component regression (PCR), partial least squares regression (PLSR), sammon mapping, multidimensional scaling (MDS), projection pursuit, linear discriminant analysis (LDA), mixture discriminant analysis (MDA), quadratic discriminant analysis (QDA), flexible discriminant analysis (FDA), bootstrapped aggregation (bagging), adaboost, stacked generalization (blending), gradient boosting machines (GBM), gradient boosted regression trees (GBRT), random forest, etc. Training may be supervised, semi-supervised, or unsupervised.

The machine learning model may be a dynamic model that is updated (e.g., periodically or on a continuous basis). In some embodiments, the trained model is updated in real-time, on a daily, weekly, bimonthly, monthly, quarterly, or annual basis. For example, as new information is made available, the learning model may be further updated. In such cases, the learning model may comprise metadata that describes the state of the learning model with respect to its updates, such as one or more of the following: a version number, date of update, amount of new data used for the update, shifts in model parameters, convergence requirements, or other information. Such information provides for managing large collections of models over time, where each learning model may be treated as a distinct manageable object.

LCI has a variety of advantages over other techniques. LCI provides label-free techniques for quantitatively and accurately tracking single object changes in mass.

Thus, any process involving a mass change as a function of time can be tracked using present techniques, provided that the mass change can be resolved with LCI. By optimizing the material of the plates for optimal clarity, the media to minimize background noise, and by using proprietary software techniques to detect changes in mass as a function of time, statistically significant differences in object (e.g., cell) mass can be detected in much shorter times as compared to traditional techniques. For example, using the techniques provided herein, statistically significant differences in object mass can be detected in as little as three, four, or five hours.

The present systems and techniques are suited for biological samples having a limited shelf life ex vivo, and for providing data to assist physicians with clinical decision processes. The single-cell, non-destructive nature of these techniques can be exploited to determine population heterogeneity. Other advantages include improved accuracy and resolution using 2D data models, instead of more complex 3D data models.

System Calibration

The following examples pertain to various applications and are intended to be non-limiting.

Techniques are provided for calibrating optical subsystems. FIG. 4 shows experimental results of determination of volume and mass using interferometry based systems along with corresponding percent error, according to embodiments of the present disclosure. For example, beads of a known diameter may be placed on a microscope slide or other suitable surface for imaging.

For example, the diameter of the bead may be measured using images of the beads, and the measured diameter may be compared to the actual known diameter to determine accuracy of the system. Similarly, the mass of the bead may be computed based on physical parameters and a known refractive index. For the present system, errors were about 3-4% (see, FIG. 4 illustrating bead diameter on the left and bead mass on the right). About 73 beads of known diameter were selected for imaging.

For calibration using live biological systems, red blood cells (RBCs) may be selected due to their uniformity and characterization. Using the present system, 2013 RBC were analyzed, and were determined to have a mean mass of 34.3 pg, which falls within the known range of 27-37 pg.

Figure 5A:
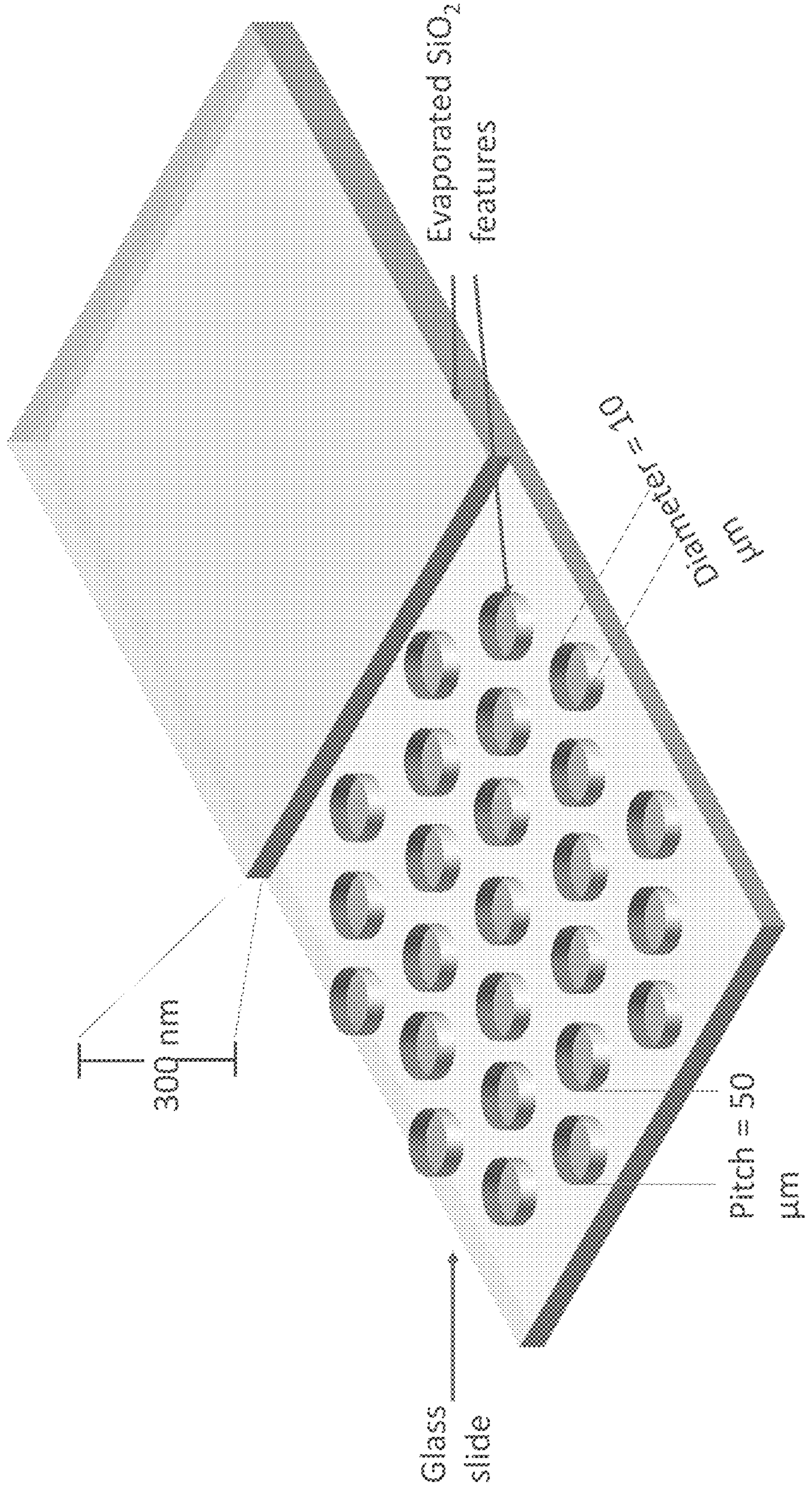
FIGS. 5A, 5B and 5C show devices and experimental results for determining error using interferometry based systems, according to embodiments of the present disclosure.

In other embodiments, a glass slide was created, with wells 10 um in diameter, and each well having a pitch of 50 μm (see, FIG. 5A). For a $\lambda$=550 nm in air: $\Delta n\times ht$=135 nm=0.242; and in water: $\Delta n\times ht$=36 nm=0.072.

Figure 5B:
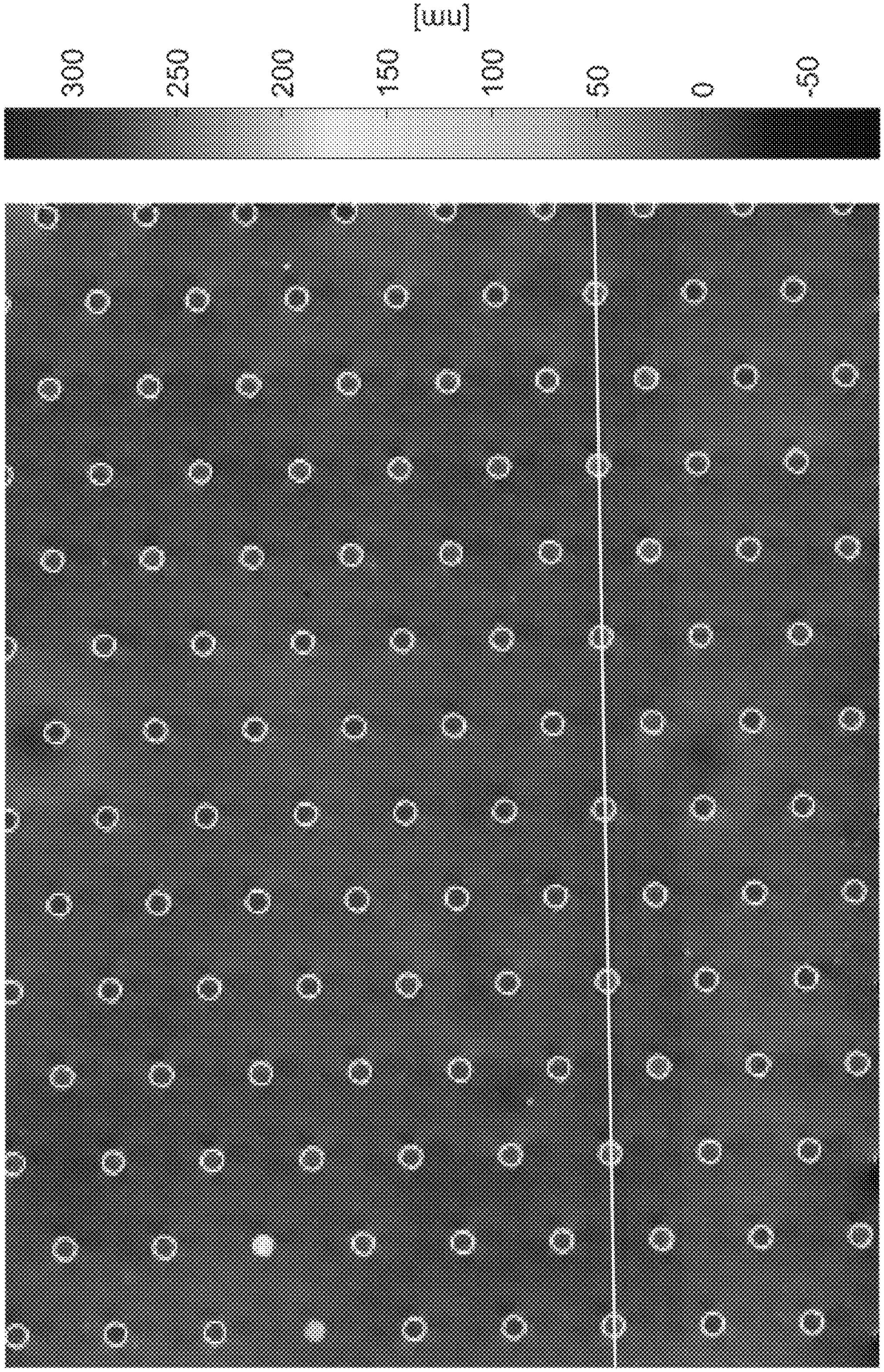
Figure 5C:
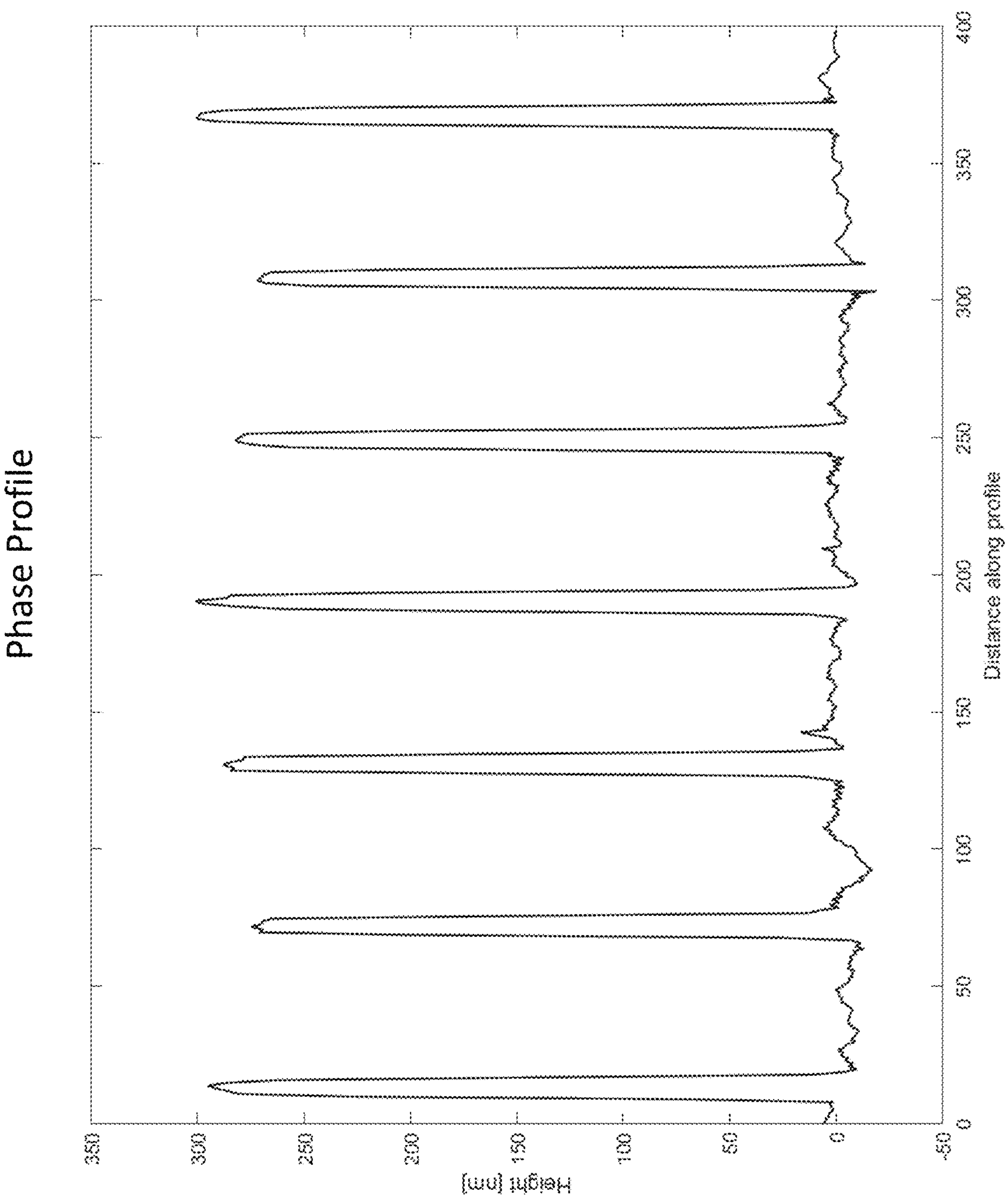

FIGS. 5B-5C show experimental images of calibration using the glass slide. A track (line) of wells was selected for imaging, and FIG. 5C shows the phase profile determined from imaging studies. Here, the computation shows well results which are regularly spaced apart at about the same height, which is consistent with the well height.

Figure 6:
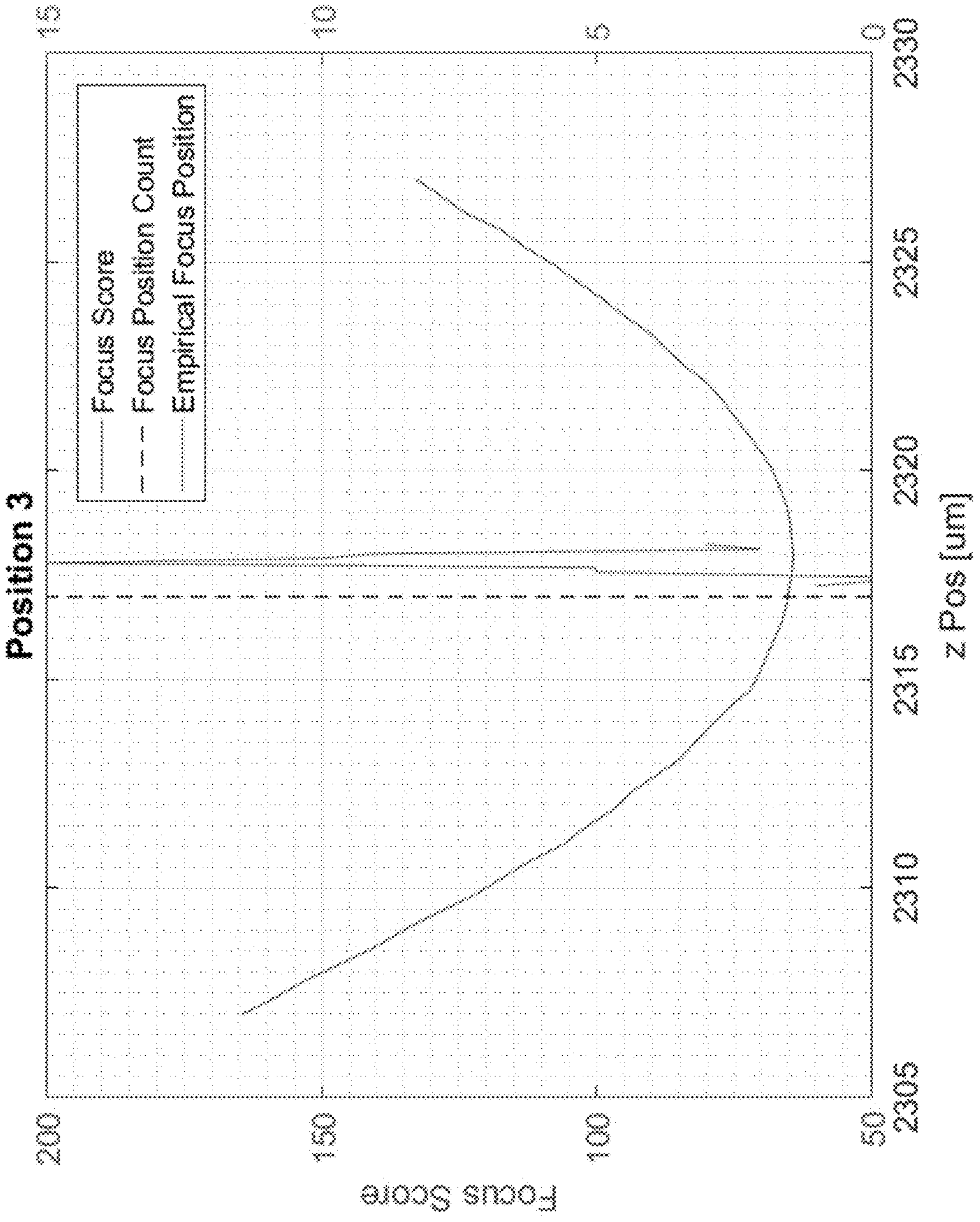
FIG. 6 shows experimental results of determining optimal autofocus using interferometry based systems, according to embodiments of the present disclosure.

FIG. 6 shows an example of determining the accuracy and precision of the autofocus routine by module 154 used in the present system. For example, a user may manually determine the focus position. Once the focus position is determined, the system may obtain a z-stack of images, which is a series of images taken by varying the focus in the z direction in small increments. The autofocus algorithm may be iterated a set number of times, e.g., 10 times, 20 times, 50 times, etc. until obtaining a result that is close to the manual focus position. The automated focus position may be compared to a manual focus position to ensure that the autofocus technique is performing within a specific tolerance. This may be repeated periodically to evaluate the accuracy of the autofocus position.

In the graph of FIG. 6, the automated focus (focus score) and the user identified focus (empirical focus position) are illustrated. As shown by this graph, the results are in good agreement, with both being at or near to the minimum of the focus score. In some aspects, this technique may be used to determine the automated focus position within 0.33 μm standard deviations with a range of 1 μm of the empirical position.

Non-uniform phase delay through the system may be introduced by optical systems, a variation in the optical path due to meniscus, changes in temperature, etc.

Figure 7:
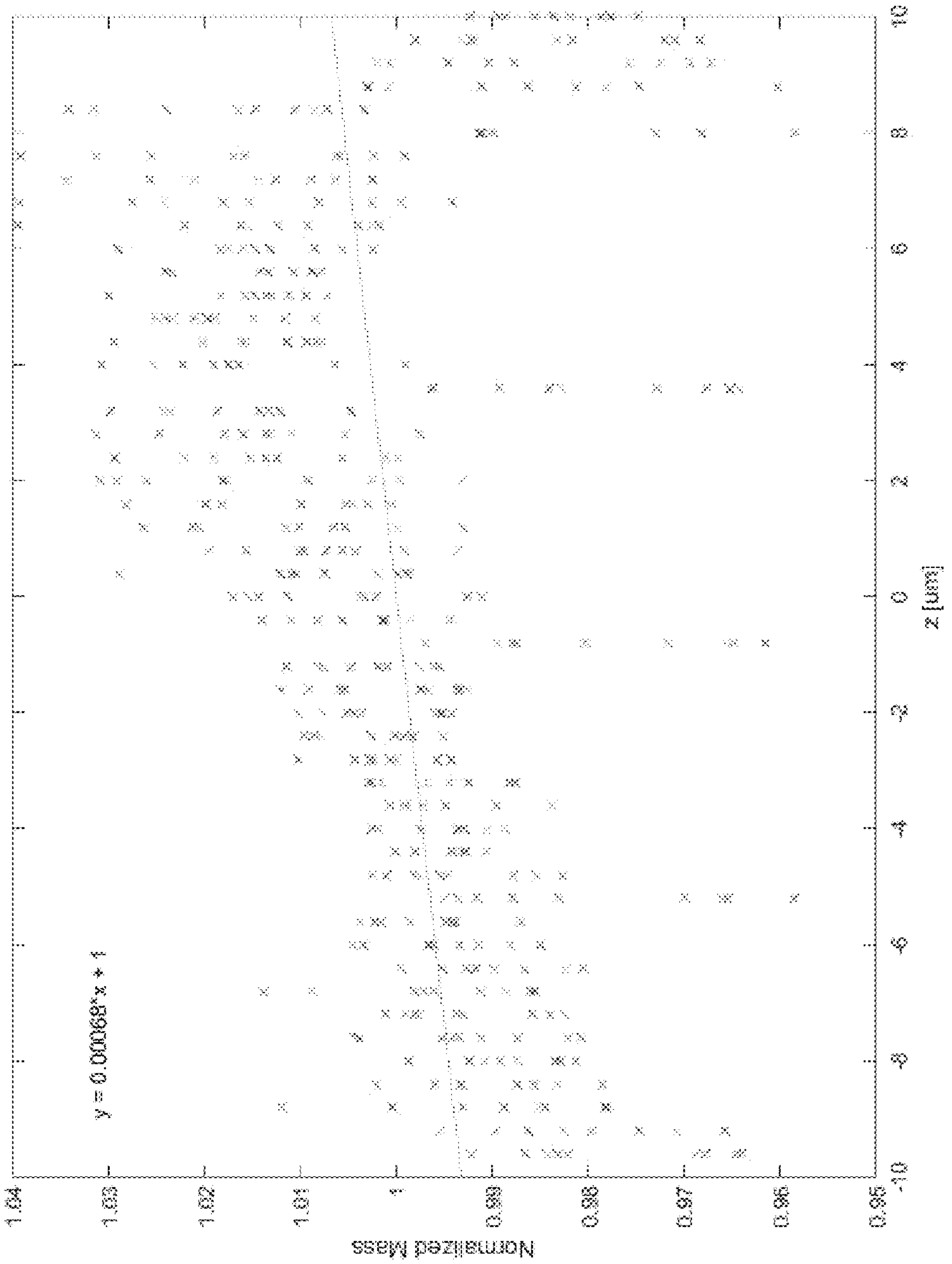
FIG. 7 shows experimental results of determining mass effects on autofocus using interferometry based systems, according to embodiments of the present disclosure.

FIG. 7 shows experimental results of determining the effect of focus position on mass measurements. The mass was calculated at different z (vertical) positions. The data was fit with a line having a slope of about 0.07% per μm, which indicates that the error due to autofocus imprecision was of the order of 0.1%. The error due to the light source was about 0.5%. Thus, the autofocus algorithm was determined to be consistent and to be a small source of error. The time to autofocus was about ~2.2 s per position, but may be reduced to about ~1.5 with a minimal effect on accuracy. In various implementations, example autofocusing routines may be consistent and fast, and may improve on previous speeds by four or five times or more. For example, compared to other example routines that may take 13 seconds or more for a single image where the focusing portion takes up 12.5 seconds, example autofocusing routines described herein may improve the technology to focus in less than three seconds, less than two seconds, etc.

Figure 8:
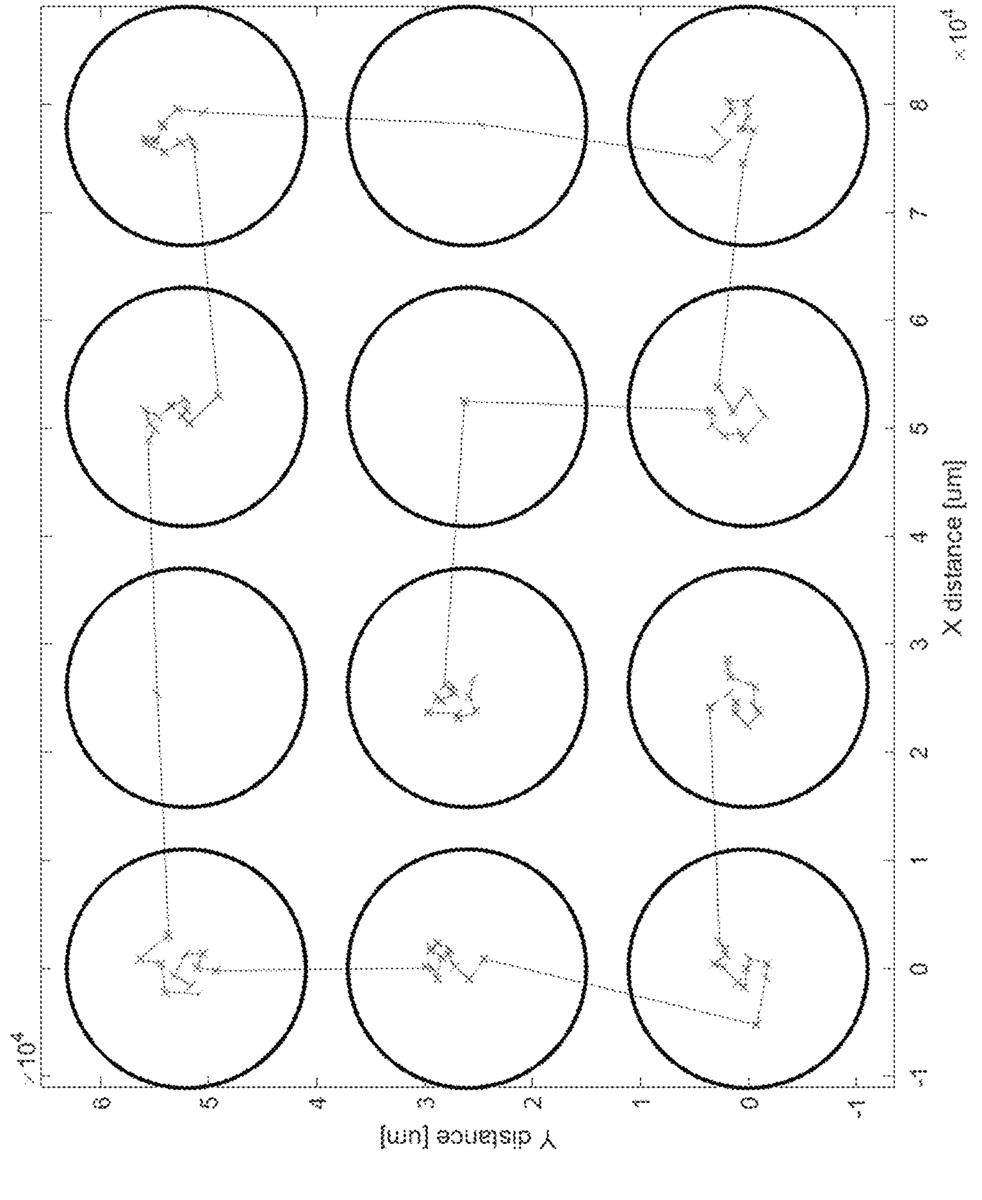
FIG. 8 shows an example trajectory over an area (e.g., in this case, a twelve well plate) in which the objects are placed in interferometry based systems, according to embodiments of the present disclosure.

FIG. 8 shows an example technique for determining a trajectory. Any suitable technique may be used, and in general, a trajectory to image each well position may be determined by: (1) including each well (containing an object to be imaged) in the path, and (2) minimizing the overall distance traveled. Optimization of the trajectory increases throughput and minimizes the time between successive images for each position.

Figure 9B:
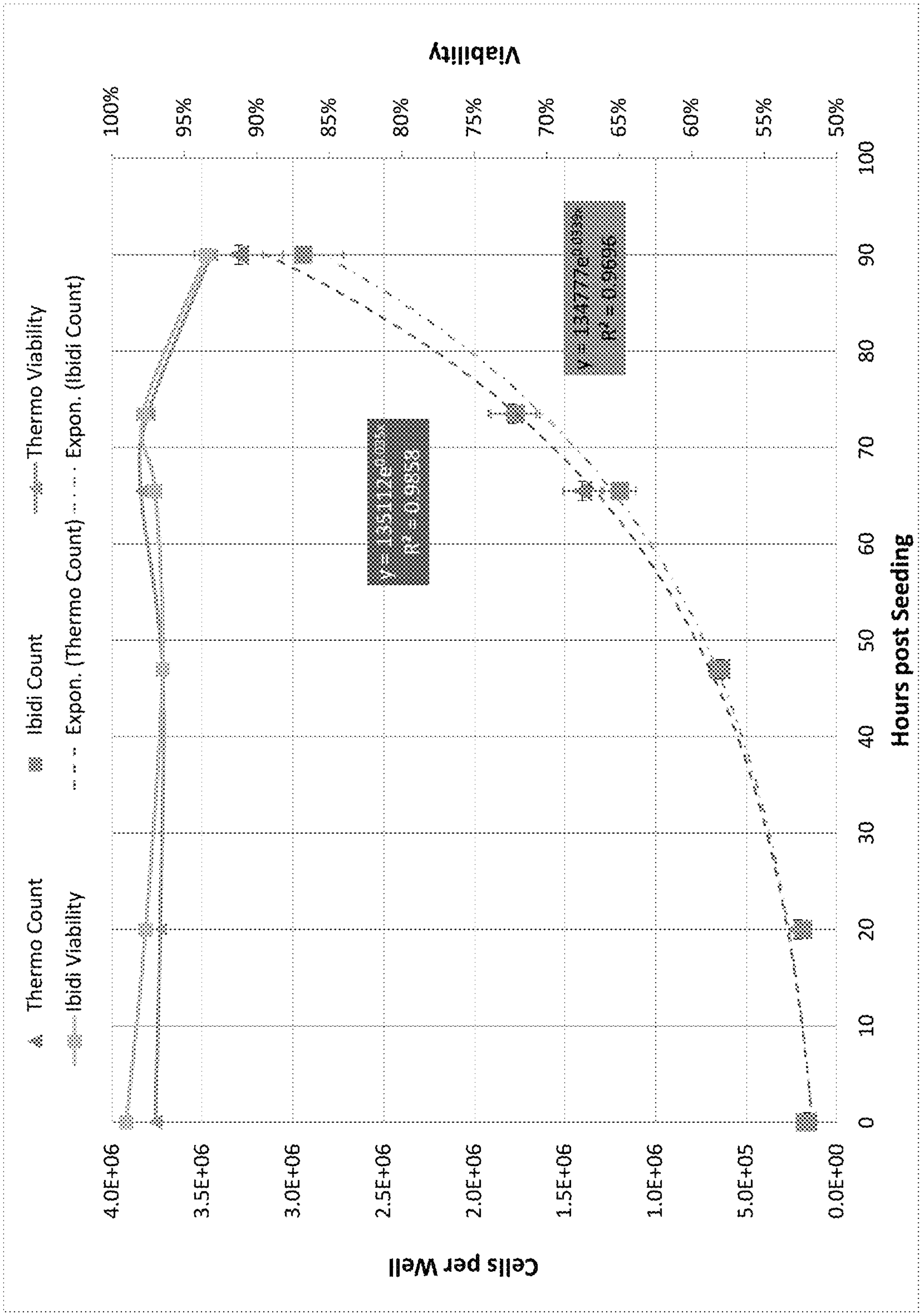

FIGS. 9A-9B show a sample table and graph for optimizing environmental conditions. In this example, EC.7 cells were seeded at $2\times10^4$ cells/cm$^2$ in two six well plates and placed in an incubator. After 8-12 hours, the cells in the first well were detached and counted ($t_0$). One plate was moved to the stage incubator, where cells in a well were detached twice a day (morning and evening) and counted, for a total of five time points. The cells in the incubator (control) were also similarly detached and counted. The differences between the incubated cells in the incubator and on the microscope stage were determined and were found to be less than about 4%.

Figure 10A:
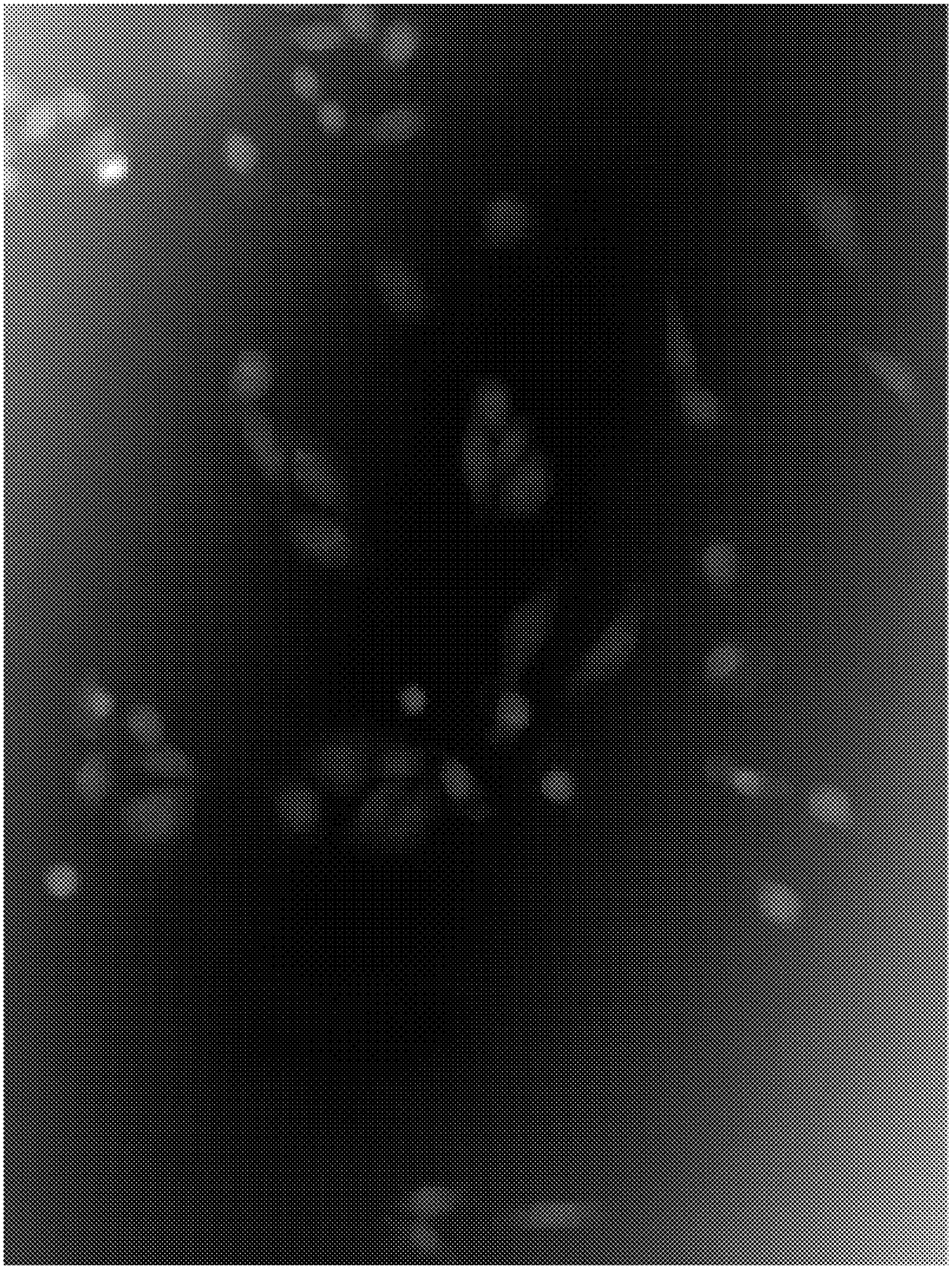
FIGS. 10A, 10B and 10C show images of cells and corresponding intensities before background correction, according to embodiments of the present disclosure.
Figure 10B:
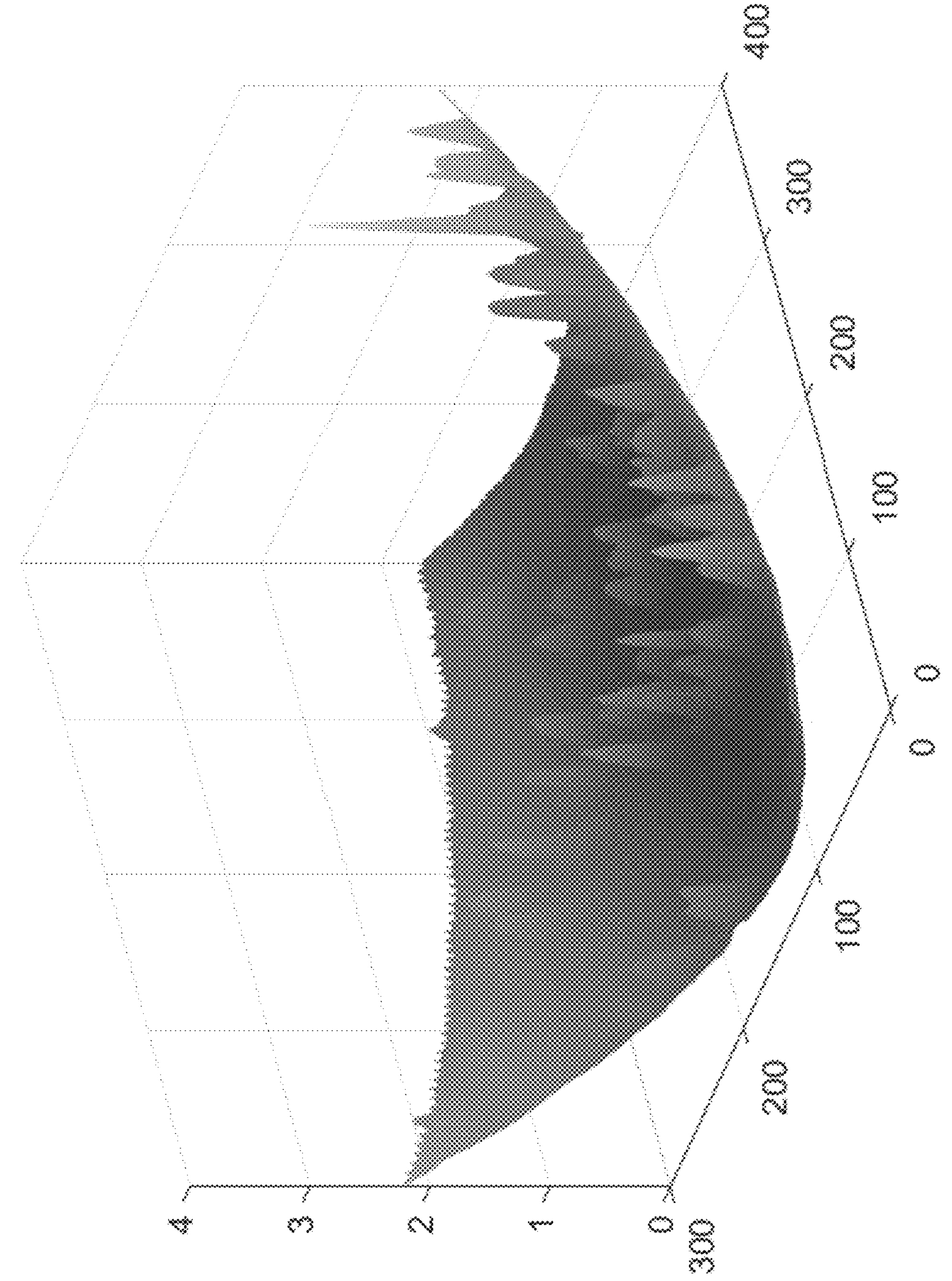
Figure 10C:
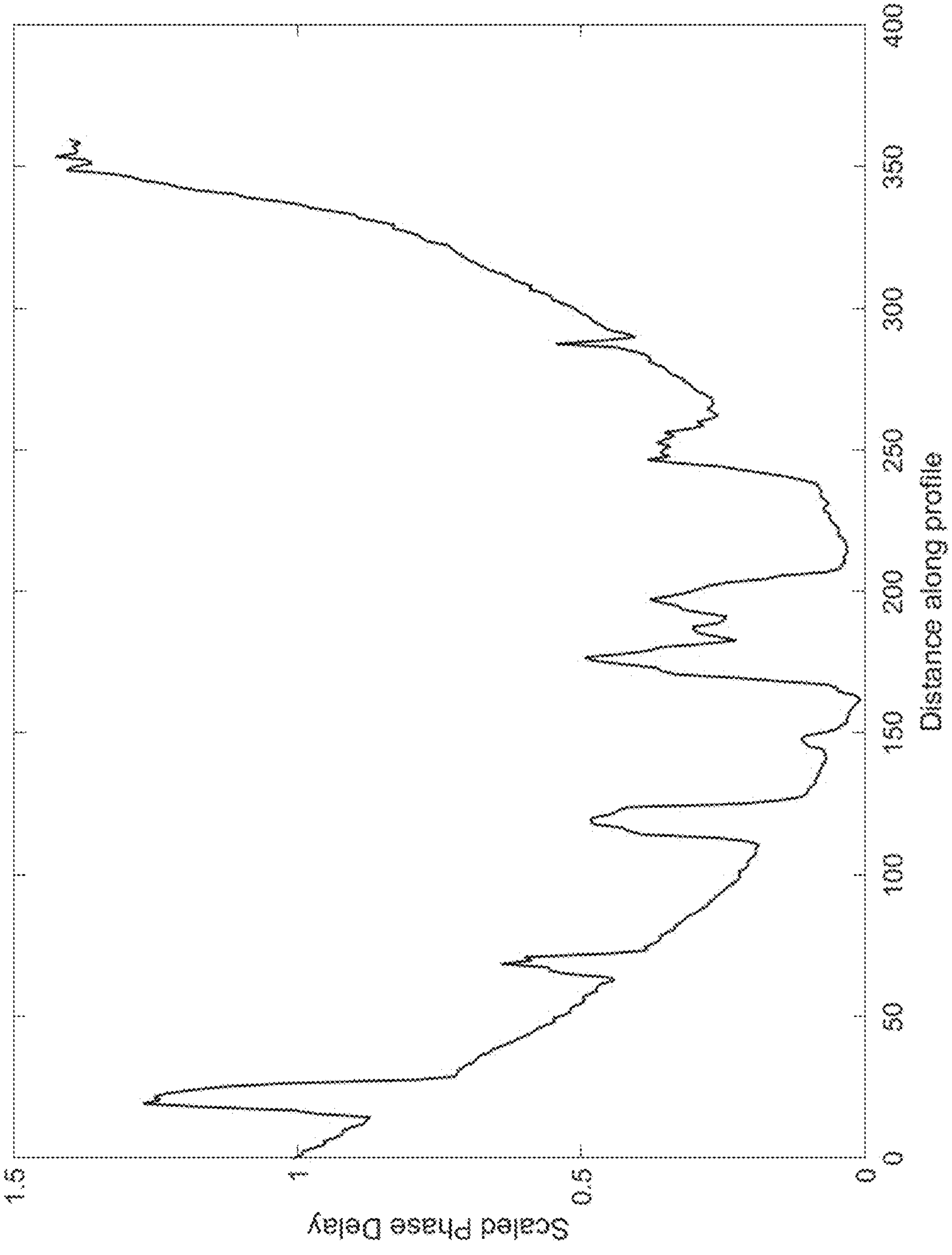

Images with an uneven background need to be corrected to obtain only cell contribution to phase delay. FIG. 10A shows an image that has not undergone background correction. FIG. 10B shows an intensity plot of the same image (FIG. 10A). FIG. 10C shows another plot showing scaled phase delay versus distance along a profile.

The process for background correction is shown in FIGS. 11A-11D, with reference to a profile (x or y position of the image). As shown in corresponding FIG. 10A, the light intensity at the corner of the image is high, making meaningful comparison of the data in the image difficult. To resolve this, a novel background correction technique is applied. This technique involves fitting the image or a portion thereof with a first function, classifying pixels as background or object, and then fitting only the background with a second function, e.g., a higher order polynomial than the first function. Once the background has been fitted with the second equation, the background can be removed from the image or portion thereof by subtraction.

Figure 11A:
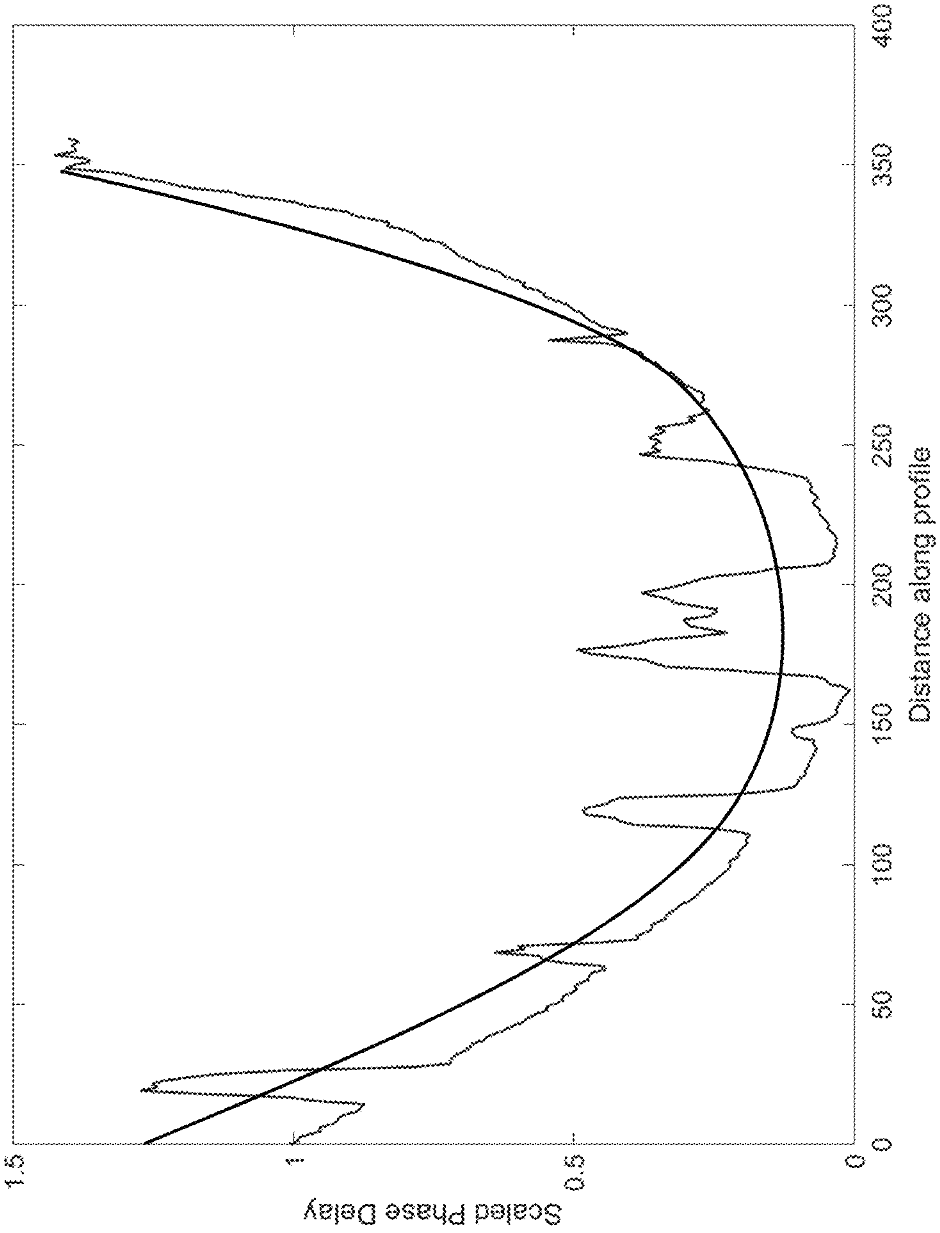
FIGS. 11A, 11B, 11C and 11D show example operations for background correction of FIGS. 10A-10C, according to embodiments of the present disclosure.
Figure 11B:
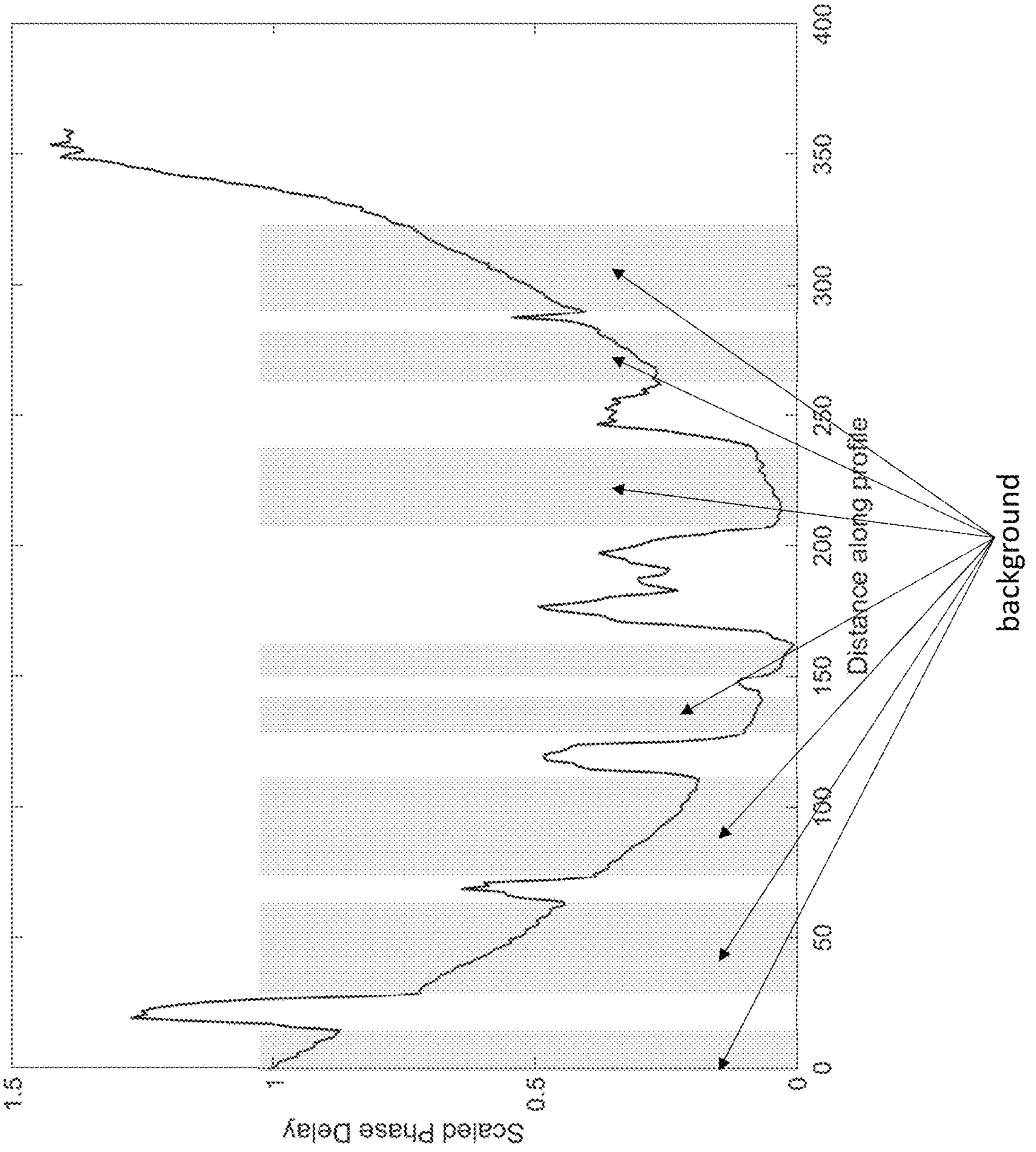
Figure 11C:
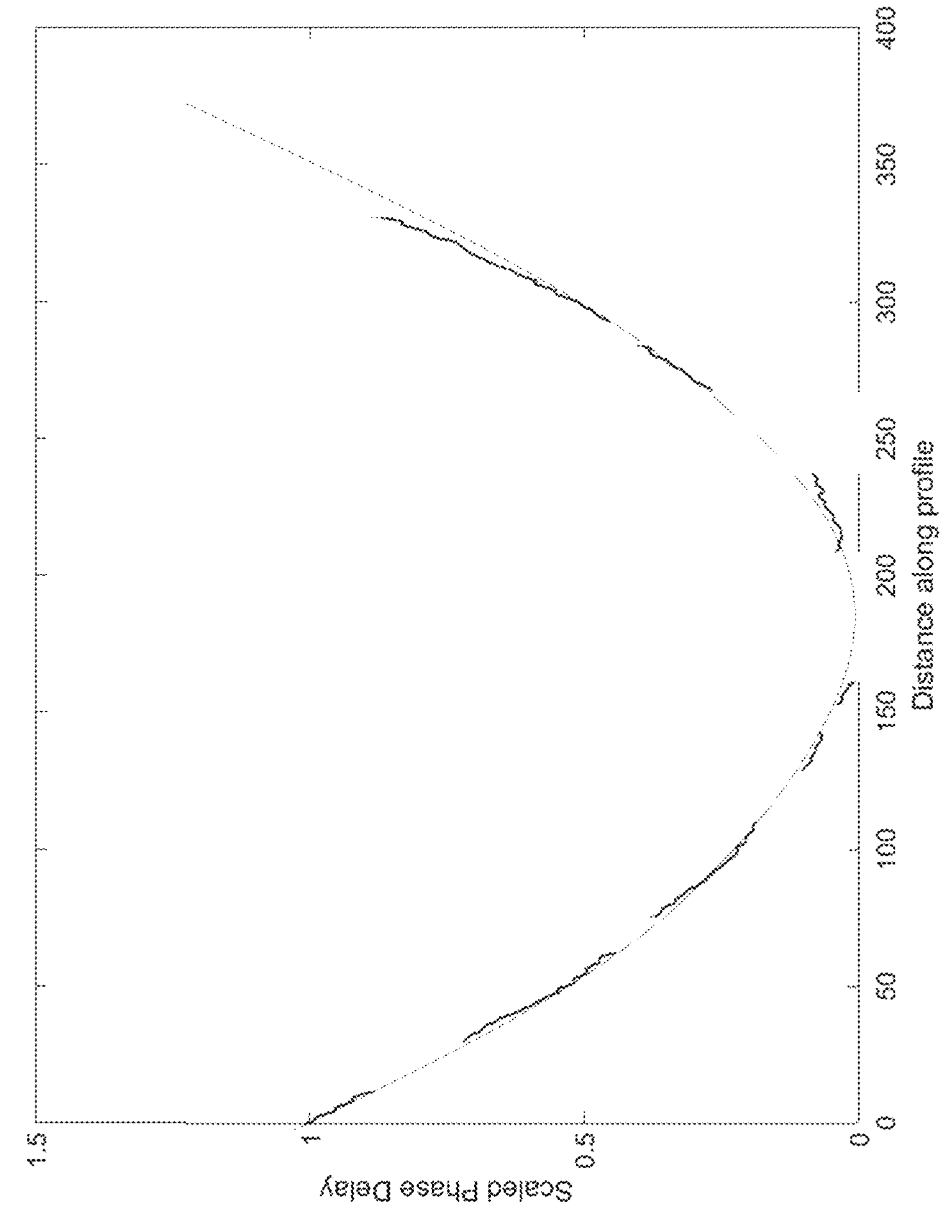
Figure 11D:
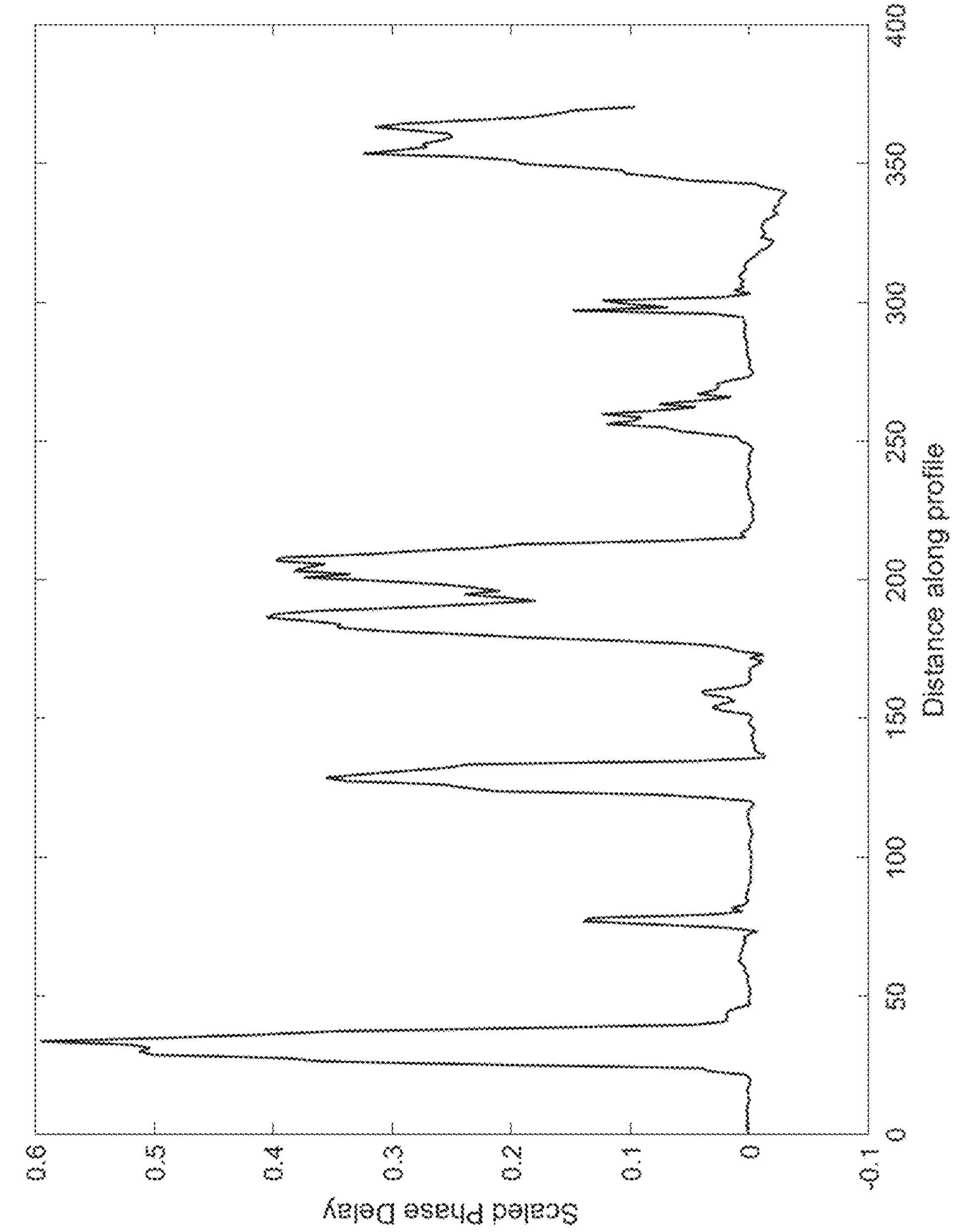
Figure 11D:
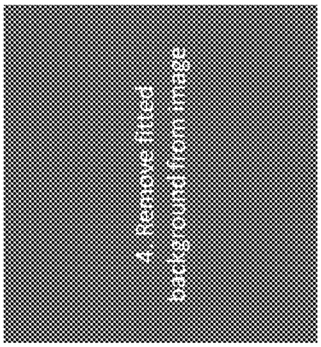

In one example, as shown in FIG. 11A, initial flattening was performed to fit the entire image (background and cells) with a low order polynomial (n=2 or 3). The fitted curve may be subtracted from the image for a first approximation. As shown in FIG. 11B, the second step involved using clustering (e.g., a k-means algorithm) after the first approximation to classify pixels as background vs object. All of the pixels in the shaded region are considered background. As shown in FIG. 11C, a higher order polynomial (n=5) was fit only to background pixels to generate a background fitted function. As shown in FIG. 11D, the background fitted function is subtracted from the image or a portion thereof to generate a corrected background image. An example protocol for performing this technique is provided; however, many different variations exist, and all are contemplated herein.

Figure 12A:
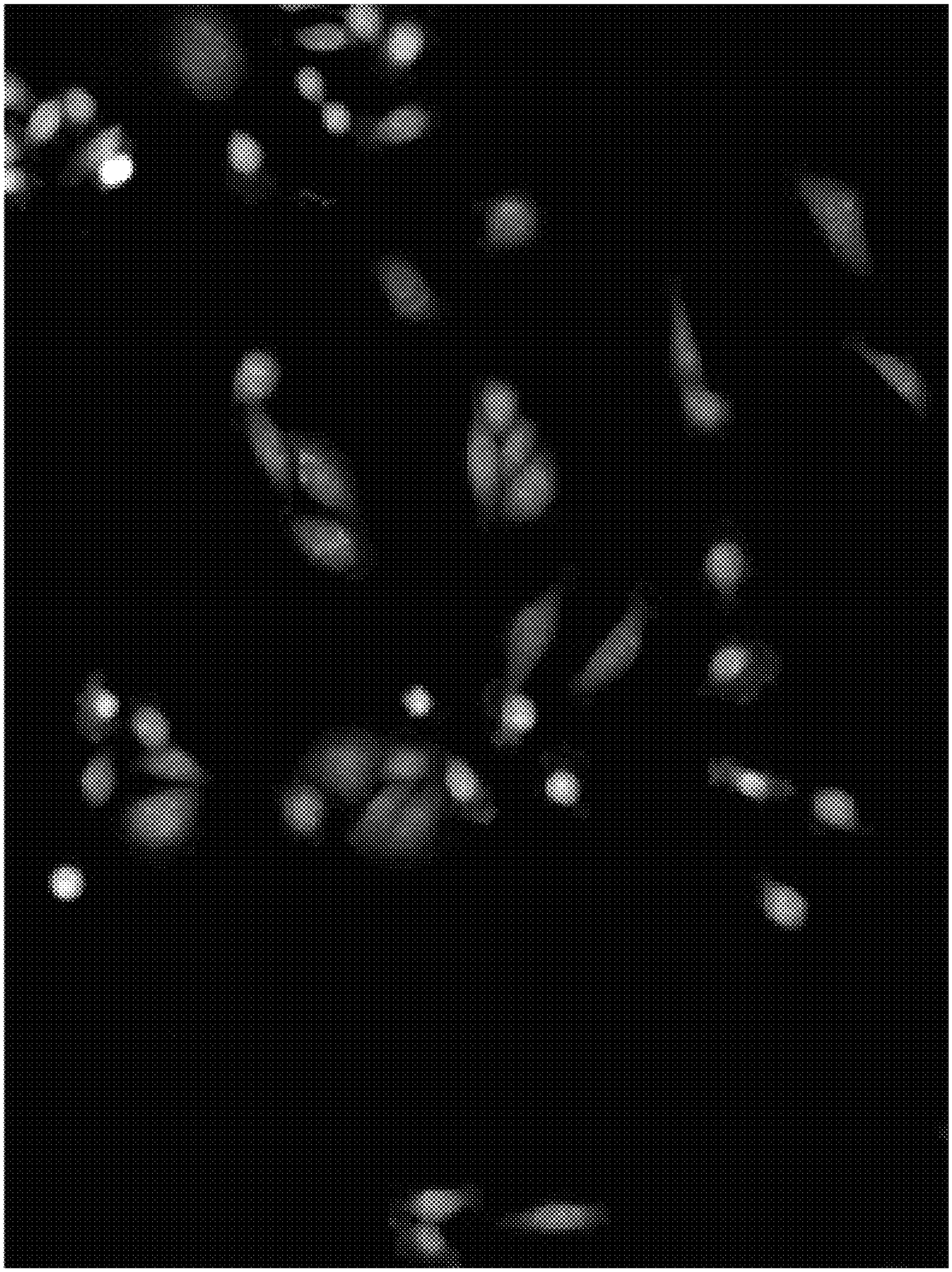
FIGS. 12A, 12B and 12C show images of cells and corresponding intensities after background correction of FIGS. 10A-10C, according to embodiments of the present disclosure.
Figure 12B:
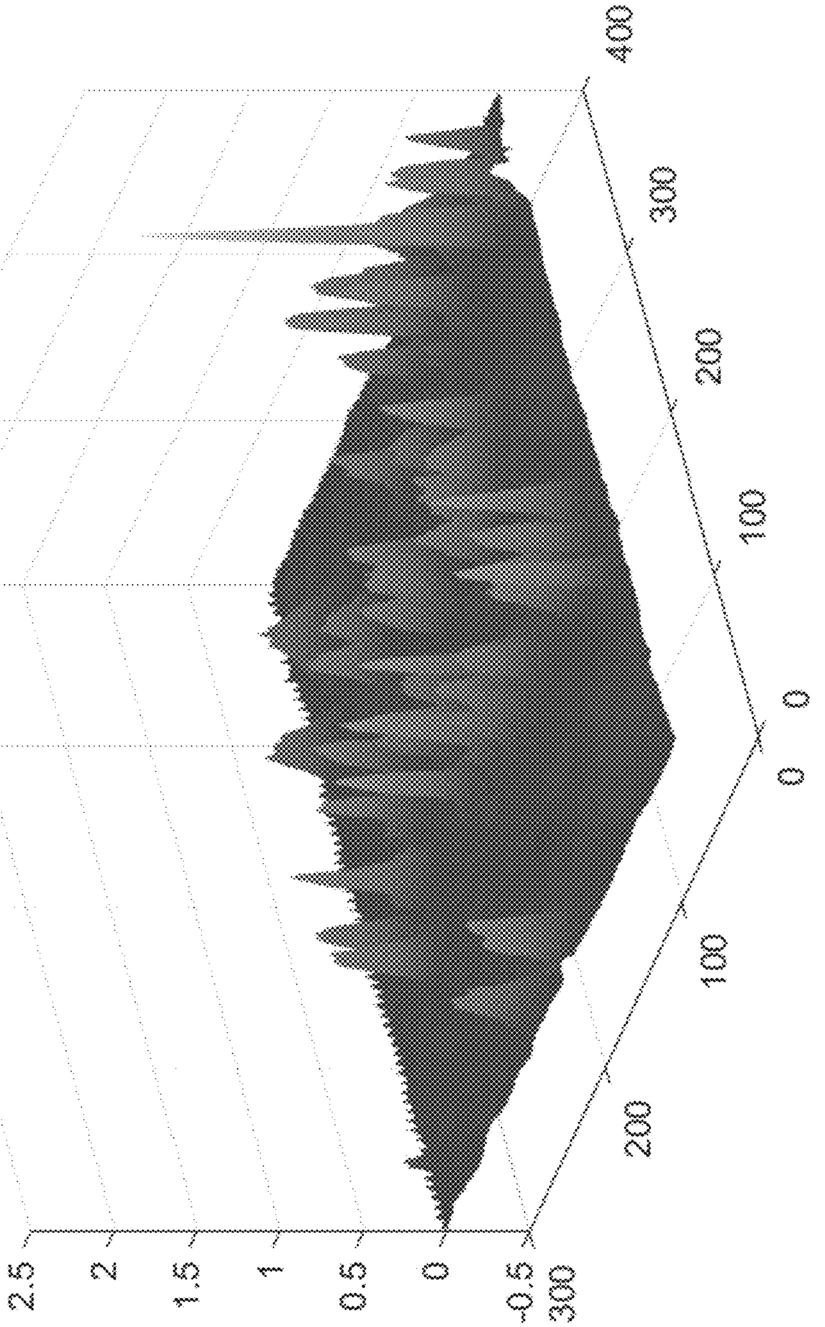
Figure 12C:
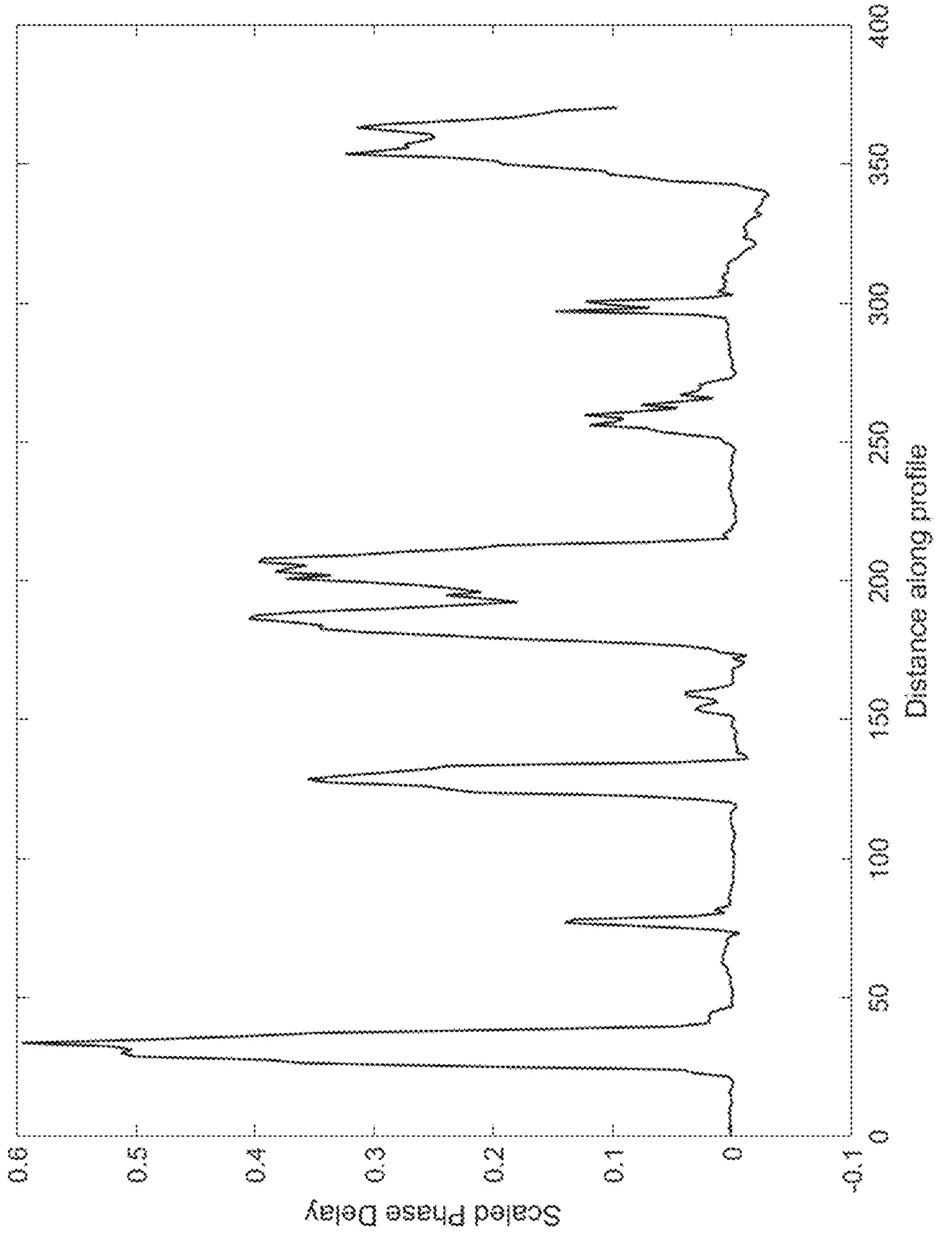

The next figures show images after background correction (see also, FIGS. 10A-10C for comparison). FIG. 12A shows an image that has undergone background correction. FIG. 12B shows an intensity plot of the same image (FIG. 12A). FIG. 12C shows another plot showing scaled phase delay versus distance along a profile of FIG. 12B. As shown by these figures, the background noise has been eliminated, leaving pixel intensities that correspond to cells.

Figure 13A:
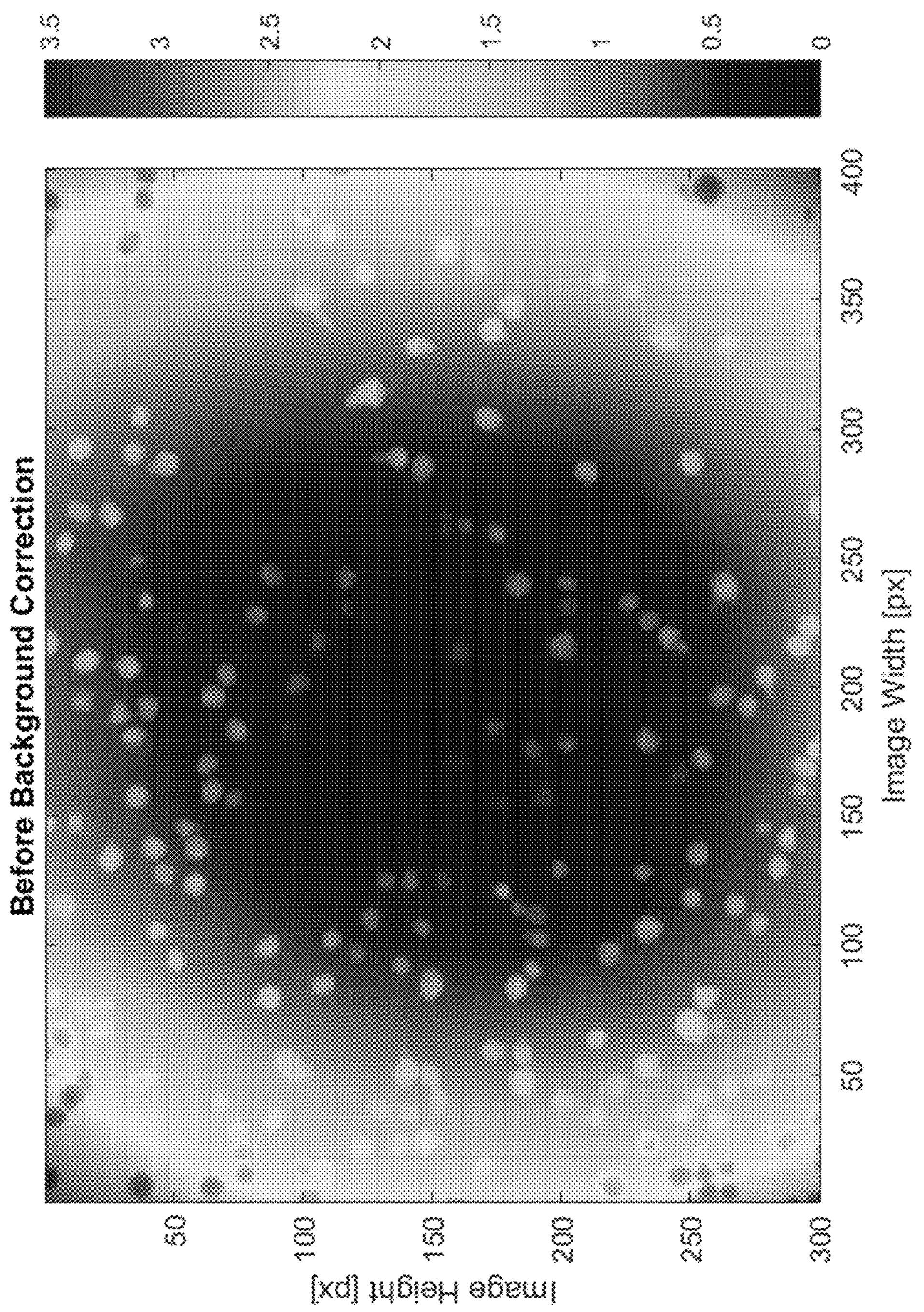
FIGS. 13A, 13B and 13C show additional examples of images of cells and corresponding intensities before background correction, according to embodiments of the present disclosure.
Figure 13B:
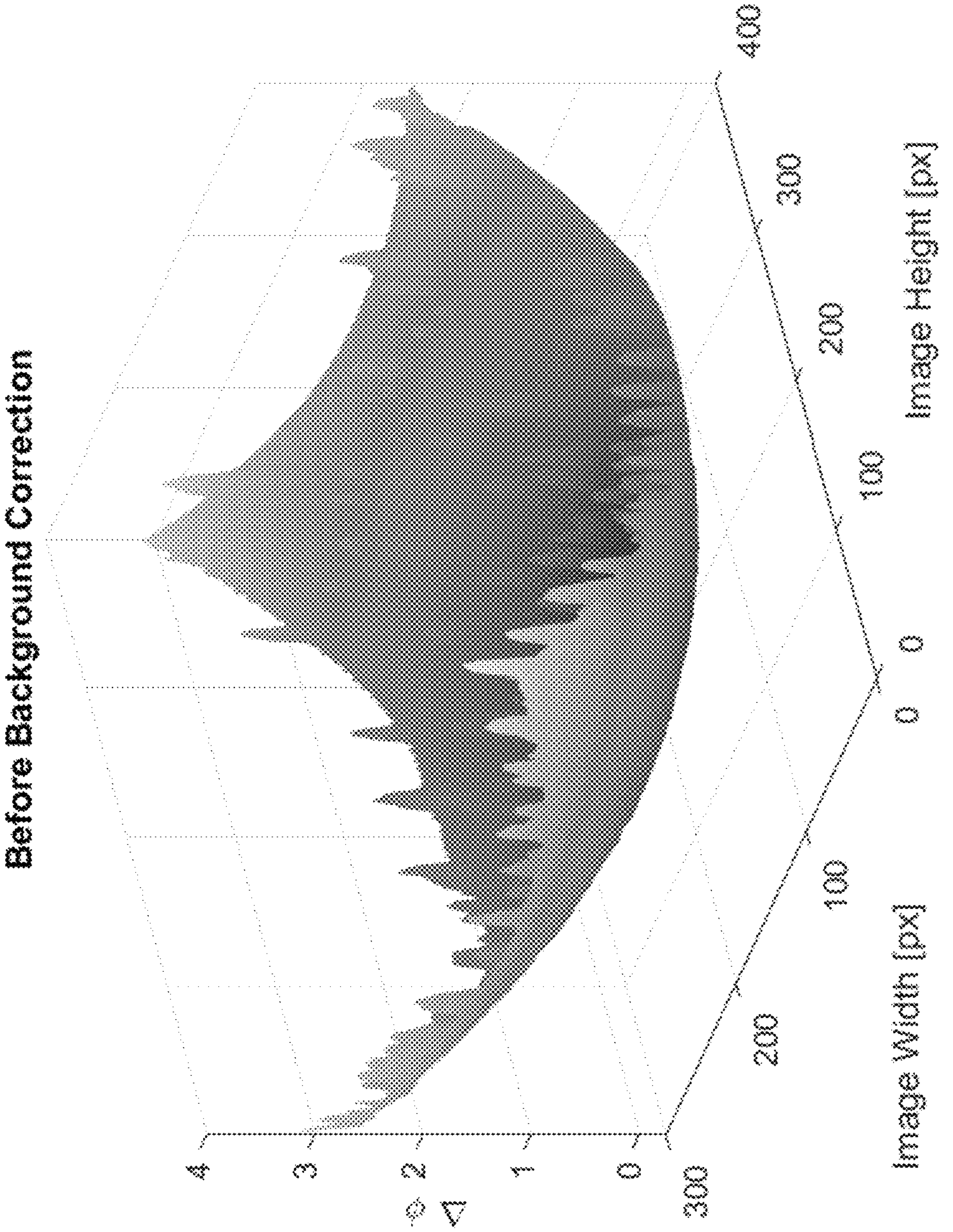
Figure 13C:
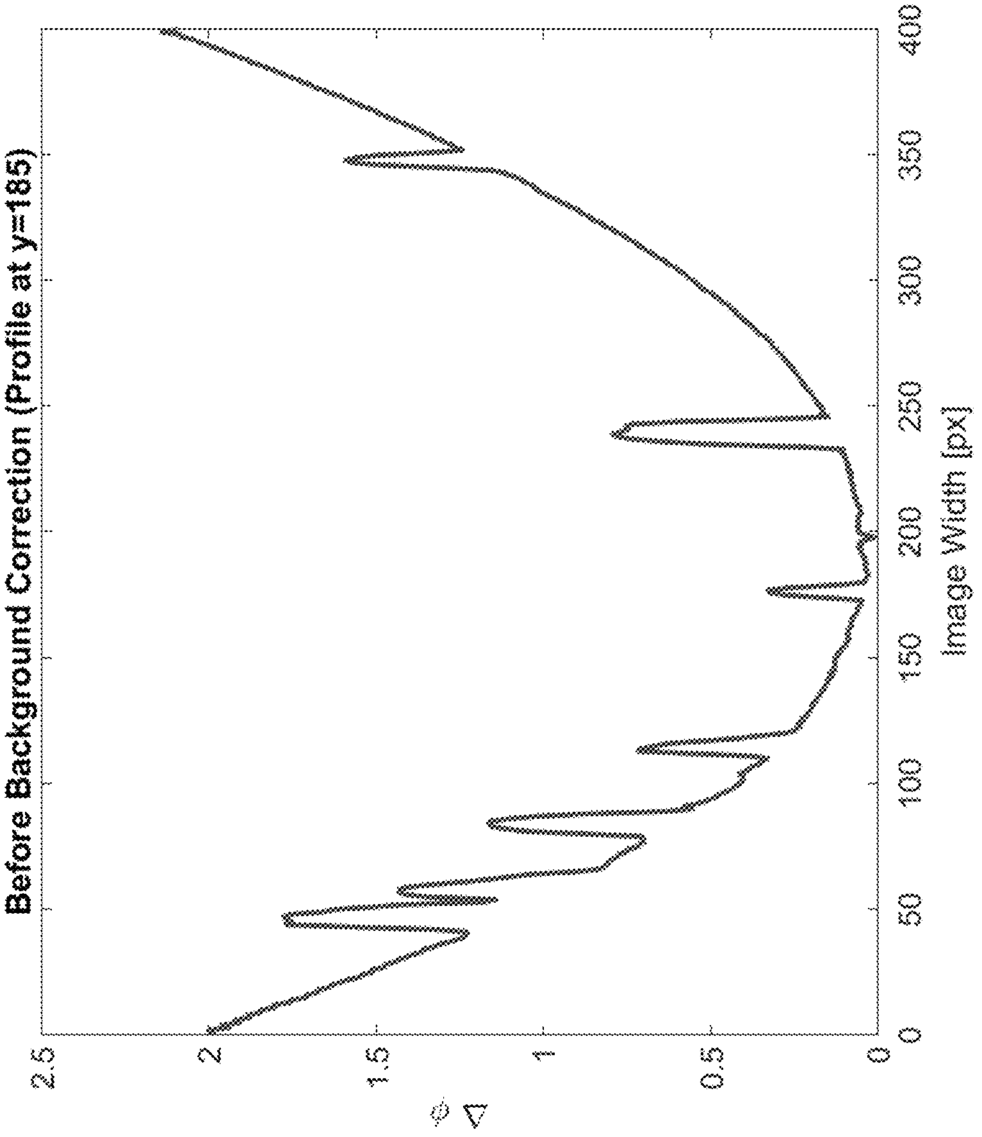
Figure 14A:
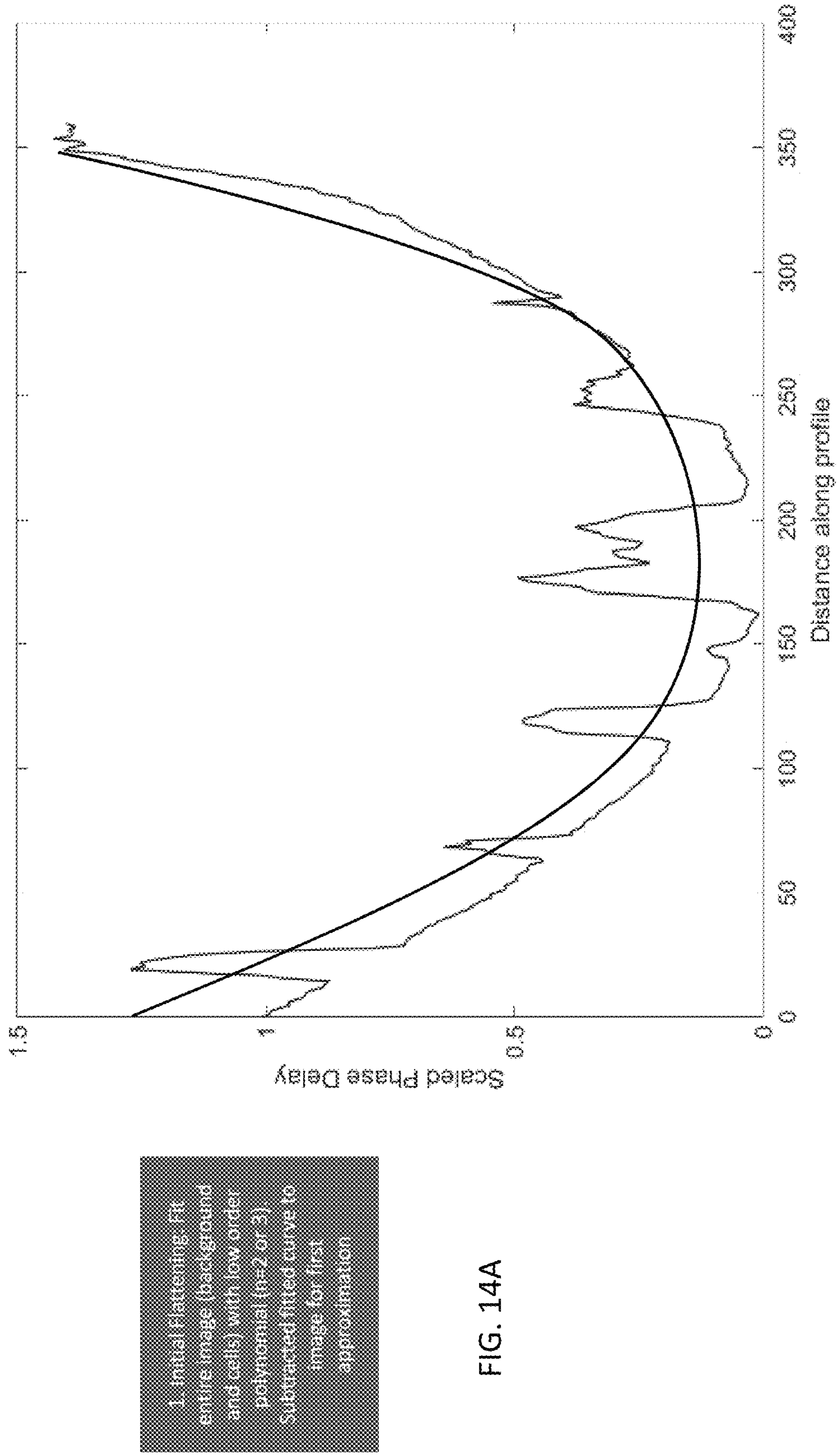
FIGS. 14A, 14B, 14C and 14D show example operations for background correction of FIGS. 13A-13C, according to embodiments of the present disclosure.
Figure 14B:
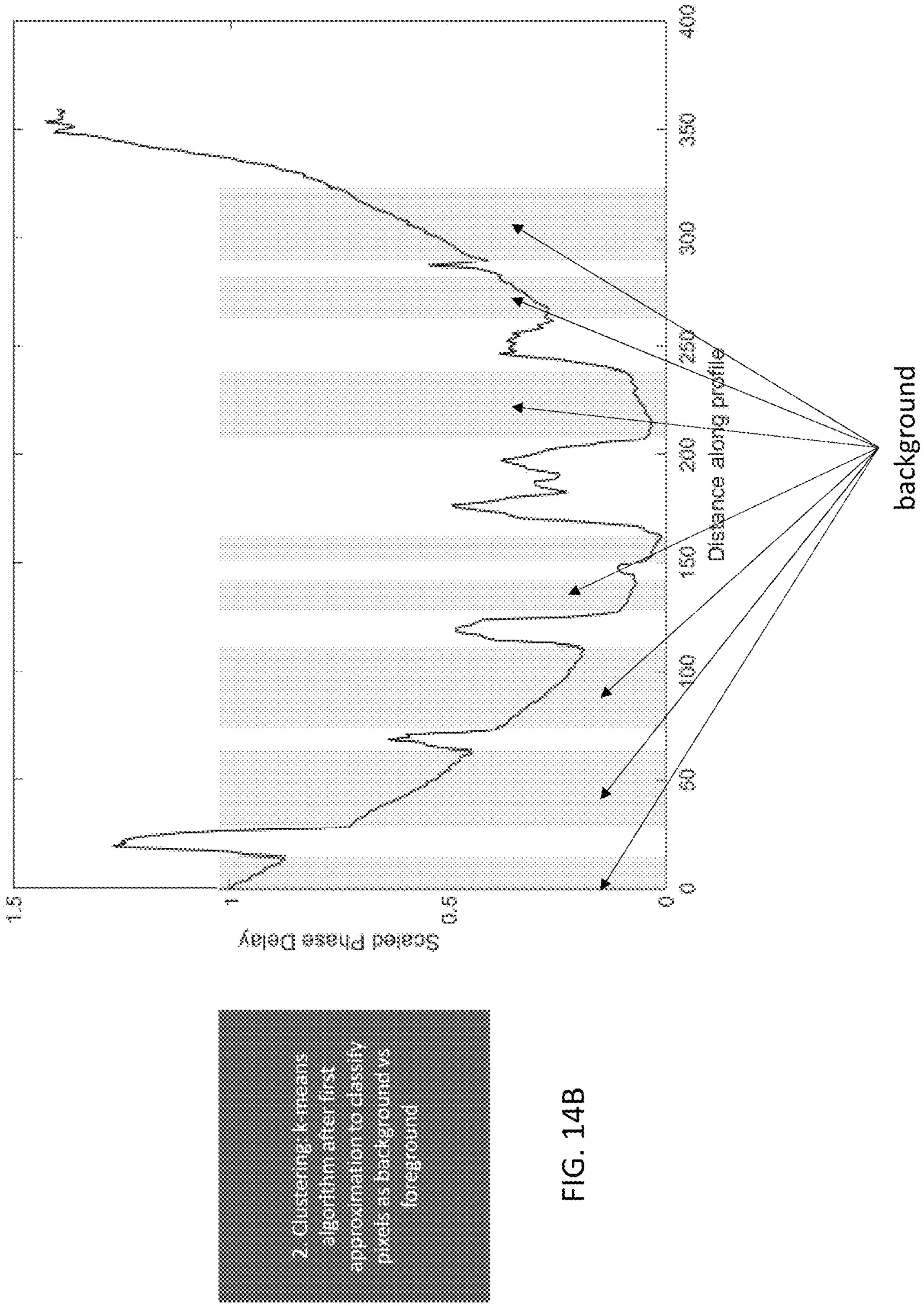
Figure 14C:
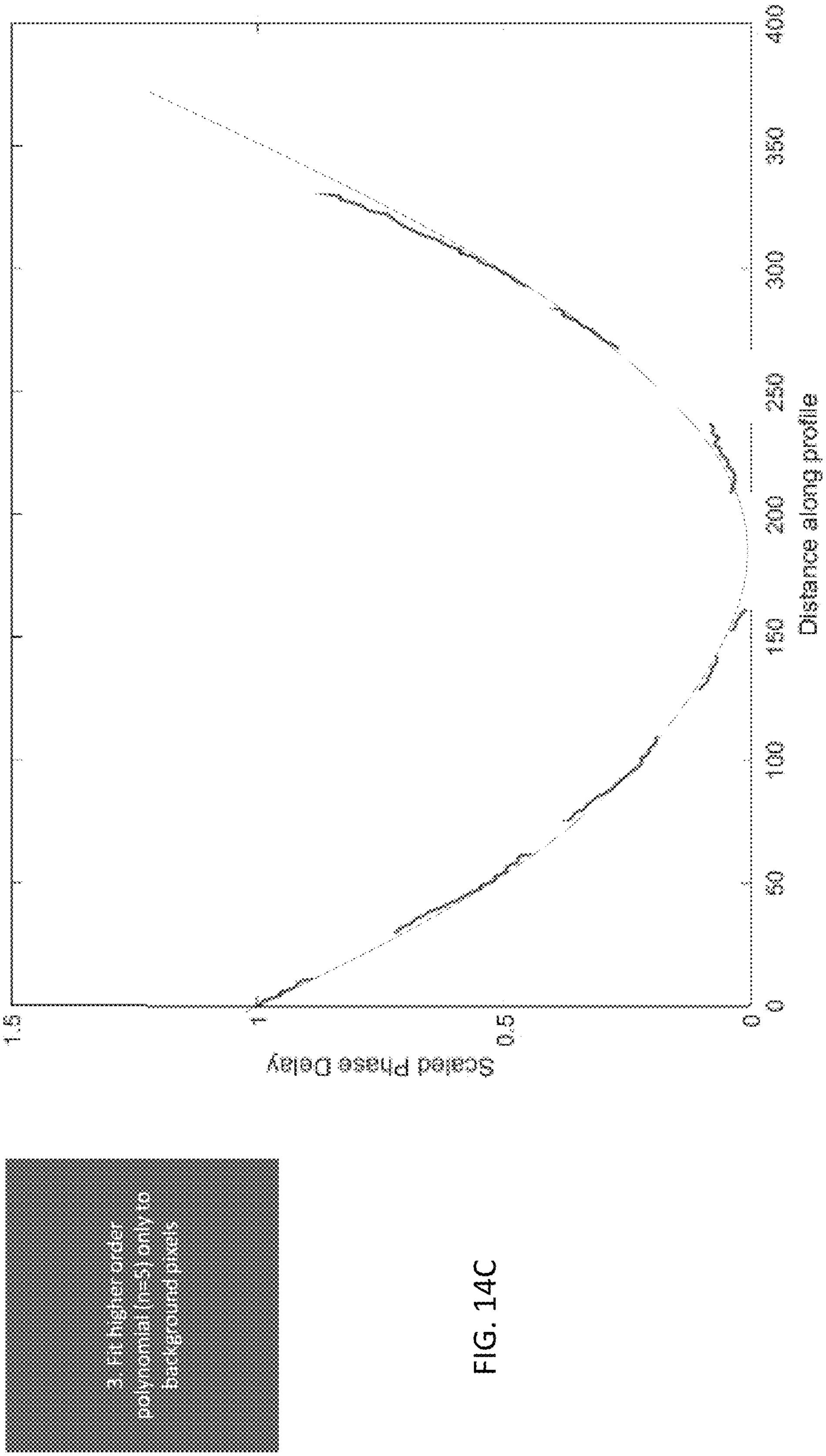
Figure 14D:
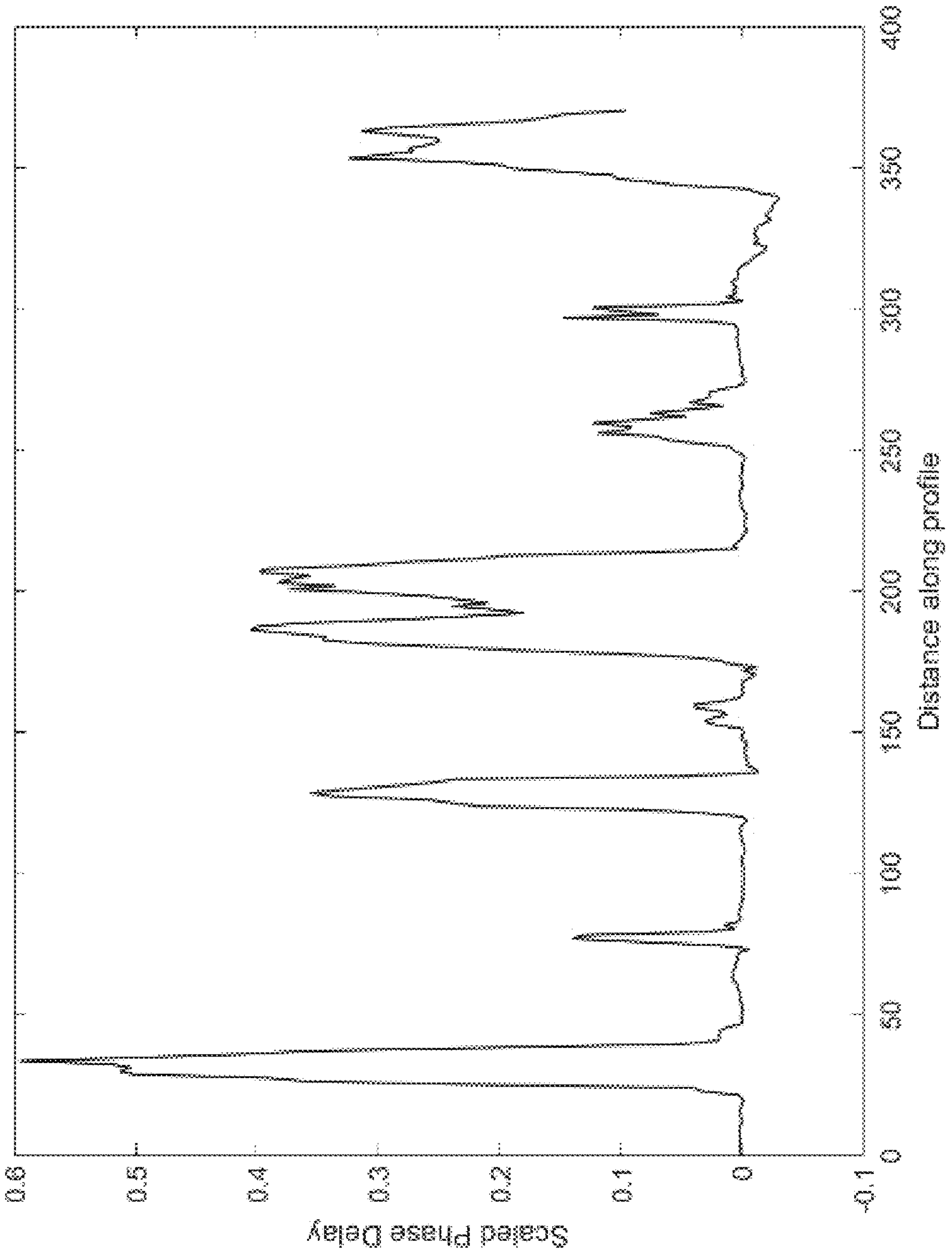
Figure 14D:
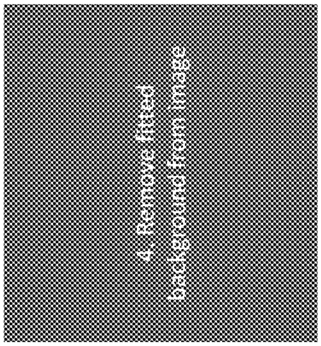

Another example is shown in FIGS. 13A-13C, which shows intensity of images before background correction, including a profile at y=185. FIG. 14A shows initial flattening, in which the entire image or portion thereof (background and cells) is fit with a low order polynomial (n=2 or 3). The fitted curve may be subtracted from the image for a first approximation. As shown in FIG. 14B, the second step involved using clustering (e.g., a k-means algorithm), in some cases after the first approximation, to classify pixels as background vs object. All of the pixels in the shaded region are considered background. As shown in FIG. 14C, a higher order polynomial, that is having a degree higher than the low order polynomial, (n=5 in this case) was fit only to background pixels to generate a background fitted function. As shown in FIG. 11D, the background fitted function is removed (e.g., subtracted) from the image. In various implementations, machine learning techniques may be used to generate various background correction curves, such as using a machine learning model to transition directly from the initial flattening illustrated in FIG. 14A to the background fitted function of FIG. 14C. For example, a machine learning model may be trained to generate a background fitted function according to an initial image that has been fit with a low order polynomial to provide initial flattening, using historical background correction images.

In various implementations, a machine learning model may be trained to classify foreground and background pixels, possibly without the need for initial low order flattening with high accuracy. An example U-Net deep learning model for pixel classification is illustrated in FIG. 34, although other suitable model types may be used in various implementations. Additional details on one example U-Net model architecture may be found in Ronneberger et al., U-Net: Convolutional Networks for Biomedical Image Segmentation (2015). In one example implementation, PyTorch was used to develop a model with 60 million parameters to be learned. Training and validation data included a manually colored set of images, which defined cell boundaries. A script created a filled mask of all of the cells, and a set of 78 images was split into 61 training images and 17 validation images. The model included multiple convolution kernels, and was trained for 2000 epochs. The above parameters are provided for purposes of example illustration only, and other models may use other suitable parameters.

Figure 36:
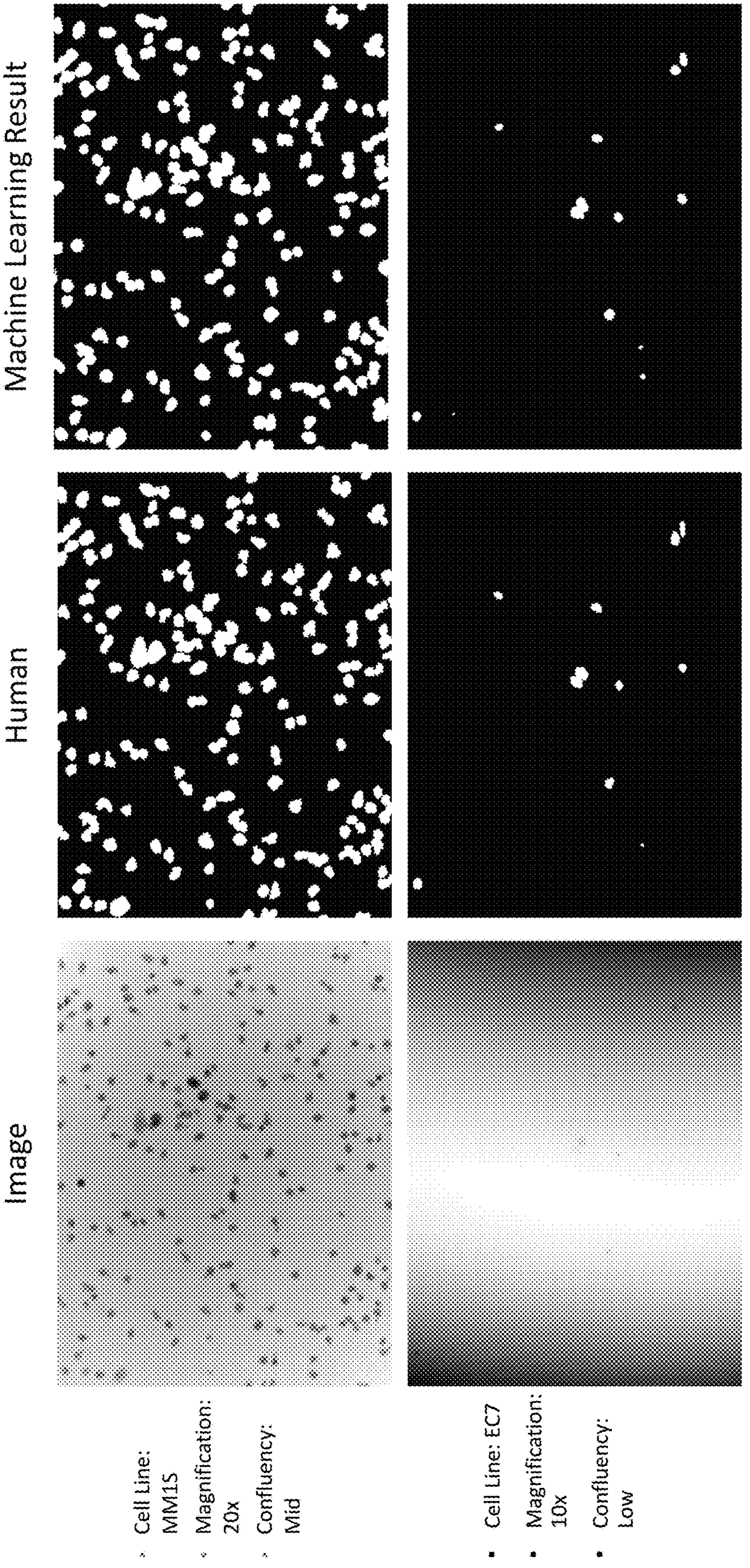
FIG. 36 includes illustrations of example results of using a machine learning model for background identification and removal.

FIG. 35 illustrates example results for a trained model (such as the example model of FIG. 34), illustrating high accuracy, precision and recall when tested on a training data set. FIG. 36 illustrates example plots of background classification of an image based on a human result compared to a machine learning result, for two example cases. One is a cell line MMIS at 20× magnification with mid confluency, and the lower plots are for an EC7 cell line at 10× magnification with low confluency. Both cases illustrate high accuracy results for actual tested machine learning models.

Figure 15A:
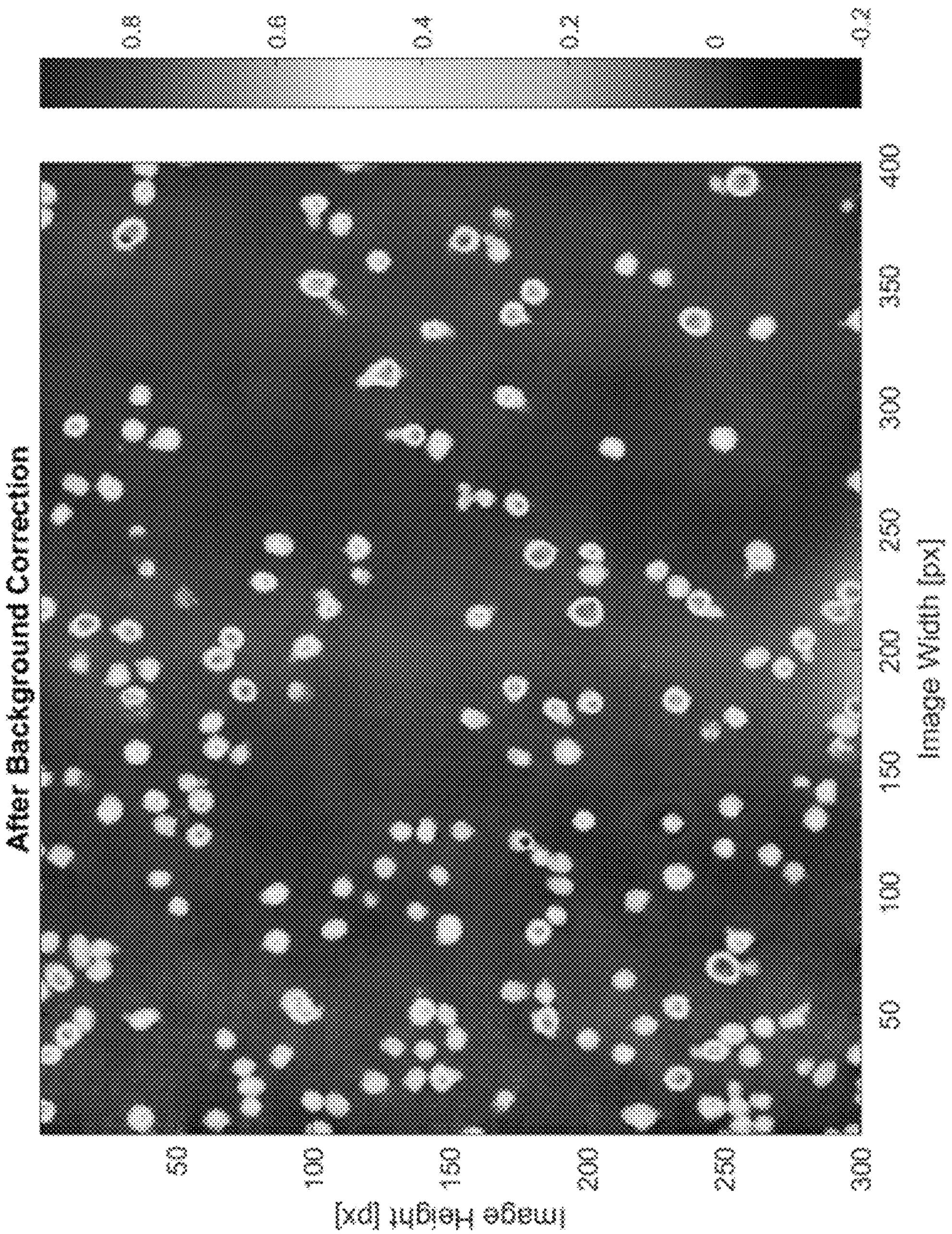
FIGS. 15A, 15B and 15C show images of cells and corresponding intensities after background correction of FIGS. 13A-13C, according to embodiments of the present disclosure.
Figure 15B:
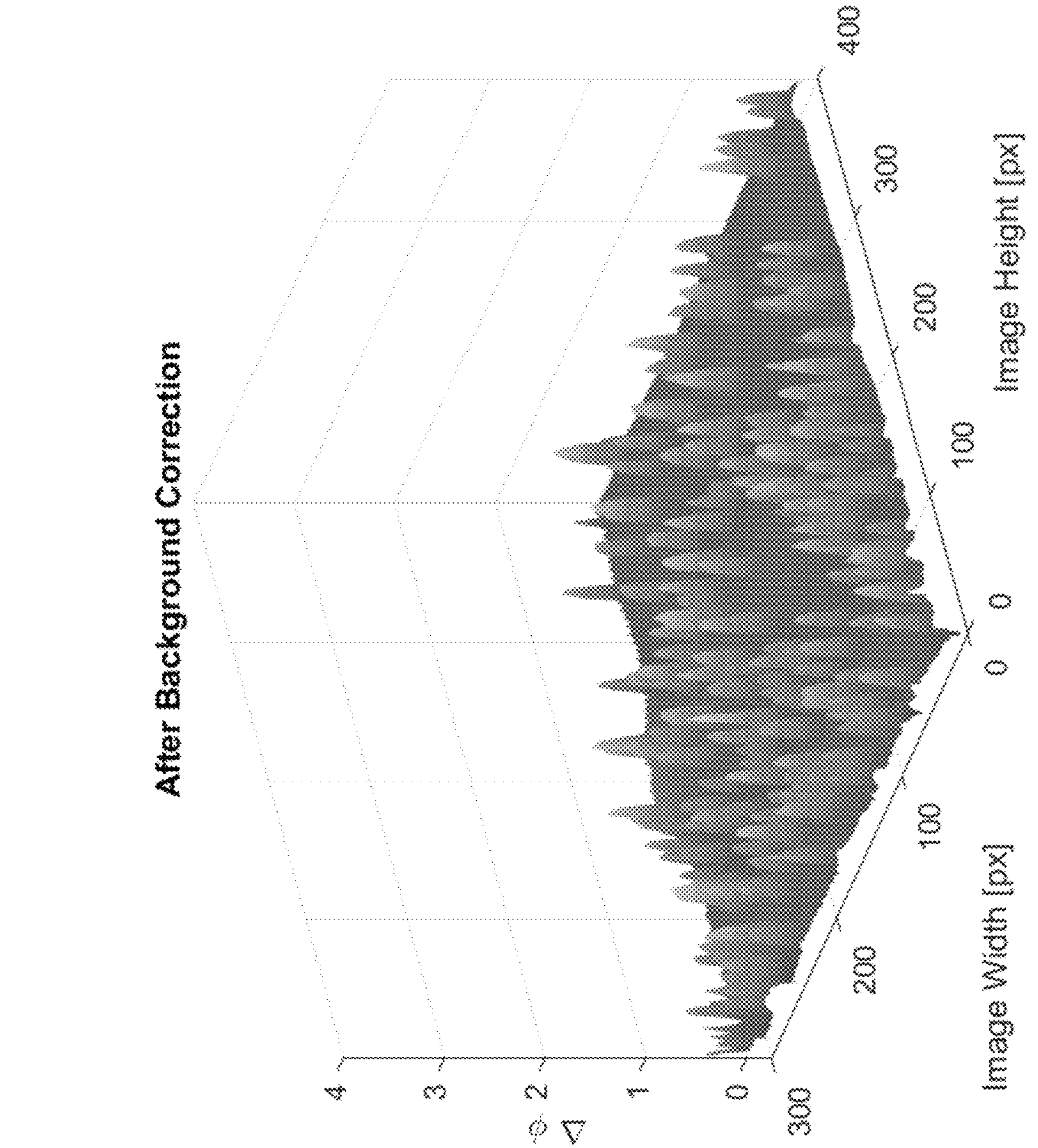
Figure 15C:
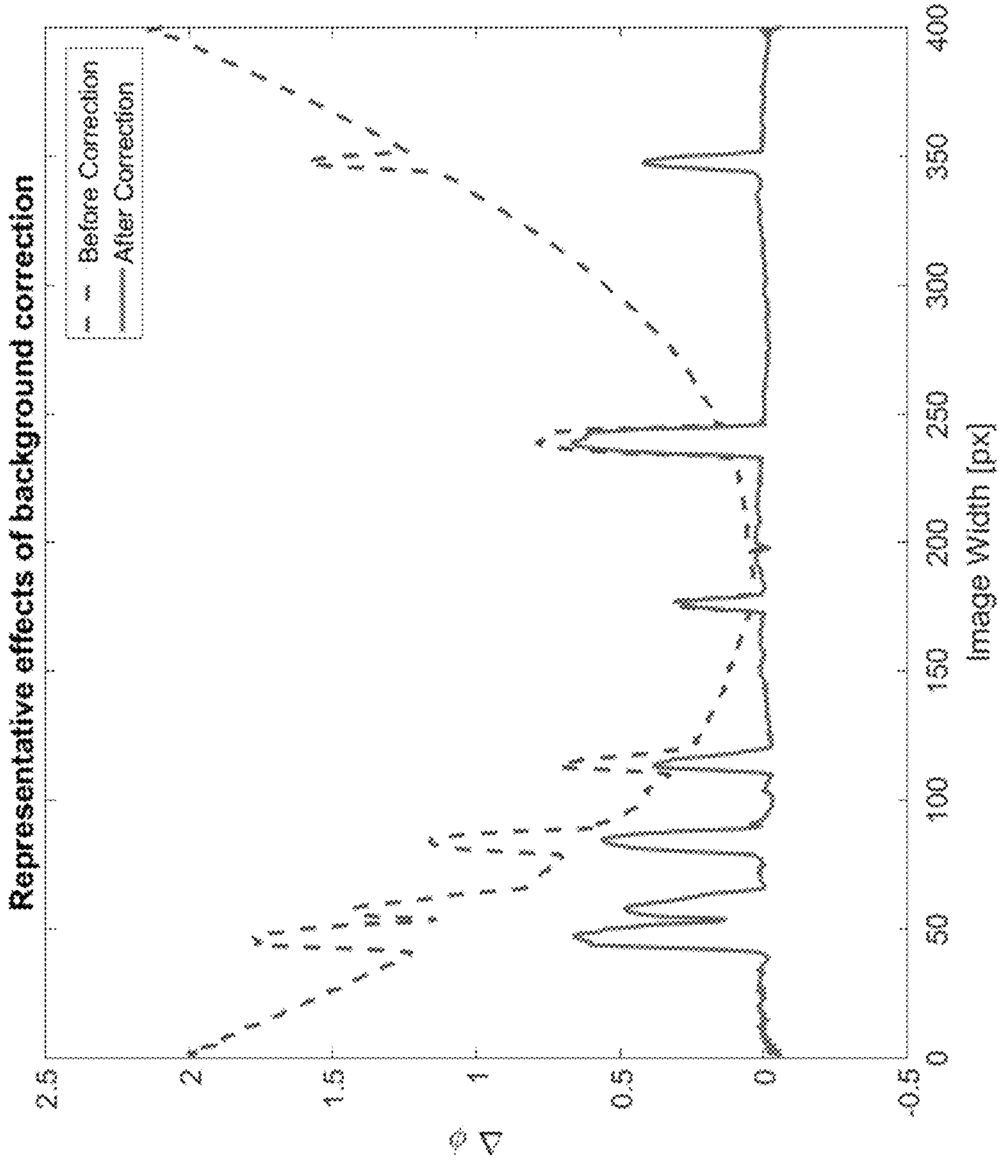

The next figures show images after background correction (see also, FIGS. 13A-13C for comparison). FIG. 15A shows an image that has undergone background correction. FIG. 15B shows an intensity plot of the same image (FIG. 15A). FIG. 15C shows a profile showing scaled phase delay versus distance (FIG. 15B). As shown by these figures, the background noise has been eliminated, leaving pixel intensity.

In order to track individual cells as a function of time, identification of individual cells are needed. Various techniques for identifying cell boundaries are known. Once the cell boundary is identified, integration of the pixel intensity within the cell boundary may be performed to determine a change in mass. In various implementations, machine learning techniques may be used to track individual cells. For example, a training dataset may be created by explicitly watching cells move over time. The cell movements could be mapped to various cell attributes, such as size, shape, morphology, circularity, etc. In various implementations, the dataset could be generated via a mechanical turk process. Example processes for using an interface to communicate with a mechanical turk engine are described in U.S. Pat. No. 9,436,738, titled "Mechanical Turk integrated IDE, systems and method," and issued Sep. 6, 2016, which is incorporated herein by reference. Thus, one aspect of the inventive subject matter is to create a crowdsources cell tracking system that integrates matching learning training data results back into a machine learning system.

Figure 16:
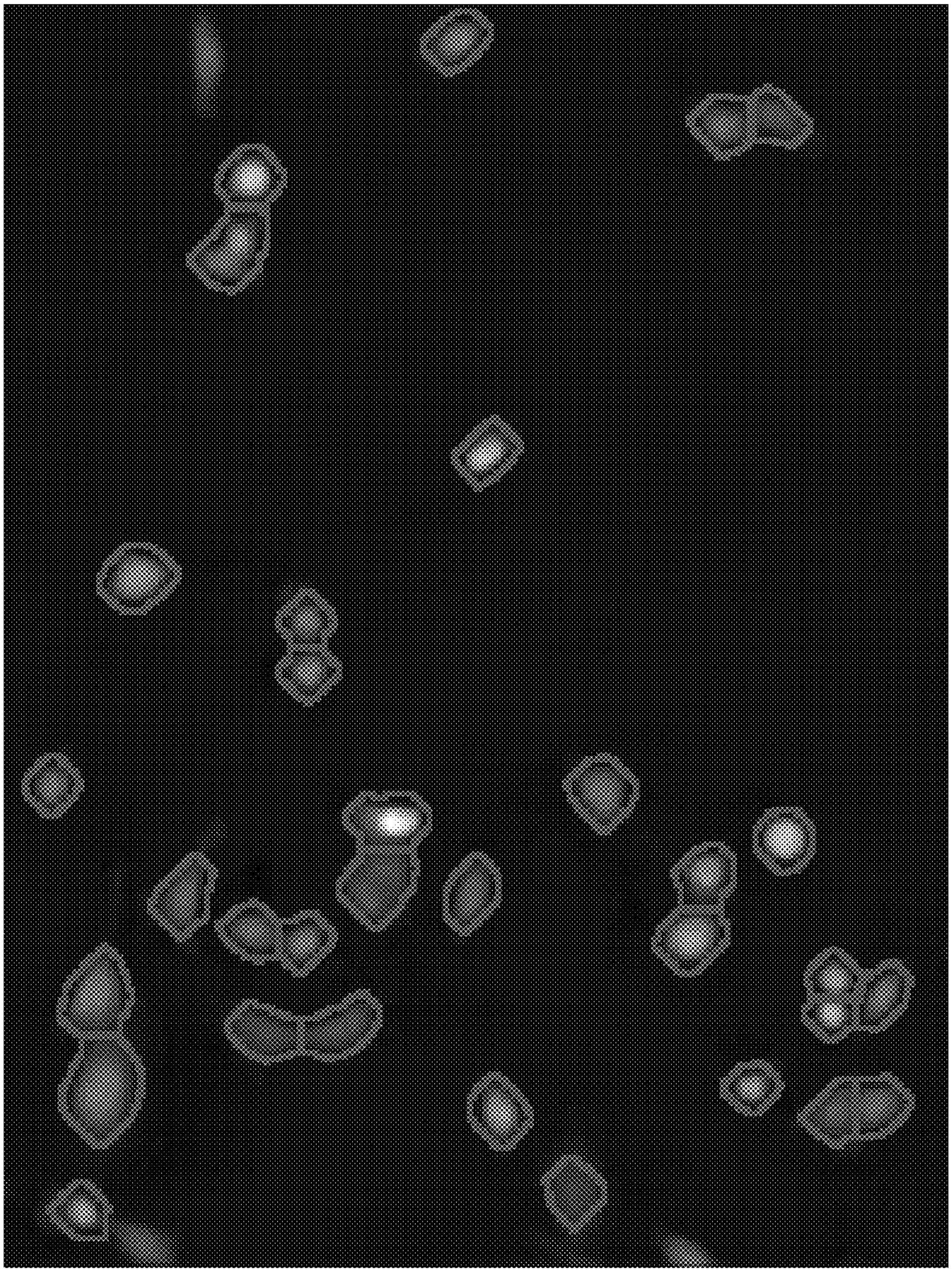
FIG. 16 shows images of cells after segmentation using interferometry based systems, according to embodiments of the present disclosure.

In some aspects, after background correction has been performed, segmentation may be performed using threshold techniques (e.g., pixel intensities above a threshold, such as 0.025) denotes a cell, and values below the threshold are non-cell regions based on n clustering of pixel intensities. Alternatively, machine learning techniques may be employed to perform segmentation. In FIG. 16, outlines of cell boundaries are shown. Thus, cell boundaries may be determined prior to determining the corresponding mass of the cells. For cells that may have adhered to one another, techniques such as the Watershed algorithm, may be used to separately track cells that are next to one another. FIG. 16 also shows clustering of cells, e.g., into groups of two and three cells that have been identified by such techniques.

FIG. 17 shows techniques for tracking individual cells as a function of time. As cell movement is random, cells may be treated as Brownian particles. The probability of a single cell moving a distance $\delta$ in time $\tau$ may be represented as:

$$P(\delta \mid \tau) = \frac{1}{4\pi D\tau} e^{-\frac{\delta^2}{4D\tau}}$$

(where D is mass diffusivity) and the probability of a population of N non-interacting particles may be represented as $$P(\{\delta_i\} \mid \tau) = \left(\frac{1}{4\pi D\tau}\right)^N \exp\left[\sum_{i=1}^{N} -\frac{\delta_i^2}{4D\tau}\right]$$

Techniques to track a population of cells typically involve large combinatronics analysis of ROIs in a frame, each having N! possible combinations at each time step. Additionally, this type of analysis may be complicated by close clustering of cells, linking tracks even when the region of interest (ROI) is lost/undetected for a period of time. Techniques for tracking populations of cells may utilize implementations of algorithms such as the Crocker and Grier algorithm with an input parameter list of a mass-weighted centroid, or scaled mass techniques that may differentiate between spatially similar neighbors, etc.

Figure 17A:
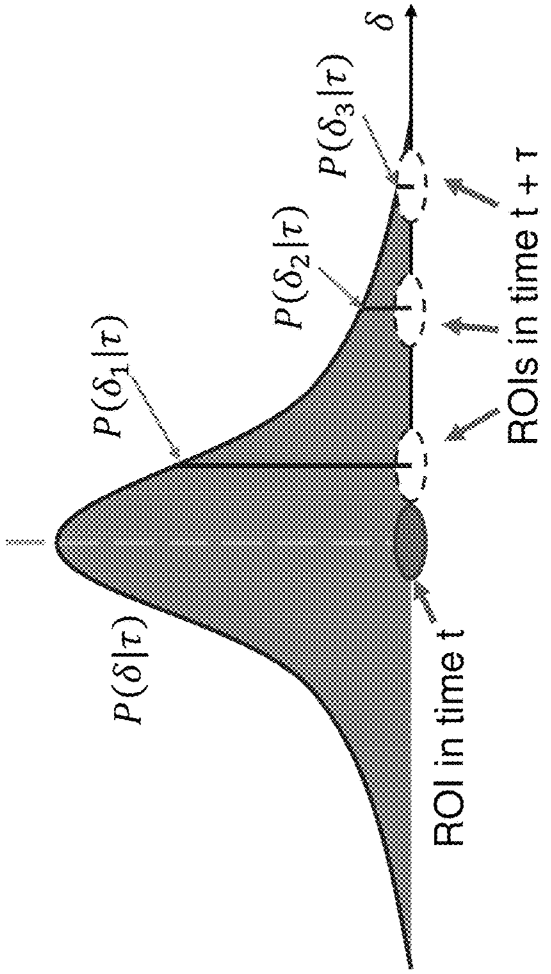
FIGS. 17A-17B show examples of objects tracked as a function of time using interferometry based systems, according to embodiments of the present disclosure.

FIG. 17A shows a probability distribution of tracking a single cell as a function of time. At time t, the cell is equally likely to move in any available trajectory, and is represented by a standard distribution. Various probabilities of a cell moving a distance $\delta$ in a time are shown, e.g., with a cell moving from $\delta_1$ to $\delta_2$ and to $\delta_3$ in times t+T.

Figure 17B:
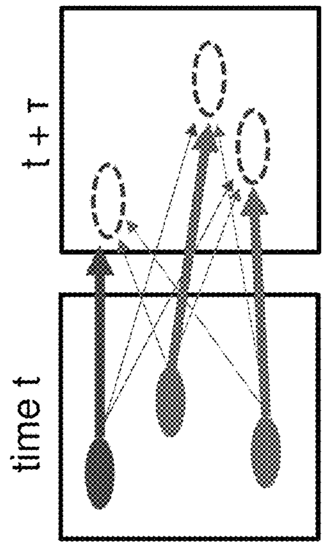

FIG. 17B shows extension of this technique to multiple cells as a function of time, allowing the trajectories of individual cells to be tracked as a function of time. By tracking cells as a function of time, mass calculations may be performed on the individual cells, providing a way to identify small mass changes in populations of cells.

Several tests have been developed to determine errors introduced by different subsystems, and determine overall system precision and accuracy. The overall error in the system is estimated to be <3%, and the system has the capability to image at least about 16 positions per minute (at least about 320 positions in 20 minutes).

Figures 18A, 18B, 18C, 18D, 18E:
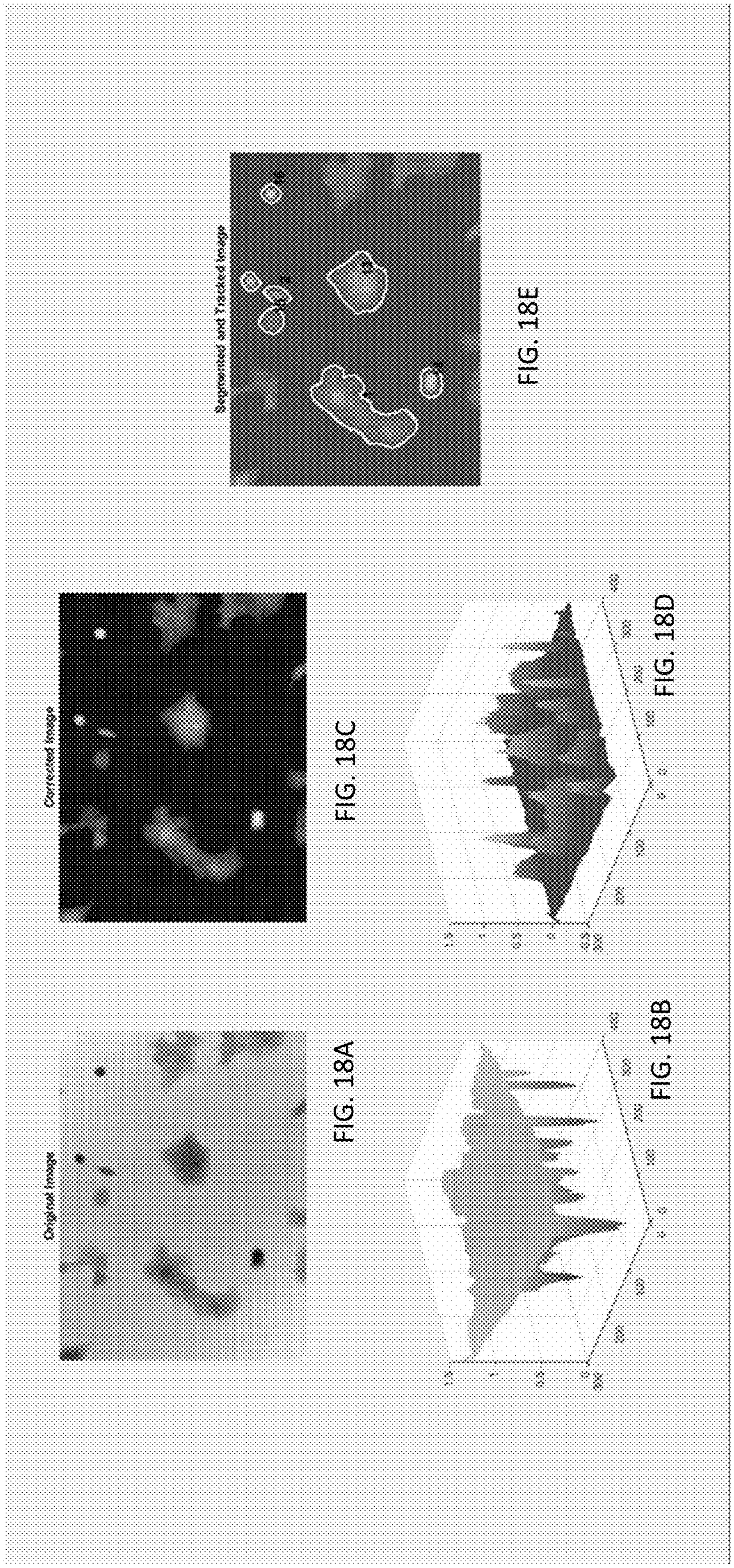
FIGS. 18A, 18B, 18C, 18D and 18E show images of cells tracked as a function of time and corresponding intensities using interferometry based systems, according to embodiments of the present disclosure.

FIGS. 18A-18E show a snapshot of a population of cells being monitored as a function of time. FIG. 18A shows a phase contrast image and FIG. 18B shows the corresponding brightness intensity plotted in 3D. In this image, cells appear darker than the surrounding medium, and therefore, decreases in pixel intensity indicate the regions of cells. Other types of non-fluorescent imaging techniques (e.g., DIC, bright-field, etc.) may similarly show a decrease in pixel intensity to indicate the presence of a cell, and similar techniques may be applied to these images.

FIG. 18C shows an image of the background corrected image of FIG. 18A. FIG. 18D shows the corresponding brightness intensity plotted in 3D. In the corrected image, cells appear brighter than the surrounding medium, and therefore, increases in pixel intensity indicate the regions of cells. FIG. 18E, a density plot of the phase delay of cells, shows a 2D plot of FIG. 18D.

Live Cell Interferometry for Screening Therapeutics

Some example techniques are provided herein to utilize interferometry systems (e.g., live cell interferometry (LCI) systems) to rapidly detect small changes in cell mass. U.S. Application No. 63/028,183 describes LCI systems comprising novel image processing techniques for detecting small changes in mass in individual object masses (e.g., cells) for a population of objects as a function of time.

In some aspects, an image or a portion of an image, may undergo an initial flattening process, in which the image or portion thereof is fit to a first function to generate an initial fitted function. In some aspects, the first function may be a polynomial. The initial fitted function (degree n) may be subtracted from the image, or a portion thereof, to generate a first approximation of a background subtracted image or a portion thereof.

In order to separate the background regions from the cellular regions, a clustering technique based on a k-means algorithm may be used to classify pixels of the image or portion thereof as background pixels or cellular pixels. After classification, the cellular pixels are excluded, and only the background pixels are fit to a second function (degree m) to generate a background fitted function. In some aspects, the second function is a higher order polynomial than the first function (e.g., m>n). The background fitted function is used to remove background noise from the image or portion thereof, leaving the intensity values for the cells. While the examples provided use polynomials, it should be appreciated that other types of functions (e.g., linear, exponential, logarithmic, sinusoidal, step-wise, custom, etc.) may also be useful depending on the nature of the physical geometry, optical properties, cell types, or other factors.

In general, for background correction, a function may be fit to the entire image, or a portion of the image (e.g., a region/area of the image, or a profile of the image such as a single row of pixels). For example, the background may be non-uniform along sides of the image, and therefore, it may be desirable to use different functions in different portions of the image to account for such non-uniformity. Thus, the present techniques are not to be limited and may be applied to any area of the image (e.g., a single row of pixels, regions of pixels, or the entire image).

These image processing techniques may also perform segmentation on cells to determine cell boundaries for cells that are alone or are in physical contact with other cells (e.g., clusters of cells which are adhered or proximal to each other).

In some aspects, the image processing techniques may track movement of cells as a function of time, and based on this information, may compute a corresponding cell mass as a function of time. In other aspects, the image processing techniques track individual movements of a population of cells as a function of time, and compute corresponding cell masses of the individual cells within the population as a function of time. In addition to movement, cells may have other parameters that could be tracked using image processing techniques, such as shape, size, circularity, etc. The image processing techniques may track sizes of cells, shapes of cells, circularity of cells, etc., in order to determine changes of these parameters over time, in order to determine cell mass as a function of time, etc. For example, the image processing techniques may track changes in the sizes of cells, combined with movement of the cells, to compute a corresponding cell mass as a function of time. In various implementations, statistical models may be used to track various cell parameters to compute mass of the cells. For example, statistical models may be developed based on historical cell parameters and corresponding cell masses.

The system may image an area (e.g., a 96 well plate) in an automated manner by taking images at specified positions along a trajectory. To perform this, the system comprises components to move the well plates or the microscope such that entire area may be imaged. The system moves to a designated position, performs an autofocus routine to bring the cells into focus, and then acquires an image. This process may repeated for every position along the trajectory. The process is repeated in order to generate a time series of images for each position along the trajectory. In various implementations, example automated routines described herein may increase throughput from 400 to 500 positions or more (e.g., in different wells of 96 well plates, etc.). This may improve the technology by allowing the system to monitor the effects of drugs on cancer samples at more positions in the wells. This may increase the number of cells that can be analyzed by the system relative to other systems, because example systems described herein may monitor more cells located at more positions, etc. In some embodiments, the system may perform a random position analysis to randomly select positions for image capture, to test the effects of the drugs on cancer samples randomly. In various implementations, a traveling salesman problem algorithm may be implemented to optimize the travel of the microscope among the various positions, to reduce the travel time for the microscope to traverse the wells and capture images at each position.

Any of the following therapeutics or combinations thereof may be screened using the LCI techniques provided herein. In some aspects, angiogenesis inhibitors such as lenalidomide, pomalidomide, and thalidomide or proteasome inhibitors such as bortezomib, carfilzomib, ixazomib may be screened. HDAC enzyme inhibitors may be screened as well as steroids including corticosteroids, dexamethasone, or prednisone. Panobinostat may also be screened.

It is also contemplated herein that LCI techniques may be used to screen monoclonal antibodies or other types of immunotherapeutics capable of targeting cancer cells or other cells for elimination. For example, monoclonal antibodies may bind to the cancer cell (e.g., elotuzumab, daratumumab, etc.) to trigger elimination of the cancer cell by antibody dependent cell cytotoxicity (ADCC). In other aspects, Fc fragments of antibodies may bind to and activate NK cells to target and eliminate cancer cells, to C1q for complement activation, or may trigger apoptosis by Fc cross-linking. Binding of Fab antibody fragments to cancer cells may also promote killing of the cancer cells by cytotoxic granules, or Fab antibody fragments may bind to CD38 to trigger cell elimination. Many variations of these techniques exist, and all are contemplated for use herein.

Interferometry Applications

The present techniques may be used to detect small mass changes in cells for any biological state or disease involving mass change. For example, the present techniques may be used to track increases or decreases in cell growth rates, to measure growth conditions (e.g., in different cell culture media), to measure effects of therapeutics on proliferation rates of cells (e.g., to select optimal therapeutics or combination thereof for cancer), to study subpopulations of cells with differing sensitivities to therapeutics, to measure rates of tissue regeneration and repair, to measure activation and proliferation of immune cells, to track cell-cell mediated elimination, and/or to monitor growth rates from mutant morphologies.

In some embodiments, the present techniques may be used to determine the effect of a particular chemotherapeutic or combination of chemotherapeutics to treat diseases, such as acute lymphoblastic leukemia, chronic lymphocytic leukemia, acute myeloid leukemia, chronic myeloid leukemia, lymphomas, etc. Other types of cancer cells may include, but are not limited to, acute lymphocytic leukemia, adenocarcinoma, AIDS-associated leukemias, adult T-cell leukemia lymphoma, basal cell carcinoma, biliary tract cancer, bladder cancer, blastoma, Bowen's disease, brain cancer, breast cancer, carcinoma, cervical cancer, choriocarcinoma, chronic myelogenous leukemia, colon cancer, colorectal cancer, endometrial cancer, esophageal cancer, fibrosarcoma, gastric cancer, gastrointestinal cancer, germ cell tumors, germinal tumors, glioblastoma, hairy cell leukemia, head and neck cancers, hematological neoplasms, hepatic carcinoma, hepatoma, Hodgkin's and non-Hodgkin's lymphoma, Hodgkin's disease, intraepithelial neoplasms, Kaposi's sarcoma, kidney cancer, leiomyosarcoma, leukemia, liposarcoma, liver cancer, lymphocytic lymphomas, medullar carcinoma, medulloblastomas, melanoma, Merkel cell carcinoma, mesenchymal cell cancers multiple myeloma, myelogenous leukemia, neuroblastomas, non-seminoma, non-small cell lung cancer, oral cancer, osteosarcoma, ovarian cancer, Paget's disease, pancreatic cancer, prostate cancer, rectal cancer, renal cancer, renal cell carcinoma, rhabdomyosarcoma, salivary gland carcinoma, sarcoma, seminoma, skin cancer, small-cell lung cancer, squamous cell carcinoma, stromal tumors, T-cell acute lymphoblastic leukemia/lymphoma, teratomas, testicular cancer, thyroid adenocarcinoma, thyroid cancer, vulval cancer, and Wilms' tumors.

Therapeutics

As used herein, a therapeutic refers to a molecule or composition that has an effect on a cell. In some aspects, the therapeutic has the capability to inhibit or reduce the growth of cancer or tumor cells, and preferably, is able to localize or accumulate in cancer or tumor cells in vivo. For example, the therapeutic may bind to a tumor cell or cancer cell, or may bind in the vicinity of a tumor cell or cancer cell. In other aspects, the therapeutic may activate and/or stimulate immune cells, may impact rates of cell growth, or otherwise impact the mass of the cell. In some aspects, the mass of the cell includes the cellular mass excluding water.

In general, any type of therapeutic may be screened for an effect using the present techniques, including, but not limited to, small molecule compounds (e.g., drugs, organic compounds, etc.) and other molecules (e.g., carbohydrates, glycolipids, glycoproteins, lipids, lipopolysaccharides, nucleic acids, phospholipids, proteoglycans, etc.). Therapeutics may also include proteins, peptides, or peptidomimetics.

As used herein, "polypeptide," "peptide," and "protein" are used interchangeably to refer to a polymer of amino acid residues linked by amide bonds that may include natural and non-natural amino acids. Other examples of therapeutics may include antibodies or fragments thereof, checkpoint inhibitors, NK cells, or chimeric T cells, etc.

In other aspects, the therapeutic may bind to an antigen on the surface of the cancer or tumor cell, or may bind to other cells or extracellular components present in the tumor or cancer environment (e.g., fibroblasts, endothelial cells, extracellular matrix, etc.). In some embodiments, the therapeutic may bind to an intracellular target that becomes accessible to the cancer targeting molecule upon apoptosis or necrosis of the cancer cell. Cancer or tumor cells undergoing necrosis or apoptosis often have a porous plasma membrane, thereby allowing access to intracellular targets. Alternatively, some cancer targeting molecules, which are internalized by cancer cells, are able to bind to intracellular portions of cells that do not have a porous or defective plasma membrane (see, Porkka et al., Proc Natl Acad Sci USA. (2002) 99(11): 7444-9).

Screening

In some aspects, well plates may be used to test various therapeutics or combinations of therapeutics. In some aspects, a well plate with any suitable dimensions may be used, including, but not limited to, a 12 well plate, a 24 well plate, a 48 well plate, a 96 well plate, etc. In some aspects, each well may contain a different therapeutic. In other aspects, the wells may be grouped, such that each group of wells contain the same therapeutics. In still other aspect, each well may contain a combination of therapeutics (two or more). In other aspects, the wells may be grouped, and each group may contain a combination of therapeutics (two or more).

In still other aspects, each well may contain a different concentration of a therapeutic. In some aspects, the concentrations may range from 0.01 nM up to 100 mM, from 0.01 nM up to 1 mM, from 0.01 nM up to 100 μM, from 0.01 nM up to 100 nM, or from 0.02 nM up to 40 nM. For example, in one aspect, concentrations may include a titration, such as 0.04 nM, 0.15 nM, 0.62 nM, 2.5 nM, 10 nM, 40 nM, allowing a minimum concentration of the therapeutic to be determined. In other aspects, multiple therapeutics may be present, with each well containing a different concentration of one or more therapeutics. For example, in some aspects, a first therapeutic may be kept at a constant concentration while the concentration of a second therapeutic may be varied or vice versa.

In some aspects, the well plates may be manufactured using different materials with different optical characteristics, and having different optical clarities for distortion free images. Materials may include but are not limited to: polystyrene, polyolefin acrylate, polypropylene, polyethylene, polycarbonate, etc.

In general, any suitable cell line may be used. For cancer studies, the cell is from a cancer line, derived from a cancer cell line, is a model or mimic of a cancer cell line, or is a cell with characteristics similar to a cancer cell line. For example, cell lines such as H929, MM.1S, HeLa, KB, HER2+, MDA-231, MCF7, HCC, NCI, etc. are suitable with the techniques provided herein.

In some aspects, various types of media may be formulated, and the present techniques may be used to validate the performance of the media relative to the control media or accepted media.

Machine Learning Applications

Machine learning/artificial intelligence techniques may be used for various aspects of biological image analysis. As referenced herein, it is understood that the term "machine learning" refers to artificial intelligence systems configured to learn from data without being explicitly programmed. Such systems are understood to be necessarily rooted in computer technology, and in fact, cannot be implemented, or even exist, in the absence of computing technology. While machine learning systems may utilize various types of statistical analyses, machine learning systems are distinguished from statistical analyses by virtue of their ability to learn without explicit programming, and such systems are reliant upon computing technology.

Machine learning techniques may be used to classify cells as sensitive or resistant to a particular therapeutic. In this example, a set of patient samples with clinical outcomes may be used to create a training data set with which to train the machine learning model to classify cells as sensitive or resistant to a therapeutic. The classifier may identify, in a heterogeneous population, correlations between cell features and corresponding drug resistance (e.g., by determining that smaller and more eccentric subpopulations within a heterogeneous population tend to be more resistant).

Machine learning techniques may be used to automatically determine cell killing. For example, typical features of a cell to cell killing event include proximity of two cells with a subsequent sharp increase in the mass of one cell and a decrease in mass of the other cell. Such patterns may be identified by the machine learning model.

Machine learning techniques may be used to automatically determine a non-target population of cells (e.g., NK cells, NK-92 cells, T cells, etc.) and a target population of cells in a label-free manner. For example, NK cells may be automatically recognized in a population of cells, as these cells persist, while target cells do not. Thus, labels are not needed to identify target cells.

Any suitable machine learning algorithm (e.g., support vector machine, neural network, decision tree, random forest, deep learning neural network, logistic regression, etc.) may be used for classifying sensitive vs resistant cells, for automated determination of cell killing, for cell-cell interactions of effector and target cells, etc. Techniques for training machine learning models are known in the art, and may include providing a training data set with which to train the model. Once the model is trained, the model may be tested on other data (e.g., in which the outcome is known), and the performance of the model may be evaluated. This process may be repeated until meeting desired performance metrics. In other aspects, unsupervised training may be performed.

The machine learning engine may create a trained model as a function of the training data, and optionally, input(s) from the user. Once trained, the trained model will have one or more model parameters or metrics that describe the trained model (e.g., accuracy, accuracy gain, sensitivity, sensitivity gain, performance metrics, weights, learning rate, epochs, kernels, number of nodes, number of layers, etc.).

Machine learning algorithms may include different types of algorithms including implementations of a classification algorithm, a neural network algorithm, a regression algorithm, a decision tree algorithm, a clustering algorithm, a genetic algorithm, a supervised learning algorithm, a semi-supervised learning algorithm, an unsupervised learning algorithm, a deep learning algorithm, or other types of algorithms. More specifically, machine learning algorithms can include implementations of one or more of the following algorithms: a support vector machine, a decision tree, a nearest neighbor algorithm, a random forest, a ridge regression, a Lasso algorithm, a k-means clustering algorithm, a boosting algorithm, a spectral clustering algorithm, a mean shift clustering algorithm, a non-negative matrix factorization algorithm, an elastic net algorithm, a Bayesian classifier algorithm, a RANSAC algorithm, an orthogonal matching pursuit algorithm, bootstrap aggregating, temporal difference learning, backpropagation, online machine learning, Q-learning, stochastic gradient descent, least squares regression, logistic regression, ordinary least squares regression (OLSR), linear regression, stepwise regression, multivariate adaptive regression splines (MARS), locally estimated scatterplot smoothing (LOESS) ensemble methods, clustering algorithms, centroid based algorithms, principal component analysis (PCA), singular value decomposition, independent component analysis, k nearest neighbors (kNN), learning vector quantization (LVQ), self-organizing map (SOM), locally weighted learning (LWL), apriori algorithms, eclat algorithms, regularization algorithms, ridge regression, least absolute shrinkage and selection operator (LASSO), elastic net, classification and regression tree (CART), iterative dichotomiser 3 (ID3), C4.5 and C5.0, chi-squared automatic interaction detection (CHAID), decision stump, M5, conditional decision trees, least-angle regression (LARS), naive Bayes, Gaussian naive Bayes, multinomial naive Bayes, averaged one-dependence estimators (AODE), Bayesian belief network (BBN), Bayesian network (BN), k-medians, expectation maximisation (EM), hierarchical clustering, perceptron back-propagation, Hopfield network, radial basis function network (RBFN), deep Boltzmann machine (DBM), deep belief networks (DBN), convolutional neural network (CNN), stacked auto-encoders, principal component regression (PCR), partial least squares regression (PLSR), Sammon mapping, multidimensional scaling (MDS), projection pursuit, linear discriminant analysis (LDA), mixture discriminant analysis (MDA), quadratic discriminant analysis (QDA), flexible discriminant analysis (FDA), bootstrapped aggregation (bagging), adaboost, stacked generalization (blending), gradient boosting machines (GBM), gradient boosted regression trees (GBRT), random forest, etc. Training may be supervised, semi-supervised, or unsupervised.

The machine learning model may be a dynamic model that is updated (e.g., periodically or on a continuous basis). In some embodiments, the trained model is updated in real-time, on a daily, weekly, bimonthly, monthly, quarterly, or annual basis. For example, as new information is made available, the learning model may be further updated. In such cases, the learning model may comprise metadata that describes the state of the learning model with respect to its updates, such as one or more of the following: a version number, date of update, amount of new data used for the update, shifts in model parameters, convergence requirements, or other information. Such information provides for managing large collections of models over time, where each learning model may be treated as a distinct manageable object.

The therapeutics described herein may be administered in any suitable combination, and may be combined with surgery and radiation therapy. Therapeutics may include any chemotherapeutic or other molecule for the treatment of cancer, including, but not limited to: 4-demethoxy-daunomycin, aminopterin, arsenic trioxide, azacitidine, azathioprine, bleomycin, canninomycin, capecitabine, carboplatin, chlorambucil, cholchicine, cisplatin, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitomycin C, mitoxantrone, oxaliplatin, paclitaxel, pemetrexed, teniposide, tiguanine, valrubicin, vinblastine, vincristine, vindesine, and vinorelbine. Additional examples of therapeutics include but are not limited to anthracyclines (e.g., daunorubicin, doxorubicin, epirubicin), anti-folates (e.g., methotrexate, pemetrexed), anti-microtubule agents (e.g., taxanes such as docetaxel, paclitaxel), antitumor antibiotics (e.g., bleomycin, mitomycin), aziridines (e.g., mytomycin, thiotepa), deoxynucleoside analogs (e.g., cytarabine, decitabine, gemcitabine), fluoropyrimidines (e.g., capecitabine, fluorouracil), nitrogen mustards (e.g., chlorambucil, cyclophosphamide), nitrosoureas (e.g., carmustine, n-nitroso-n-methylurea, semustine), platinum-based antineoplastic agents (e.g., carboplatin, cisplatin, neoplatin, oxaliplatin, platamin), tetrazines (e.g., dacarbazine, mitozolimide), thiopurines (e.g., mercaptopurine, thioguanine), topoisomerase inhibitors (e.g., doxorubicin, etoposide, mitoxantrone, teniposide), etc. The administration of various chemotherapeutic agents is described in the “Physicians’ Desk Reference” (PDR), e.g., 1996 edition (Medical Economics Company, Montvale, N.J. 07645-1742, USA).

Methods of Administration

The techniques provided herein may be used to identify an optimal therapeutic or combination thereof, for a biological effect (e.g., the treatment of cancer in an individual in need thereof).

In some aspects, the techniques provided herein may be used to select an optimal therapeutic treatment from among a population of therapeutics. For cancer, a therapeutic may be screened (e.g., for reducing the size of or inhibiting the growth of or inhibiting the metastasis of cancer cells or tumor cells are provided herein), wherein an effective amount of the therapeutic is administered to a patient in need thereof. Typically, the therapeutic will localize to the site of the cancer cells or tumor, and will not accumulate in normal non-diseased tissue.

As employed herein, the phrase “an effective amount,” refers to a dose of a therapeutic sufficient to provide concentrations high enough to impart a beneficial effect on the recipient thereof. The specific therapeutically effective dose level for any particular subject will depend upon a variety of factors including the disorder being treated, the severity of the disorder, the activity of the specific therapeutic, the route of administration, the rate of clearance of the therapeutic, the duration of treatment, the drugs used in combination or coincident with the therapeutic, the age, body weight, sex, diet, and general health of the subject, and like factors well known in the medical arts and sciences. Various general considerations taken into account in determining the “therapeutically effective amount” are known to those of skill in the art and are described (e.g., in Gilman et al., eds., Goodman And Gilman’s: The Pharmacological Bases of Therapeutics, 8th ed., Pergamon Press, 1990; and Remington’s Pharmaceutical Sciences, 17th ed., Mack Publishing Co., Easton, Pa., 1990). Dosage levels typically fall in the range of about 0.001 up to 100 mg/kg/day; with levels in the range of about 0.05 up to 10 mg/kg/day are generally applicable.

A therapeutic can be administered parenterally, such as intravascularly, intravenously, intra-arterially, intramuscularly, subcutaneously, or the like. Administration can also be orally, nasally, rectally, transdermally, or via inhalation of an aerosol. The therapeutic may be administered as a bolus, or slowly infused.

A therapeutically effective dose can be estimated initially from cell culture assays by determining an $IC_{50}$ or $EC_{50}$. A dose can then be formulated in animal models to achieve a circulating plasma concentration range that includes the $EC_{50}$ or $IC_{50}$ as determined in cell culture. Such information can be used to more accurately determine useful doses in humans. Levels in plasma may be measured, for example, by HPLC. The exact formulation, route of administration, and dosage can be chosen by the individual physician in view of the patient's condition.

It should be apparent to those skilled in the art that many more modifications besides those already described are possible without departing from the concepts provided herein. In interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of an element selected from the group consisting of elements A, B, C . . . and N, the text should be interpreted as requiring only one element from the group, not A plus N, or B plus N, etc.

Further Example Embodiments

Embodiment 1. A method of detecting mass changes of cells, wherein the cells are on a surface, comprising: exposing a first group of cells to a control condition and a second group of cells to a non-control condition; measuring masses of individual cells in the first group and in the second group using live cell interferometry (LCI) as a function of time; determining an aggregate mass for the first group and an aggregate mass for the second group; and determining whether the aggregate mass of the second group has decreased relative to the aggregate mass of the first group for the time series, wherein the cells are optionally in wells of a well plate.

Embodiment 2. The method of Embodiment 1, wherein the cells are cancer cells and the non-control condition comprises a compound capable of inhibiting cancer growth.

Embodiment 3. The method of Embodiment 1 or Embodiment 2, further comprising determining whether the aggregate mass of the second group has decreased relative to the aggregate mass of the first group within four to twelve hours.

Embodiment 4. The method of any one of the previous embodiments, wherein the non-control condition comprises a chemotherapeutic, and further comprising: identifying using LCI at least two subpopulations of cells, wherein a first subpopulation is sensitive to the chemotherapeutic and a second population is resistant to the chemotherapeutic.

Embodiment 5. The method of any one of the previous embodiments, wherein the first group comprises at least one thousand cells and the second group comprises at least one thousand cells.

Embodiment 6. The method of any one of the previous embodiments, further comprising: partitioning the second group of cells into a plurality of subgroups, and exposing each subgroup to a different non-control condition, each non-control condition comprising at least one therapeutic; measuring masses of individual cells in the first group and in each subgroup in each image of the time series; determining an aggregate mass for the first group and an aggregate mass for each subgroup; and determining whether the aggregate mass of each subgroup has decreased relative to the aggregate mass of the first group for the time series.

Embodiment 7. The method of any one of the previous embodiments, wherein the cells are multiple myeloma cancer cells (optionally H929 cells or MM.1 cells), breast cancer cells, lung cancer cells, leukemia cells, or lymphoma cells, and optionally wherein the cells are patient-derived cells.

Embodiment 8. The method of any one of the previous embodiments, wherein the non-control condition comprises at least one therapeutic, and wherein the at least one therapeutic is a small molecule, a protein, an antibody or fragment thereof, a NK cell, or a CAR T cell.

Embodiment 9. The method of any one of the previous embodiments, wherein the non-control condition comprises immune cells and wherein the second group of cells expresses a surface ligand to which the immune cells bind, and wherein the non-control condition optionally comprises a compound capable of activating the immune cells.

Embodiment 10. The method of any one of the previous embodiments, further comprising using machine learning to classify the cells into a first subpopulation of cells sensitive to a therapeutic and into a second population of cells resistant to a therapeutic.

Embodiment 11. The method of any one of the previous embodiments, further comprising using machine learning to identify immune cells that eliminate target cancer cells, and optionally wherein up to twenty eight conditions are tested in triplicate within four to twelve hours.

Embodiment 12. A method of detecting mass changes in cells, wherein the cells are on a surface, comprising: exposing a first group of cells to a control media condition and a second group of cells to a non-control media condition; measuring masses of individual cells in the first group and in the second group using live cell interferometry (LCI) for a time series; determining an aggregate mass for the first group and an aggregate mass for the second group; and determining whether the aggregate mass of the second group has increased or remained about the same relative to the aggregate mass of the first group for the time series.

Embodiment 13. The method of Embodiment 12, wherein the control media condition comprises an additive (e.g., a surfactant, a detergent, or poly-D-lysine) and the non-control media does not comprise an additive.

Embodiment 14. A method of determining mass changes of cells comprising: obtaining a time series of images comprising one or more cells using live cell interferometry (LCI), wherein the cells are contained within one or more wells of a well plate, and wherein the system automatically images each well at predefined positions of a trajectory; for each position of the trajectory, determining masses of individual cells as a function of time comprising: performing background correction on the images corresponding to the position by fitting only the background pixels of each image to a polynomial function to generate a background fitted function, and subtracting the background fitted function from the image to generate a background corrected image; performing segmentation on background corrected images to resolve boundaries of the one or more cells; and determining respective masses of the one or more cells.

Embodiment 15. The method of Embodiment 14, further comprising: determining, for each position of the trajectory, an aggregate mass based on the respective masses; and/or determining whether aggregate masses of the cells in non-control conditions are increasing or decreasing relative to aggregate masses of the cells in control conditions.

Example 1. Screening Multiple Myeloma Samples to Identify Optimal Therapeutic(s) for Treatment The following examples pertain to various applications and are not intended to be limiting.

Multiple myeloma arises from abnormal proliferation of mutated plasma cells in a patient's bone marrow. Every year in the US, about 30,000 new cases are diagnosed, with about a 42% mortality rate. Biological markers for mutated cells include $CD138^+$ and $CD319^+$ for mutated plasma cells.

Treatments for hematopoietic disorders include radiofrequency thermal ablation of the diseased cells, followed by a stem cell transplant to replenish with normal cells. Additionally, a variety of drugs may be used, including, but not limited to, bortezomib, carfilzomib, corticosteroids, proteasome inhibitors, and xazomib. Selection of such treatments are largely trial-and-error based on individual patient symptoms, and different treatments may be selected based on the age of the patient (e.g., for ages under 65 or over 65).

The present techniques, which include LCI, may be used to guide clinical treatment by determining one or more therapeutic(s) that the patient's multiple myeloma cancer cells are most sensitive to.

An example protocol may include extracting bone marrow from a patient via a biopsy. The extracted bone marrow cells may be enriched for CD138 and grown (e.g., in a 96 well plate). The desired therapeutic or combination of therapeutics may be added to the individual wells to test efficacy of various therapeutic(s) on the enriched cells. Such techniques are described in the literature (see, Silva, Ariosto, et al. "An ex vivo platform for the prediction of clinical response in multiple myeloma." *Cancer research,* 77(12): 3336-3351, (2017)). LCI may be used to obtain images of the cells, and the images may be analyzed to determine the effect of the therapeutic(s). Based on the novel LCI techniques described herein, the total imagining time may be reduced from days or weeks to hours (e.g., about 4-24 hours, about 8 to 16 hours, etc.), providing a fast and effective way to identify optimal therapeutic(s) for a particular cancer obtained from a particular patient.

A typical assay may include, for a single plate, forming groups of seven wells. A range of concentrations may be used, with each concentration (e.g., a DMSO control, varying therapeutic concentrations of 0.039 nM, 0.156 nM, 0.625 nM, 2.5 nM, 10 nM, and 40 nM) applied to a group of wells. In some embodiments, cells are plated, therapeutic (s) are added, and images are collected every 10-15 minutes for the designated period of time.

For development of screening techniques, H929 cells may be used. H929 cells, which may be grown in serum free conditions, have the morphologic, ultrastructural, biochemical, immunologic, and cytochemical features of plasma cells (see, Gazdar et al., Blood (1986) 67(6): 1542-9). H929 cells, derived from a human patient with multiple myeloma, are commonly used for multiple myeloma testing and are sensitive to a variety of chemotherapeutic drugs.

Figure 19:
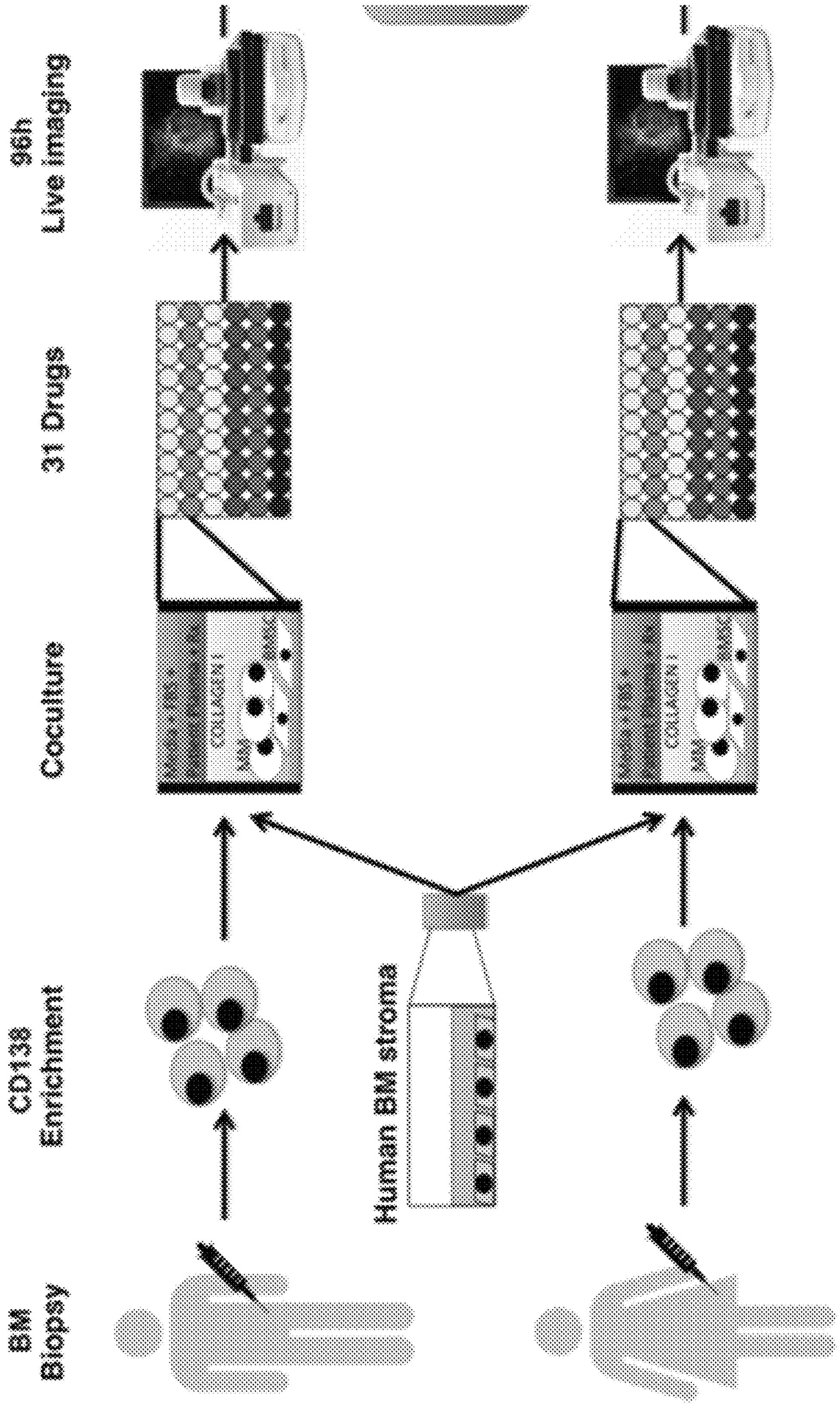
FIG. 19 shows an example protocol for screening therapeutics using live cell interferometry to determine one or more optimal therapeutics for treating a particular cancer, according to embodiments of the present disclosure.

As an alternative, MM.1 cells may be used as model cell line for assay development, wherein MM.1S refers to a strain that is sensitive to a drug such as dexamethasone and MM.1R refers to a strain that is resistant to a drug such as dexamethasone. For these types of experiments, a 12 well plate may be seeded at about $1.5\times\times10^5$ cells per plate. The desired concentration of therapeutic(s) may be added to each of the six wells. Control wells may also be established using the same dilutions with DMSO as the test well containing drug. LCI imaging may begin immediately after drug addition, with images being taken every 10-15 minutes. FIG. 19 shows an example protocol for screening therapeutic(s) using LCI to determine one or more optimal therapeutic(s) for a particular cancer. In this example, a bone marrow sample may be obtained from a patient. The sample may be enriched for cells expressing CD138, and cultured under suitable conditions (e.g., media, FBS, patient plasma, drug, etc.). The cells may be tested using different drugs or combinations of drugs, and imaging may be performed using LCI techniques. For example, for a 96 well plate, 31 different drugs or combinations thereof may be tested (with an n=3).

Example 2. Screening of H929 Cells

Figure 20A:
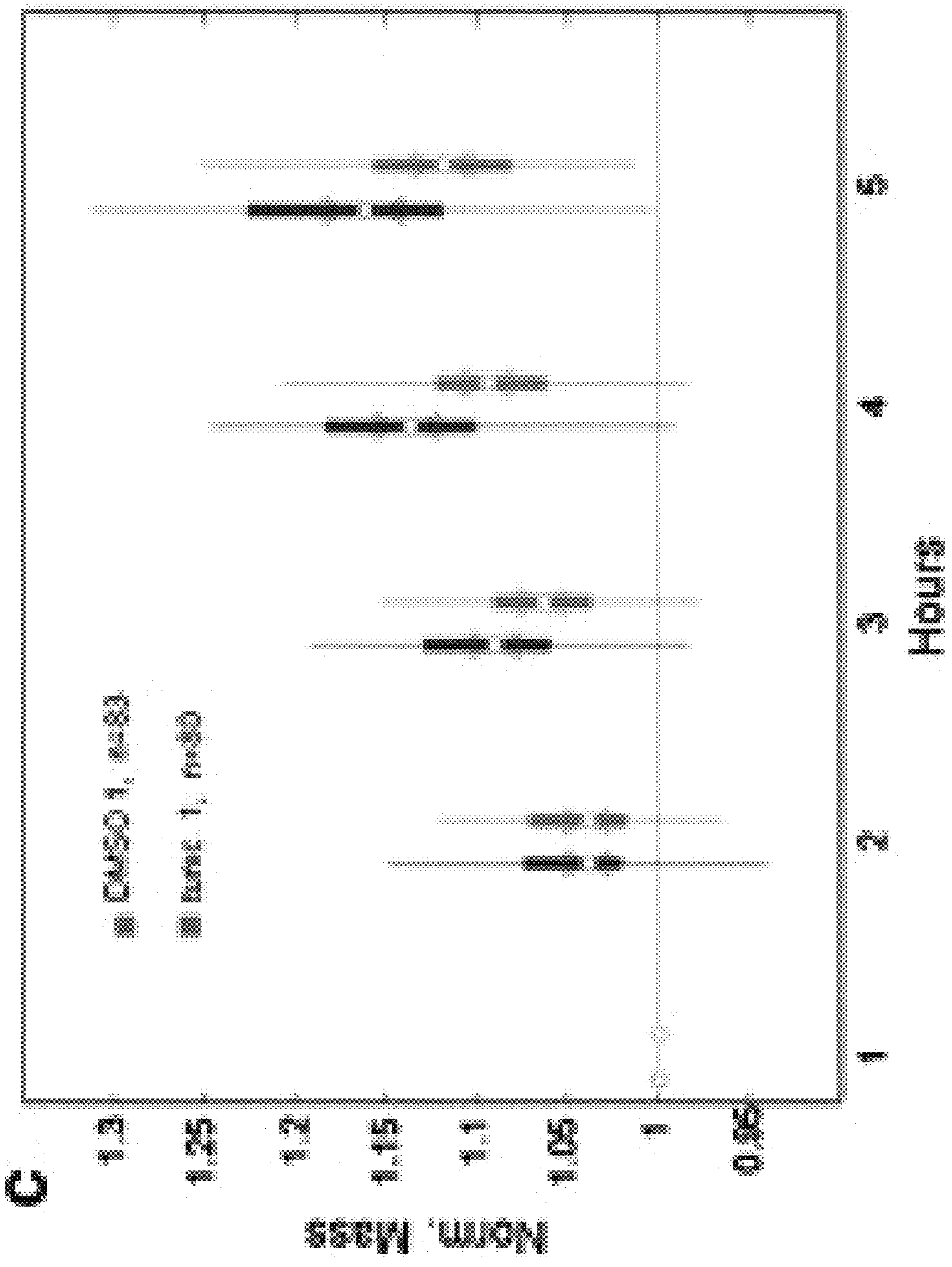
FIGS. 20A-20B show growth for H929 cells as a function of time, according to aspects of the present disclosure.

FIG. 20A shows cell growth as a function of time. Here, normalized mass is plotted versus time (in hours) of cells in DMSO (control) and treated cells. As shown by the graph, the mass of treated cells declines as a function of time relative to the control cells.

Figure 20B:
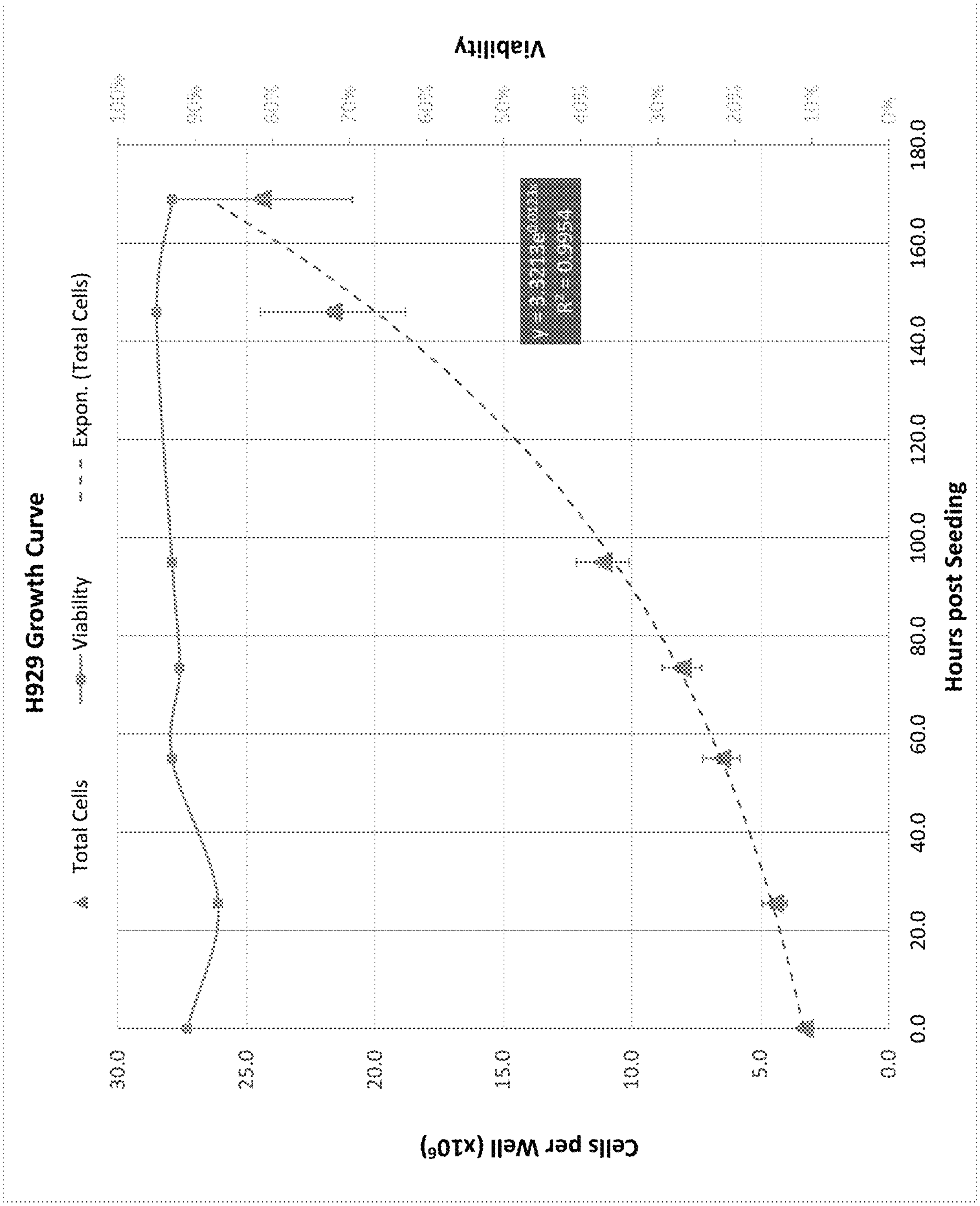

FIG. 20B shows a growth curve of H929 cells, where the time needed to reach viability is about 150 hours after initial culture using traditional techniques.

Figure 21A:
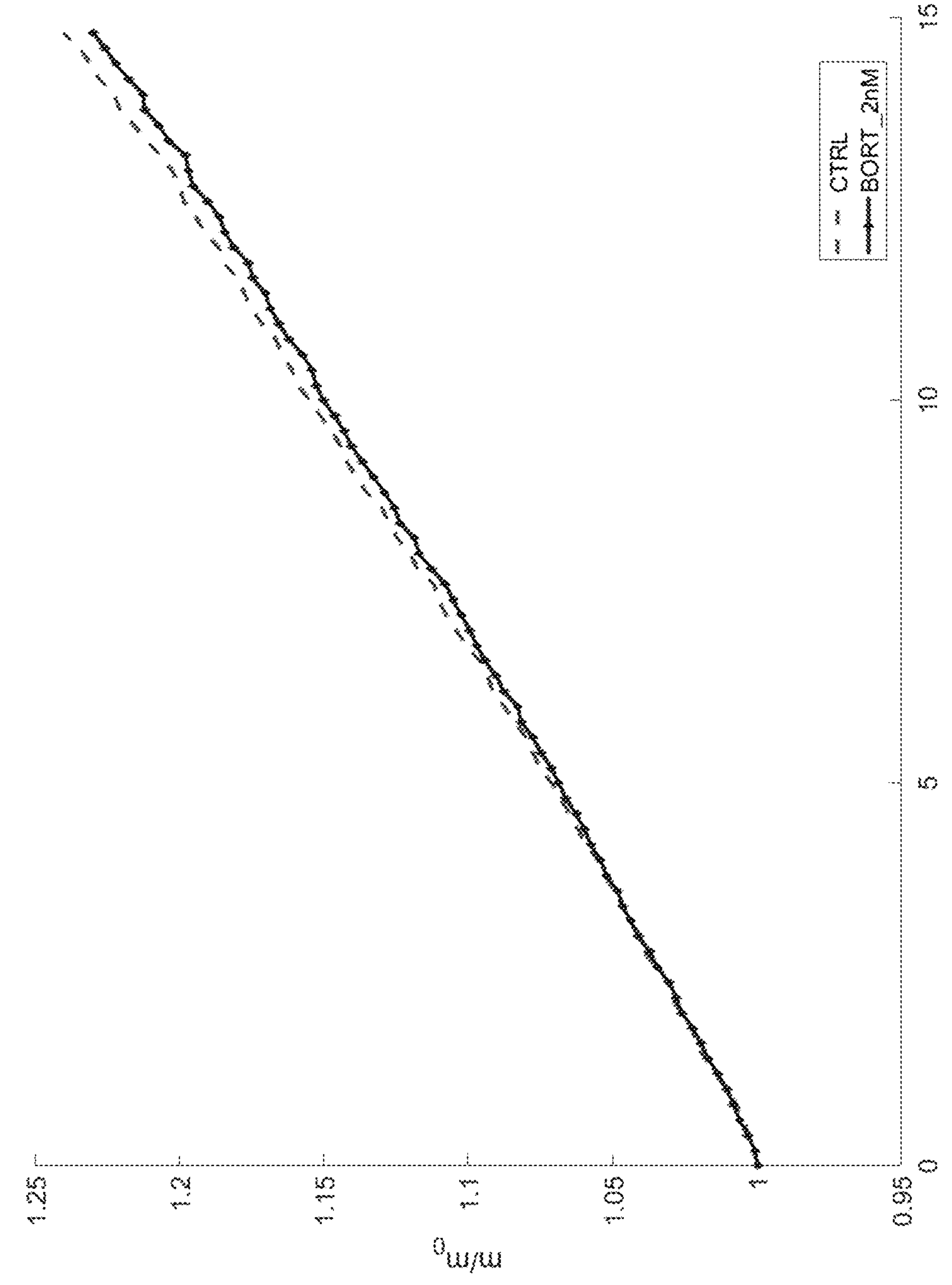
FIGS. 21A, 21B, 21C, 21D, 21E and 21F show growth of H929 cells with or without bortezomib, according to aspects of the present disclosure.

FIG. 21A shows analysis of H929 cells treated with 2 nM of bortezomib. In this experiment, about 1681 control cells and about 1272 bortezomib treated cells were screened.

Figure 21B:
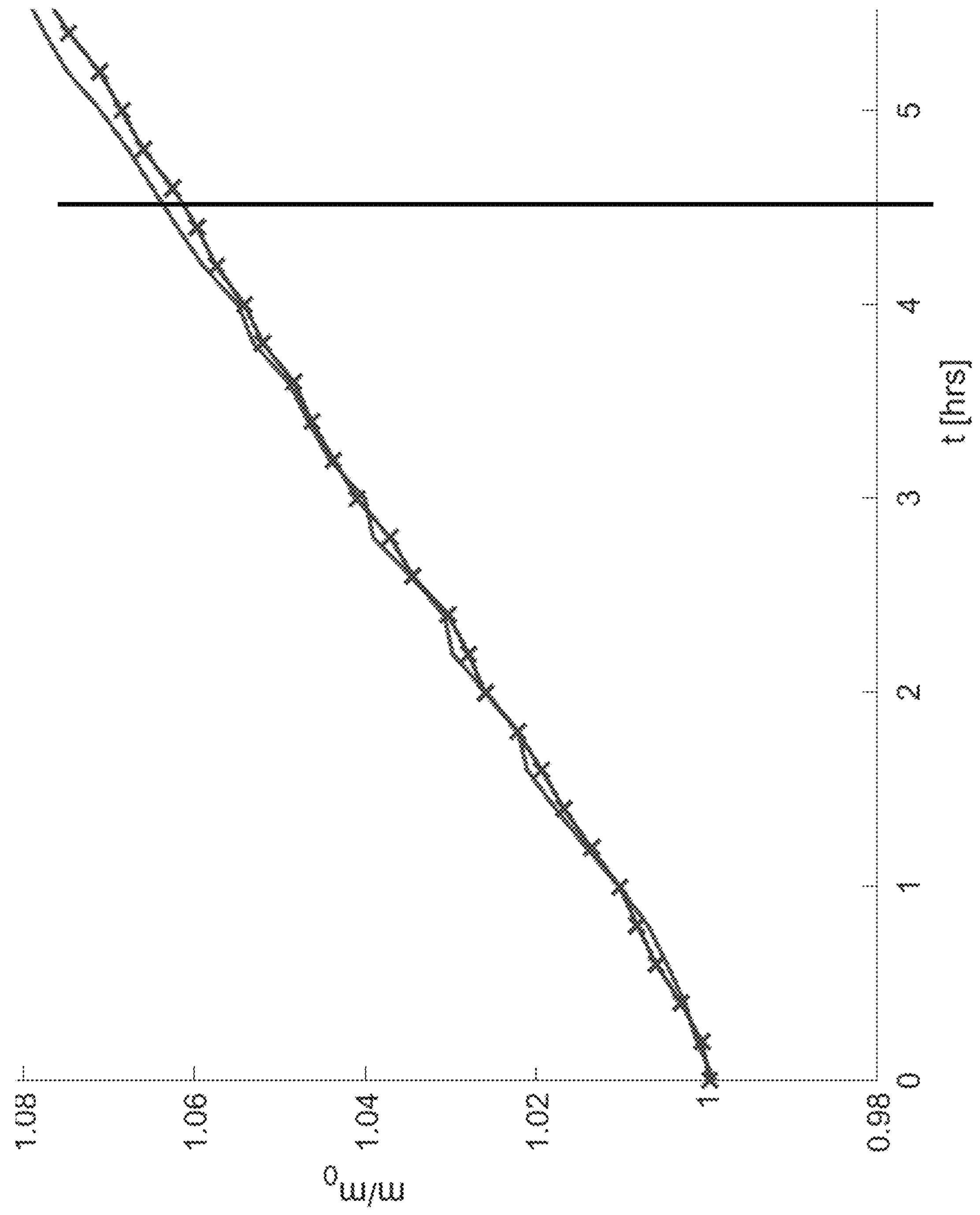

In this study, the normalized growth rate [1/h] of DMSO control cells was 0.0185, while the normalized growth rate [1/h] of 2 nM bortezomib treated cells was 0.0172, for a difference of −6.55% between these two growth rates. A small but statistically significant difference in growth rate was detected at about 4.5 hrs. FIG. 21A shows a normalized growth rate of control and 2 nM bortezomib treated cells over the course of about 15 hours. As shown in this graph, the growth trajectories of the control and bortezomib treated cells begin to diverge between 4-5 hours. FIG. 21B shows a close up of the trajectories of control and bortezomib treated cells (2 nM). Here, a vertical line indicates a statistically significant point of divergence using LCI techniques between 4-5 hours.

Figure 21C:
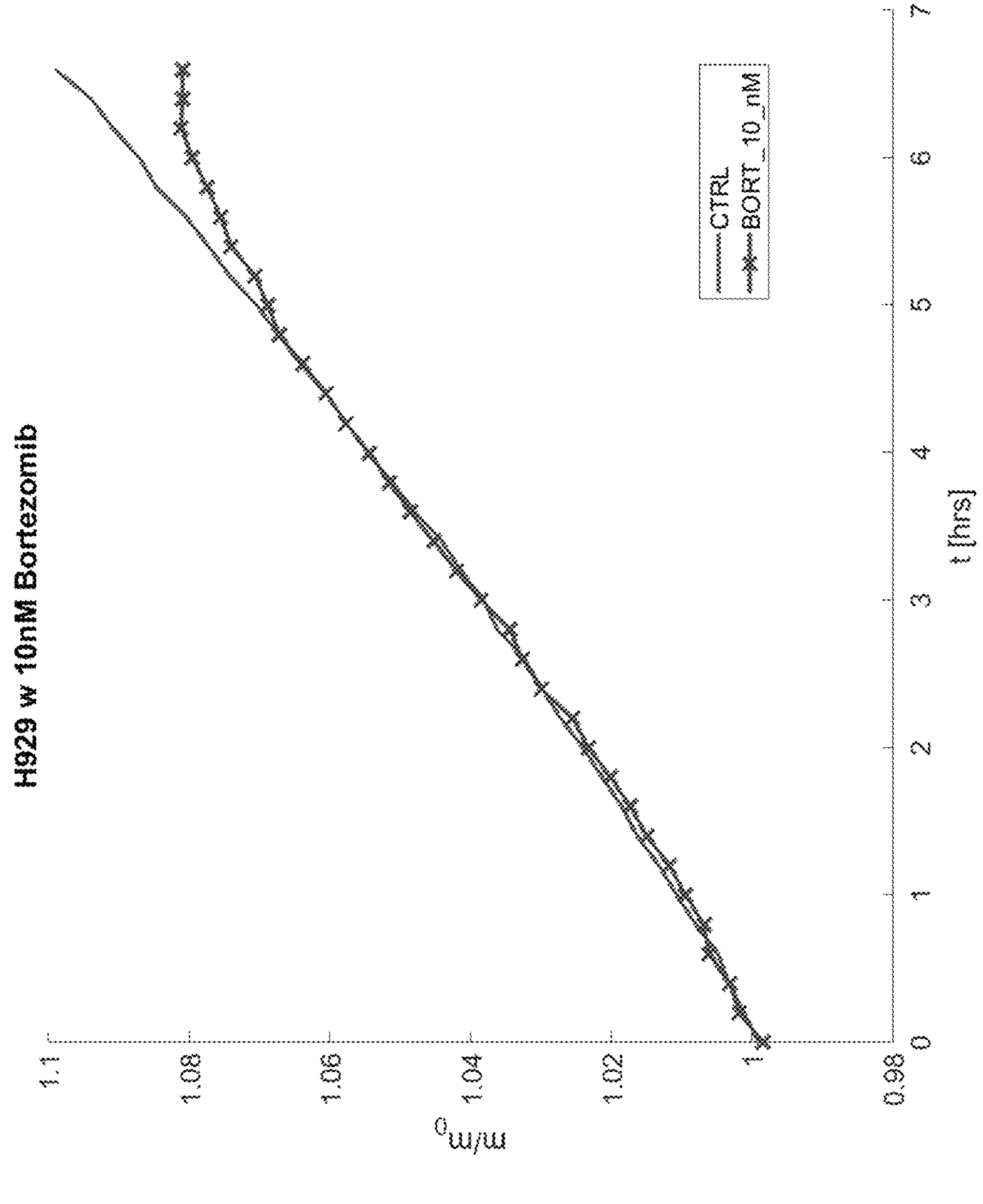

FIG. 21C shows analysis of H929 cells treated with 10 nM of bortezomib over the course of about seven hours. In this experiment, about 1889 control cells and about 1248 bortezomib treated cells were screened. Imaging was initiated after drug addition, every 12 min for 7 hrs. In this study, the normalized growth rate [1/h] of DMSO control cells was 0.0152, while the normalized growth rate [1/h] of 10 nM bortezomib treated cells was 0.0139, for a difference of −8.6% between these two growth rates. As shown by the graph, after about 5 hours, the normalized growth rate of control and 10 nM bortezomib treated cells diverged. Accordingly, under these conditions, efficacy of a drug was determined in about 5 hours.

Figure 21D:
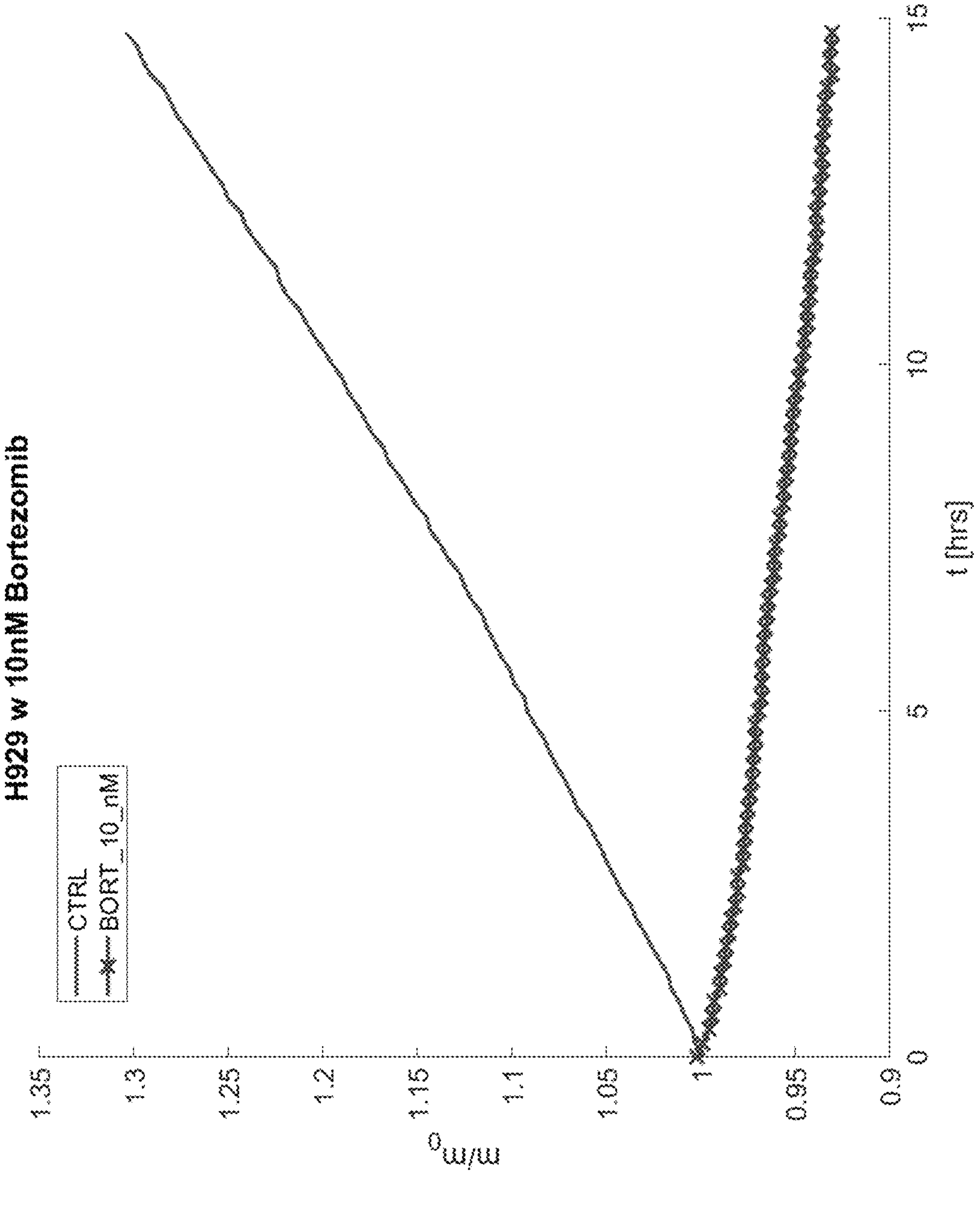

FIG. 21D shows growth rates of bortezomib treated cells and control cells. For this graph, the same plate (as used in FIG. 21C) was imaged (for a total of 24 hours) after drug addition. An image was taken every 12 minutes for about 15 hours. About 1867 control cells and about 1426 bortezomib treated cells were screened. In this study, the normalized growth rate [1/h] of DMSO control cells was 0.0226, while the normalized growth rate [1/h] of 10 nM bortezomib treated cells was 0.000443, for a difference of −119.6% between these two growth rates. FIGS. 21C and 21D show that for a plate imaged about 24 hours, the effects of the drug appear after 5 hours, and the growth rate continues to decrease throughout the next 16 hours.

Figure 21E:
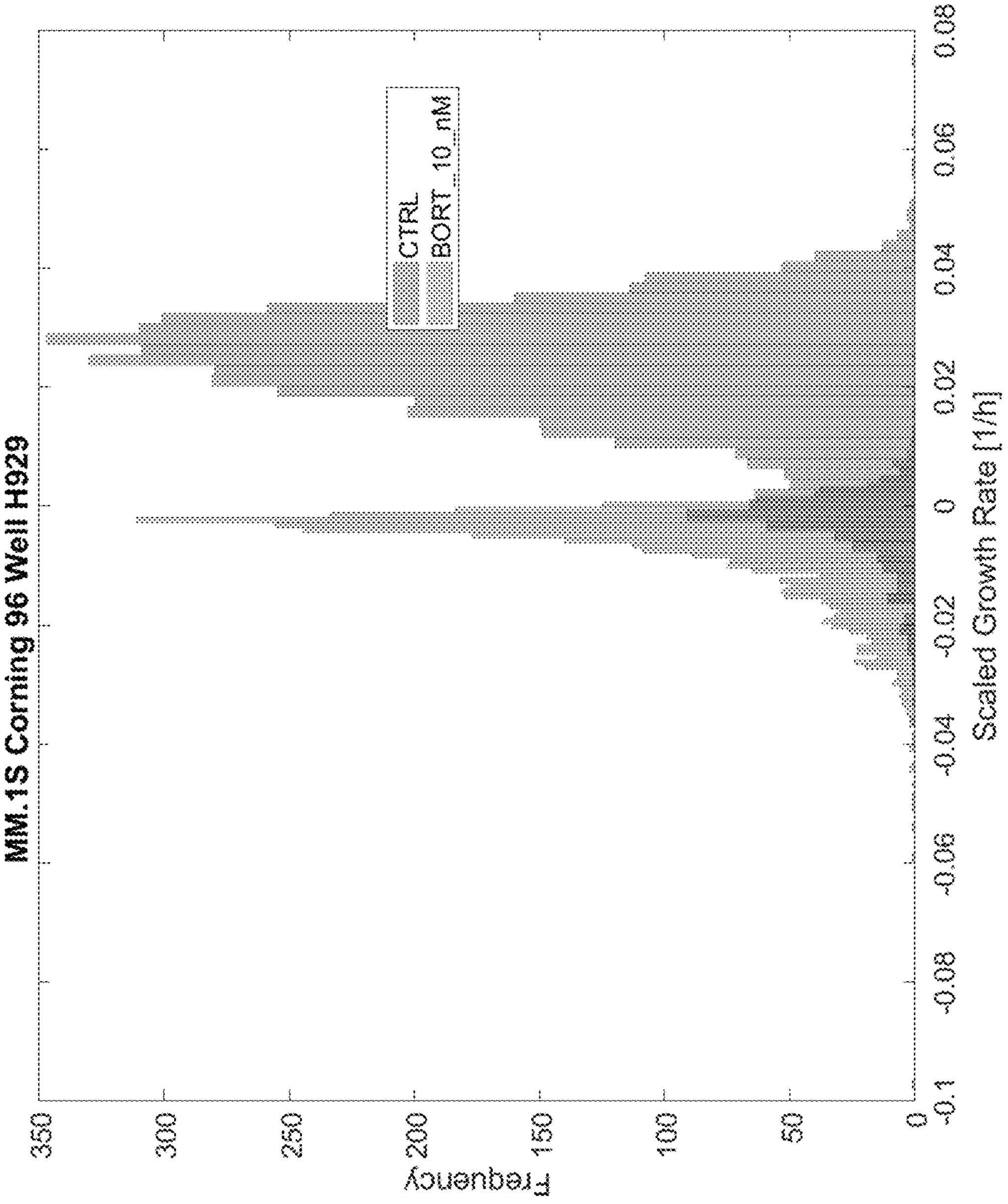
Figure 21F:
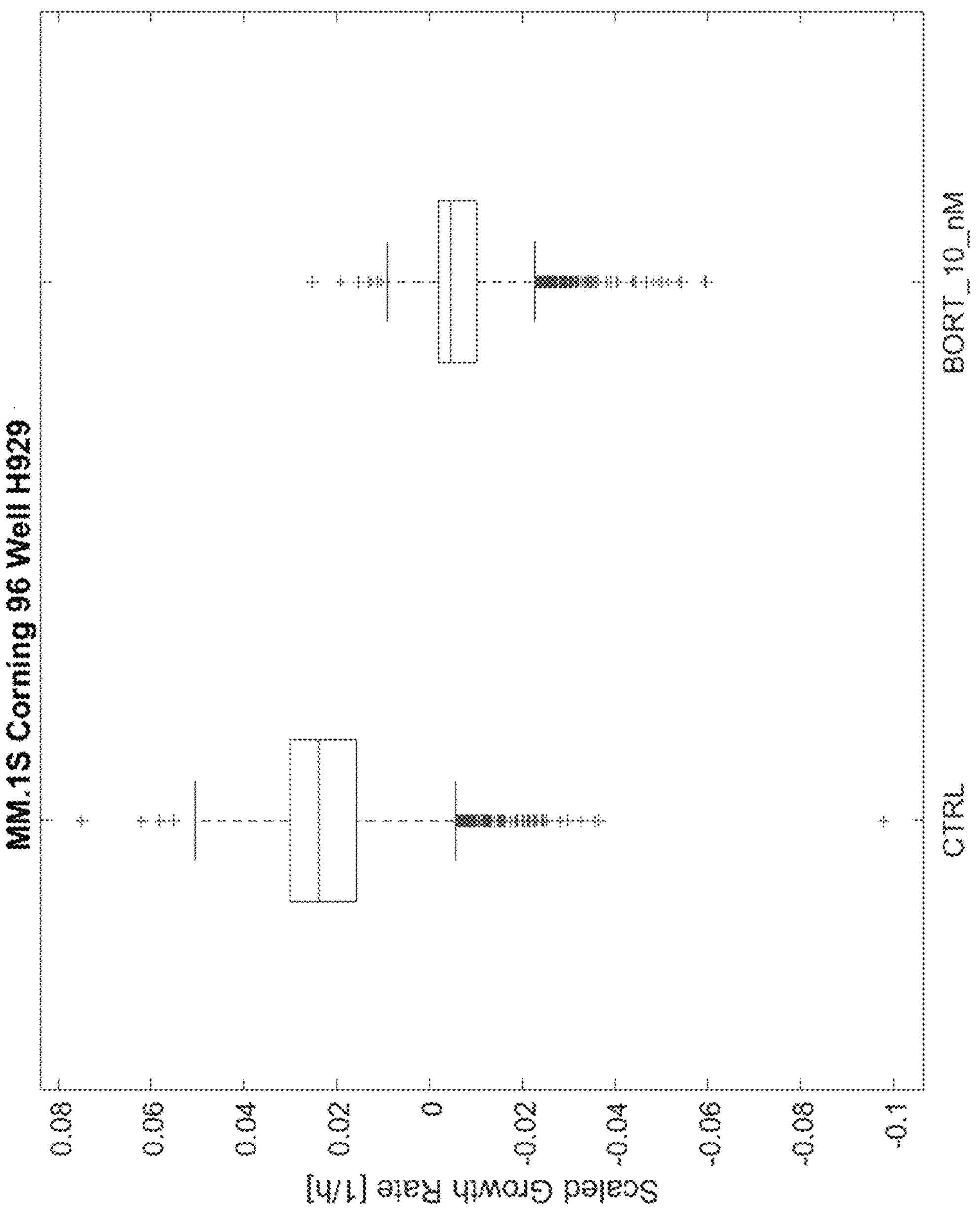

FIGS. 21E and 21F show growth rate distributions of individual cells, shown as a histogram in FIG. 21E and as a box plot in FIG. 21F. In both graphs, the treated population with bortezomib has a lower growth rate.

Figure 22B:
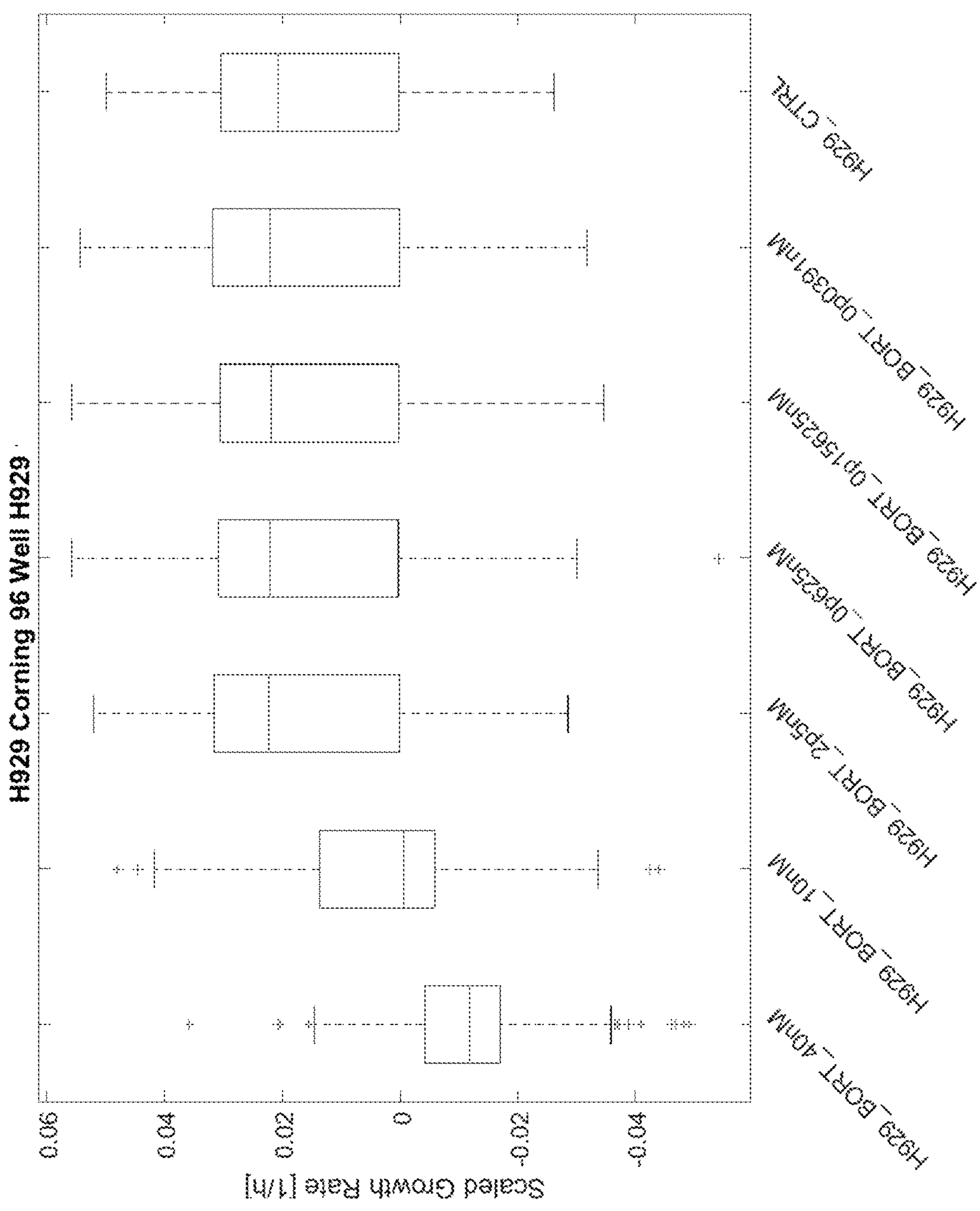
Figure 22C:
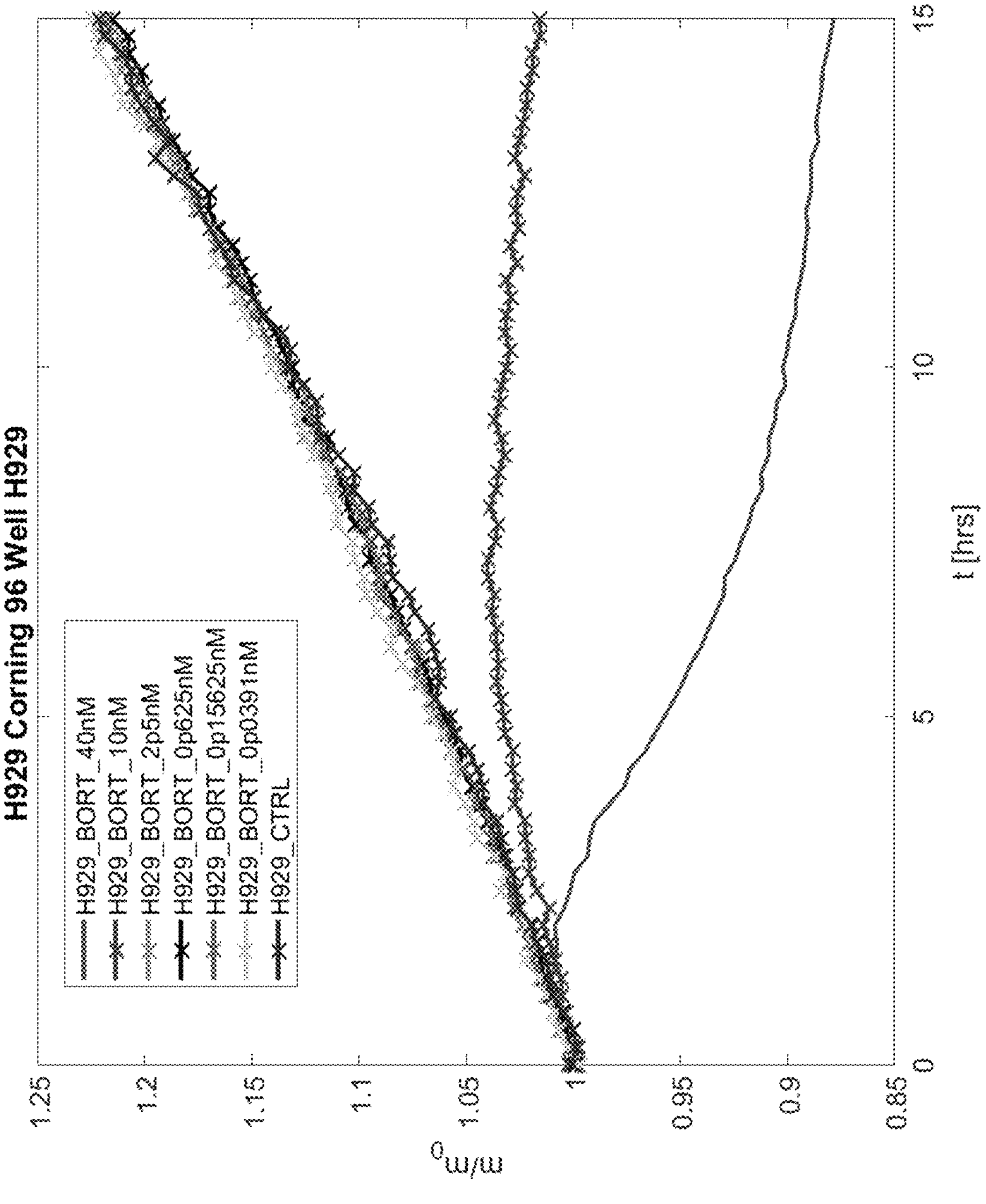
Figure 22D:
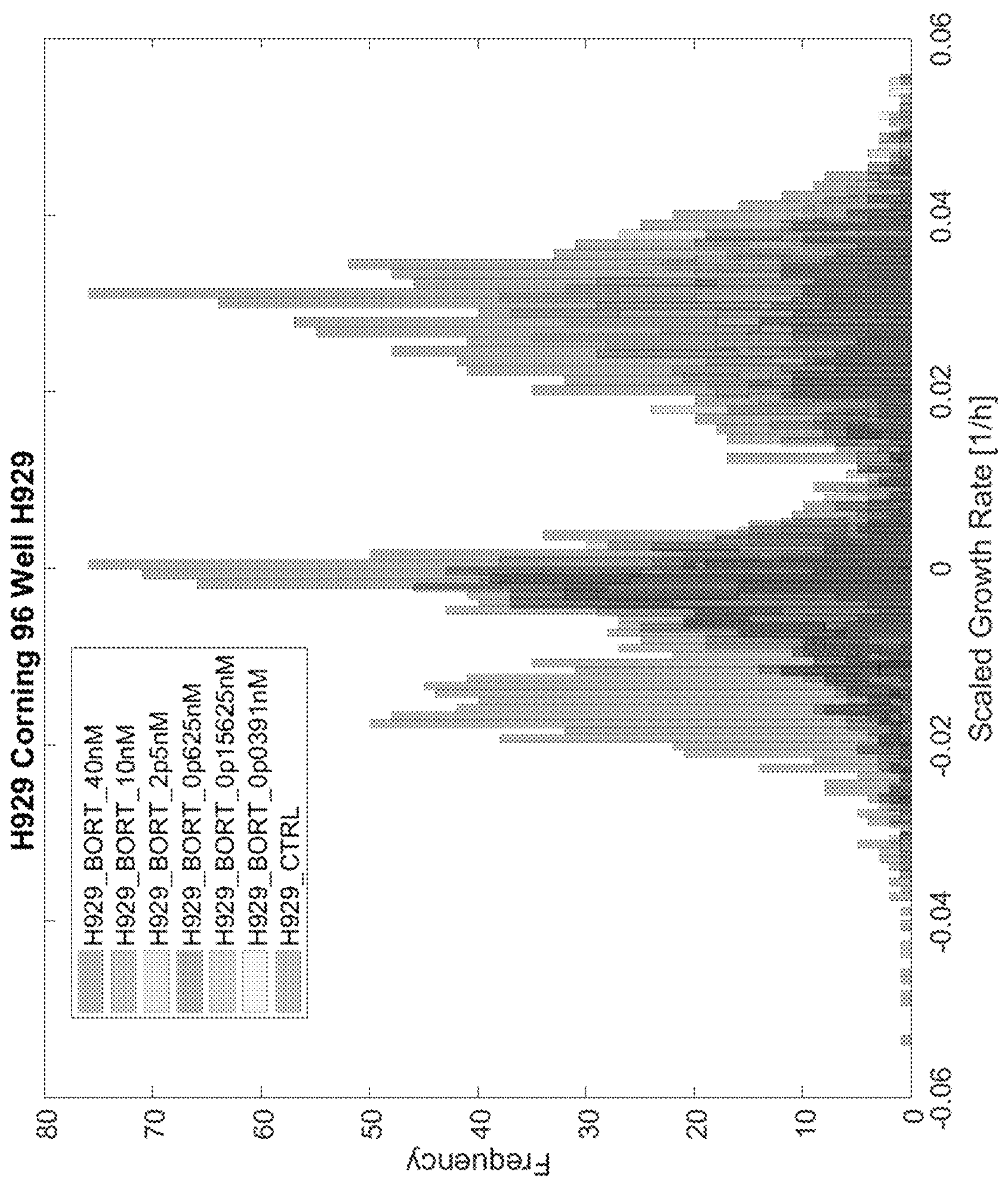

FIGS. 22A-22D show another study using bortezomib. FIG. 22A shows results of bortezomib treated H929 cells at various concentrations (e.g., 0, 0.039, 0.156, 0.625, 2.5, 10 and 40 nM). A clear response to the therapeutic was observed, with the drug $EC_{50}$ expected to be between 2.5-10 nM. A corresponding box chart is provided in FIG. 22B. FIG. 22C shows a growth curve of various groups of wells (e.g., each group of wells corresponding to a different concentration of bortezomib), with a corresponding histogram shown in FIG. 22D. As shown by these data, a concentration of 2.5 nM did not show a difference in growth trajectory as compared to the control, while a concentration of 10 nM showed a significant decline in growth.

Example 3. Screening of Mm1.S Cells

Figure 23B:
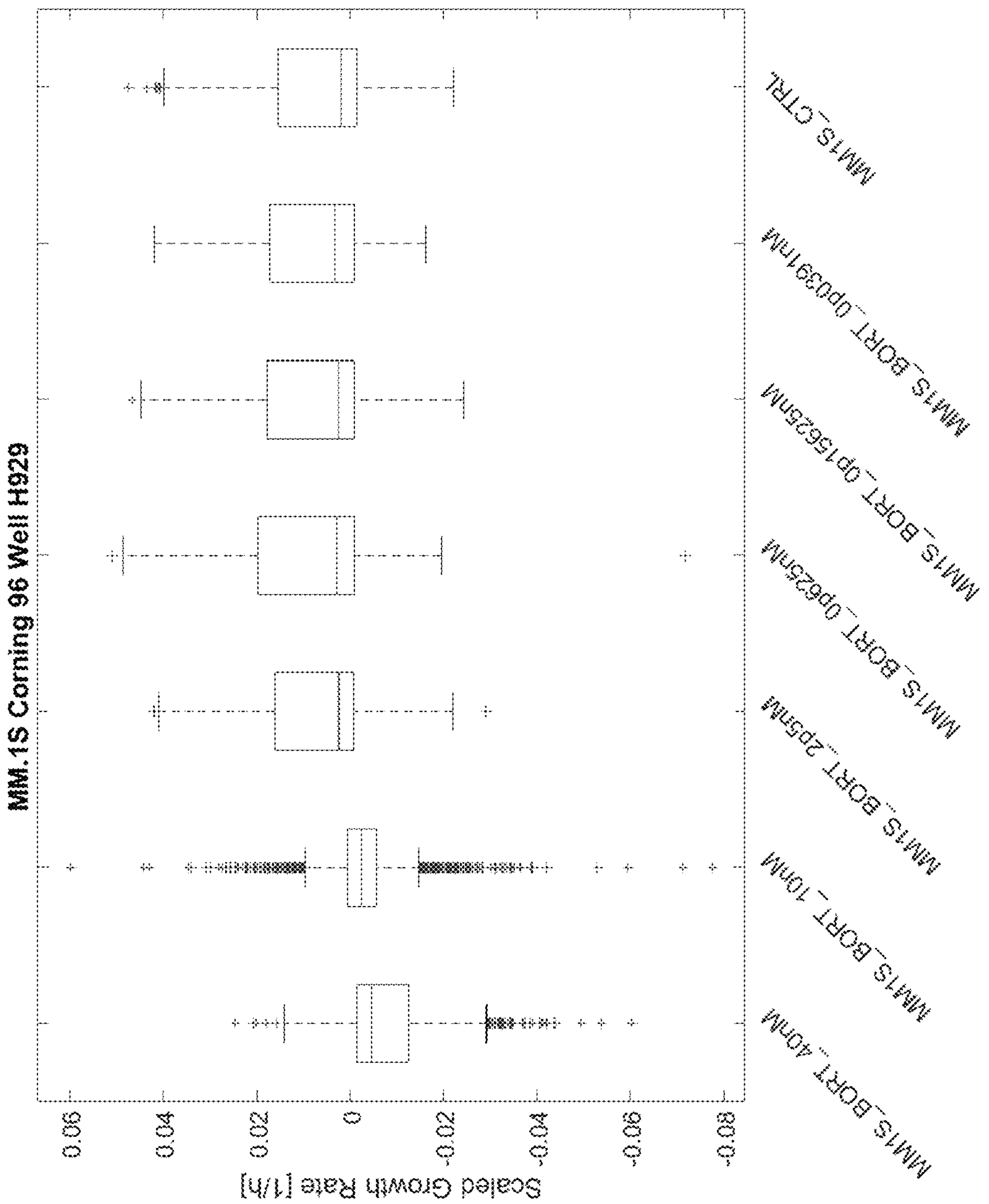
Figure 23C:
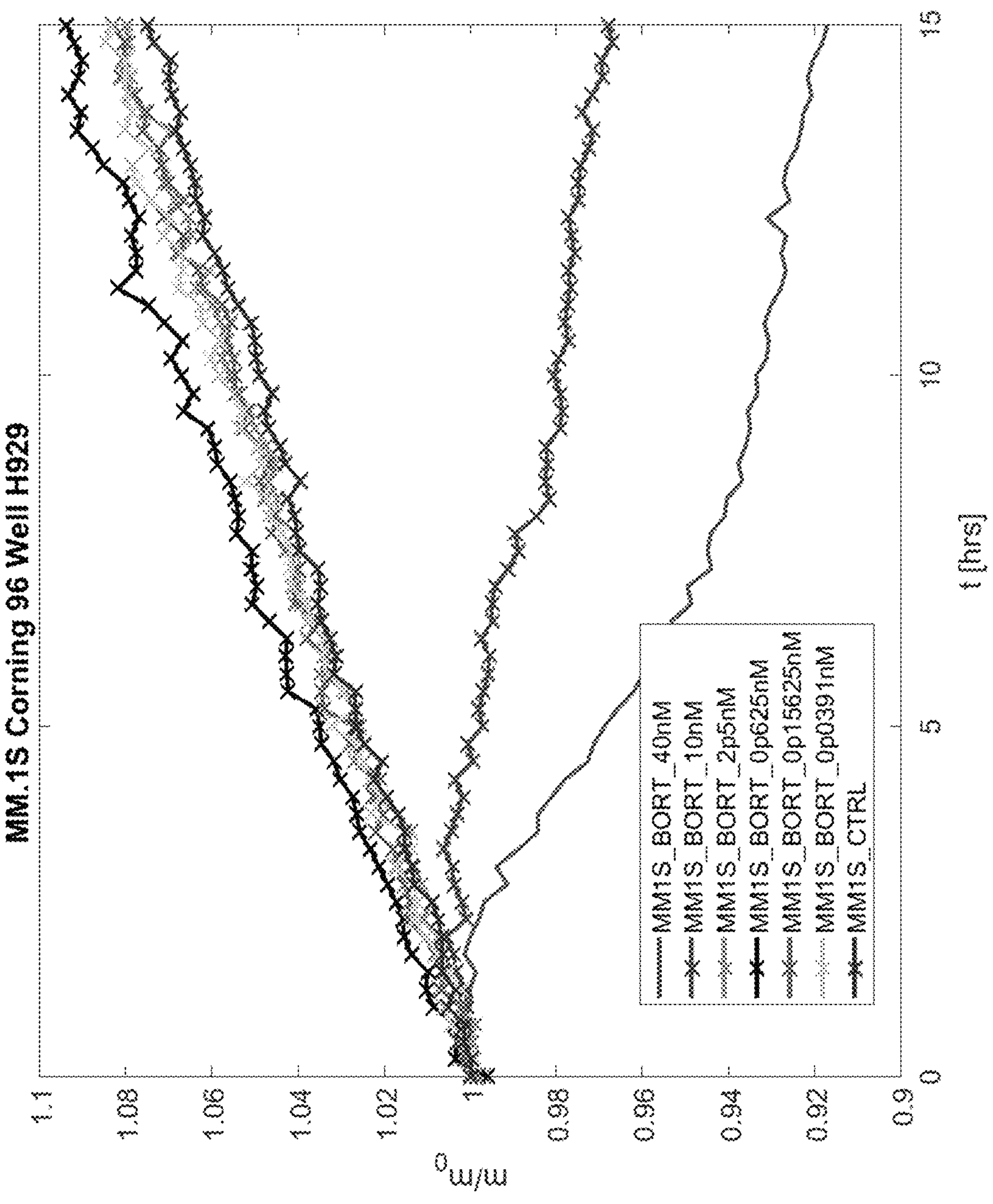
Figure 23D:
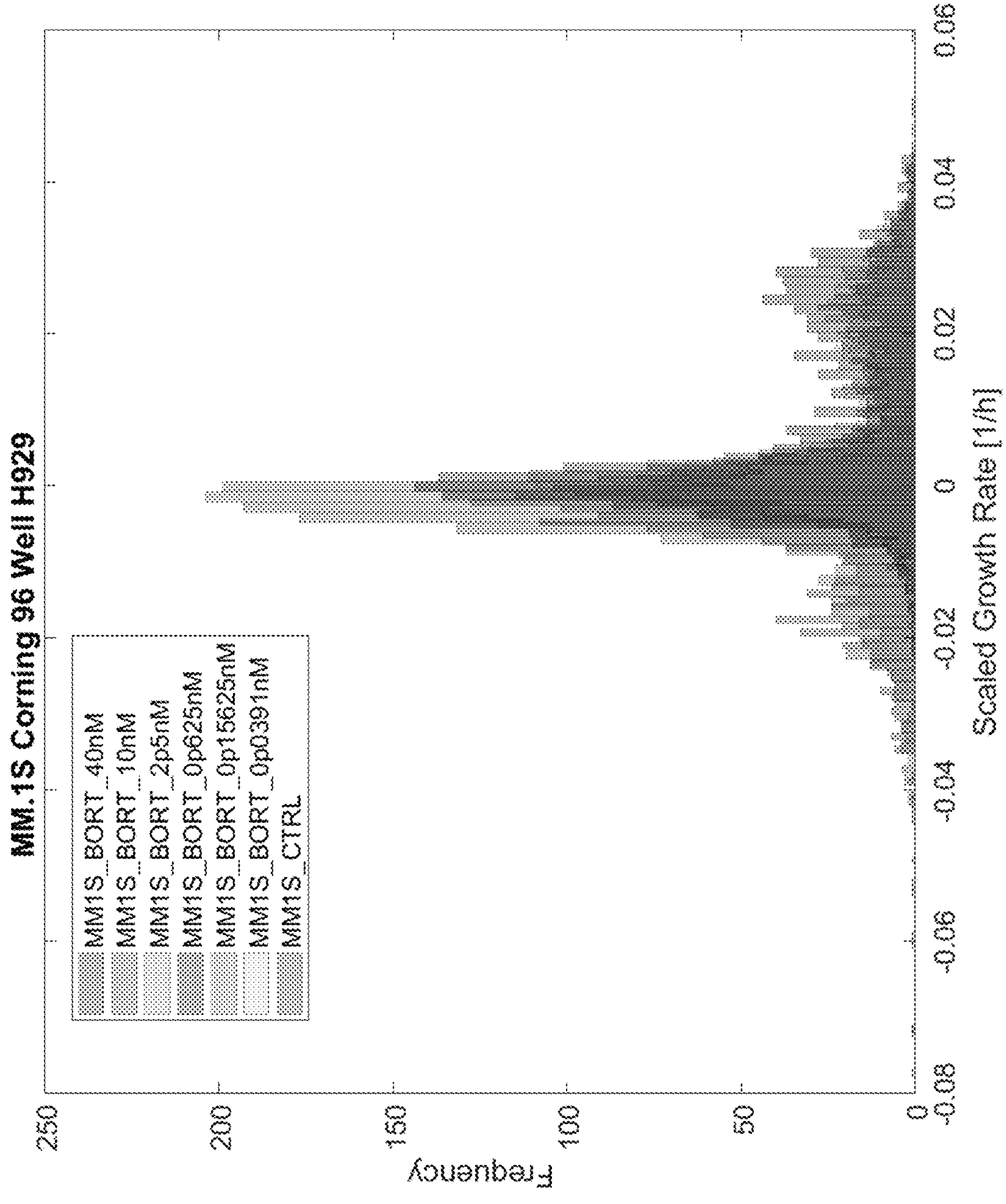

FIG. 23A shows results of treating MM1.S cells with bortezomib. In general, MM1.S cells are smaller than H929, and a higher number of cells can be tracked on a plate. The response was similar to H929 cells, with an $EC_{50}$ between 10 and 2.5 nM. Differences at low concentrations were determined not to be statistically significant. FIG. 23B shows a box plot of varying concentrations of bortezomib. FIG. 23C shows a growth curve of various groups of wells (e.g., each group of wells corresponding to a different concentration of bortezomib), and a corresponding histogram is shown in FIG. 23D.

Example 4. Screening of Sensitive and Resistant MM.1 Cells

In this example, MM.1S (sensitive) and MM.1R (resistant) cells were treated with dexamethasone. MM.1S cells and MM.1R cells were isolated from patients. The $IC_{50}$ of dexamethasone in MM.1S was reported to be 200 nM. Accordingly, this concentration of dexamethasone was selected for the following study.

About $2.5 \times 10^5$ cells per well were placed on a poly-D-lysine 12 well plate, and incubated for one hour. About 200 nM dexamethasone, 10 nM bortezomib, or DMSO (in duplicate wells) were added to each well, and images were collected every 15 mins for up to 15 hours. The results confirmed that the MM.1S DMSO control, MM.1R, and MM.1R with dexamethasone all had similar growth rates, and thus, MM.1R was confirmed to be resistant to bortezomib. In contrast, dexamethasone was shown to reduce MM.1S growth by 80.5%, with significant differences observed after 2-3 hours.

Figure 24A:
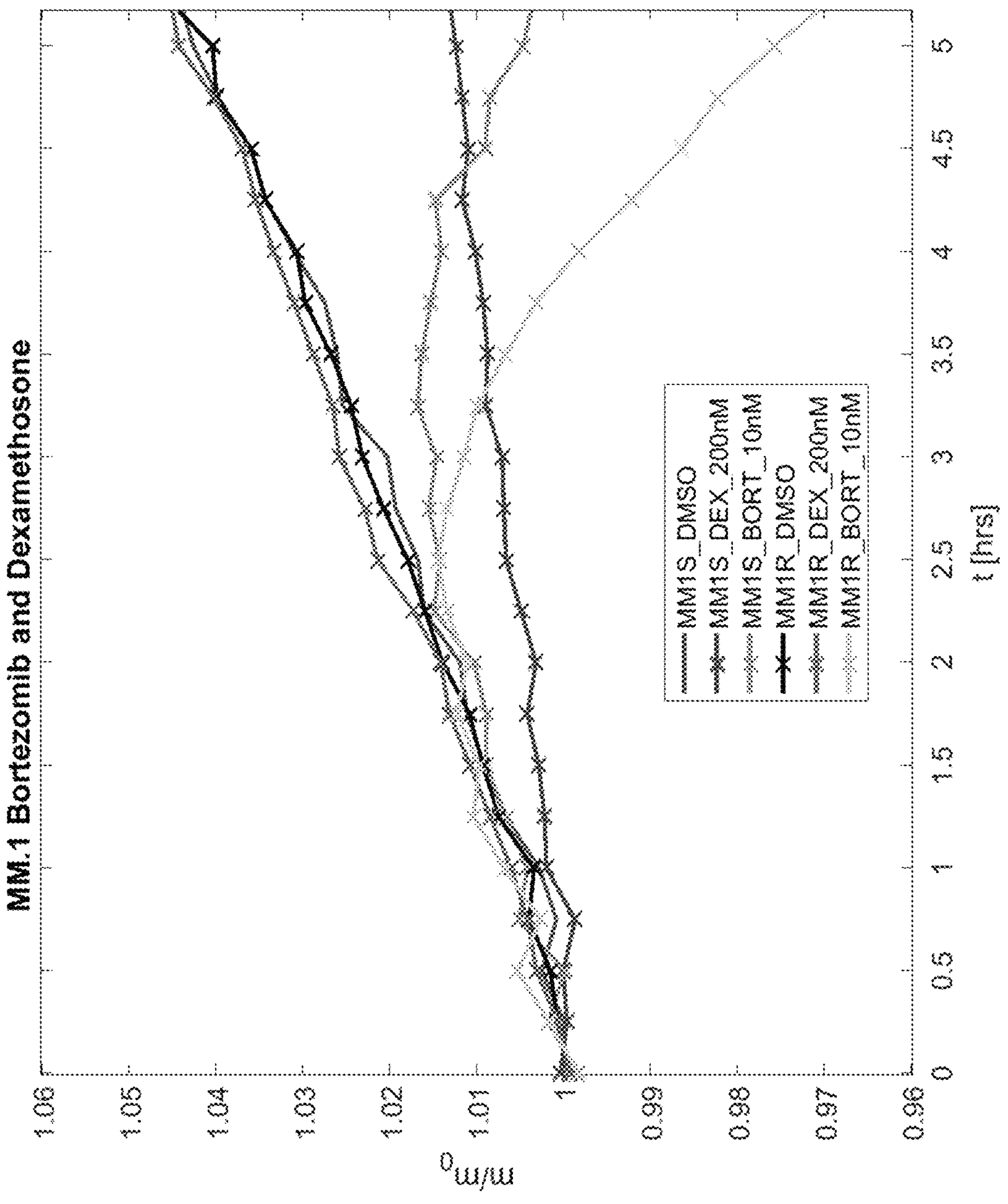
Figure 24B:
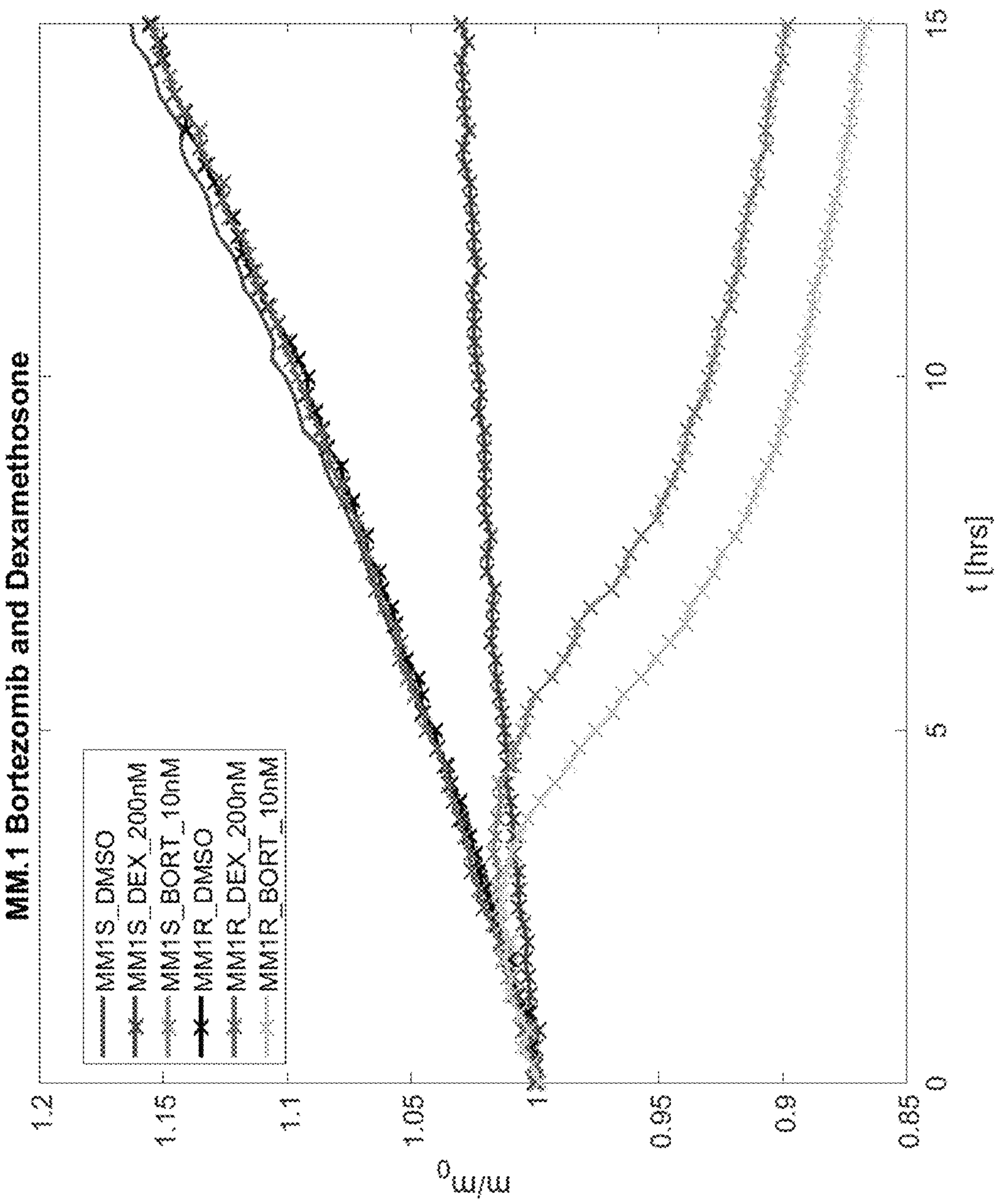
Figure 24D:
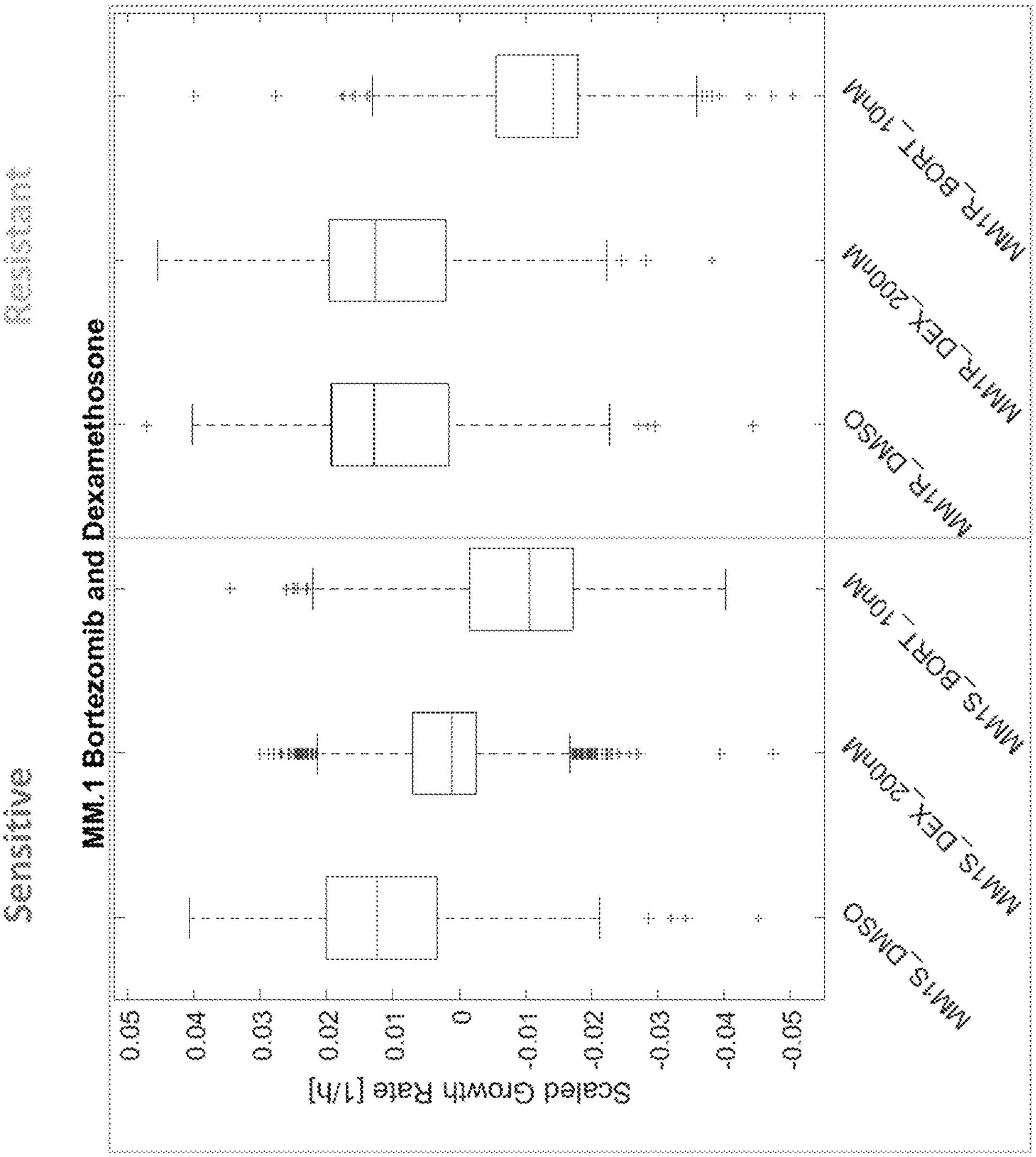

FIGS. 24A and 24B also show that MM.1R and MM.1S cells were both sensitive to bortezomib, with significant differences observed after 5 hours. These results are also shown in table format (FIG. 24C) and box plot format (FIG. 24D). A large number of cells were screened in each group (greater than 1000 cells), and differences were statistically significant ($p<0.00001$).

Example 5. Multiple Myeloma Combinatorial Screening of Therapeutics

FIG. 25A shows an example well configuration for a screening assay for measuring the effects of various therapeutics on a cell line. In this example, 6 therapeutics at 3 different concentrations, were added in quadruplicate to a 96 well plate. Thus, there were 19 different conditions: bortezomib (20, 5, 1.25 nM); carlifomib (50, 10, 2 nM); dexamethasone (300, 100, 33.3 nM); lenalidomide (50, 10, 2 nM); panobinostat (50, 10, 2 nM); pomalidomide (50, 10, 2 nM); and DMSO (300 nM) as a negative control. In clinical practice, the actual drugs/combinations may be provided by the clinician.

In this study, a large number of cells (~12,000 total cells) were screened to identify optimal drugs and concentrations. This assay, while performed on MM.1R and MM.1S cells may be performed on any suitable cell type (e.g., patient derived cancer cells from multiple myeloma, breast cancer, lung cancer, etc.). For multiple myeloma cells, a protocol for CD138+ cell enrichment from patient bone marrow is provided in the art.

In some aspects, drugs, doses, and drug combinations may be specified by a clinician. In other aspects, assays may be modified to mimic bolus drug administration, e.g., adding a drug, incubating for 1 hour, washing and re-suspending in media, followed by imaging. Many different variations are possible, and all such are within the scope of the present techniques.

Other groups have used mass accumulation rates measured with different mass measurement tools (e.g., microfluidics devices) to predict clinical outcome (see, e.g., Cetin et al., *Nature Communications* (2017) 8:1613).

The present system offers several advantages over other systems including improved throughput (e.g., high throughput, testing for >2000 cells; higher number of cell tracks, etc.). The present system, which may utilize wells (e.g., cells that may adhere to a surface), also offers greater flexibility, testing for up to 28 different conditions in triplicate, without relying on complicated microfluidics. Additionally, in the present system, well positions of different drugs/concentrations may be spatially randomized, as shown in FIG. 25A, to account for temperature gradients, which may intrinsically affect growth rates. Furthermore, the present system allows for testing of suspension as well as adherent cells, and it also allows for cells to be tested at physiological environmental conditions (which may for example be 37° C. and 5% $CO_2$).

Figure 25B:
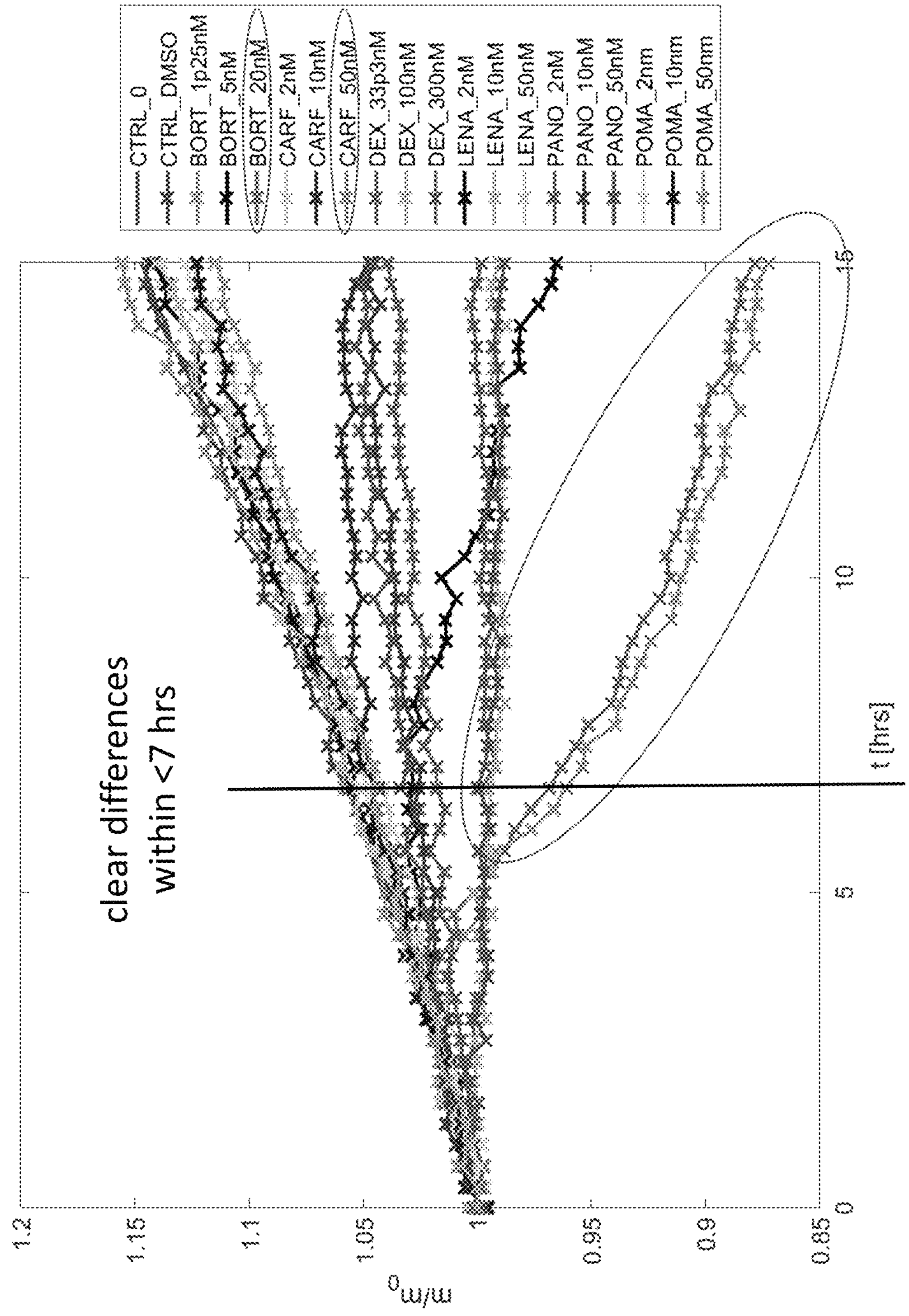
Figure 25C:
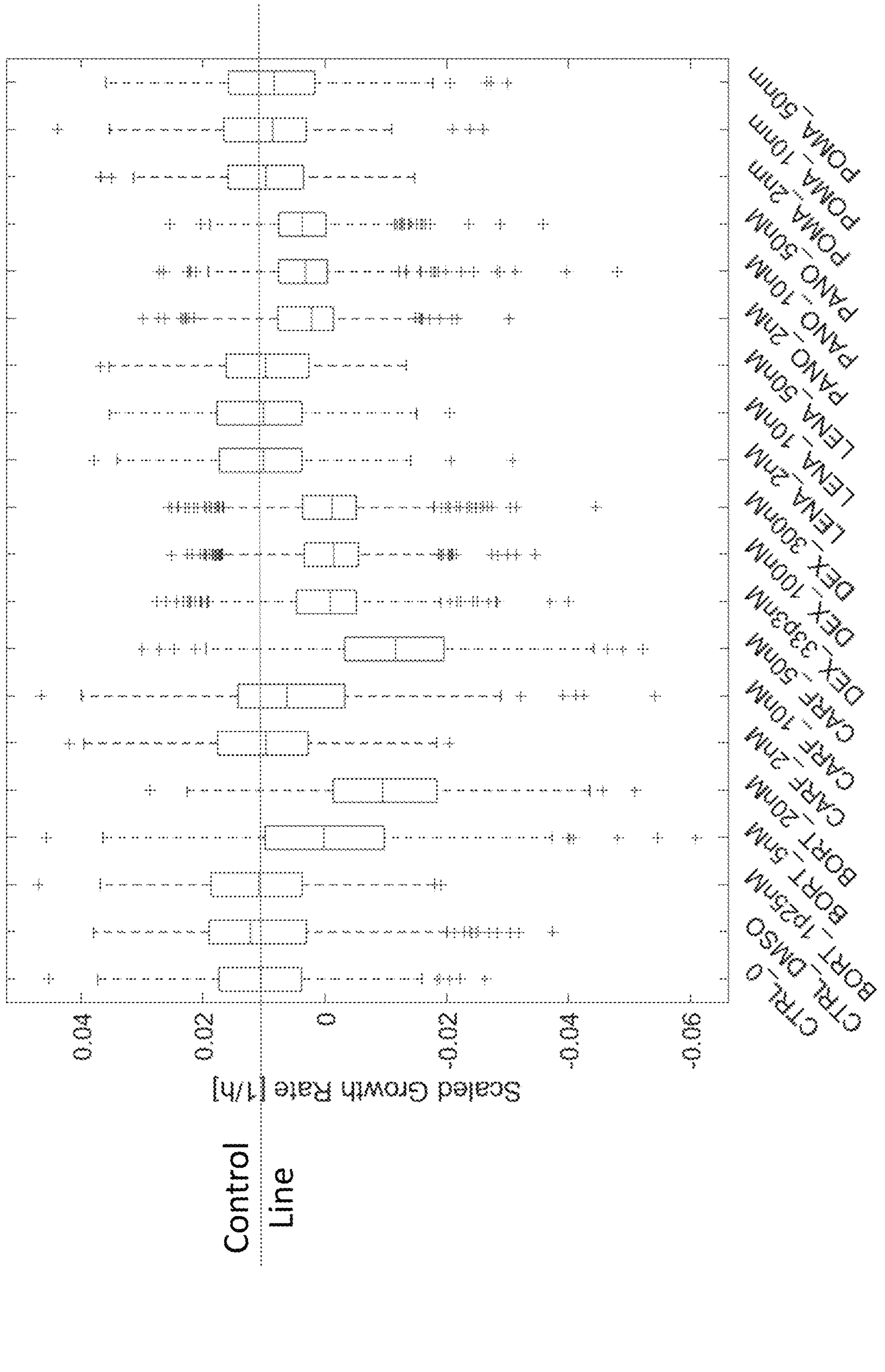

FIGS. 25B, 25C, and 25D show the results of this assay, in graphical, dot box, and table format respectively, in which multiple "best treatments" were identified using this system. The overall results were: (1) bortezomib: good/great response, good titration effect; (2) carfilzomib: good/great response, good titration effect; (3) dexamethasone: good response, no titration effect (could lower concentration); (4) lenalidomide: no response, no titration effect (need higher concentration); (5) panobinostat: good response, no titration effect (could lower concentration); and (6) pomalidomide: some response, good titration effect. As shown by the data, bortezomib 20 nM and carfilzomib at 50 nM were determined to be the most effective drugs. Statistically significant differences were observed in about seven hours.

Example 6. Screening of MM.1S and MM.1R

Figure 26A:
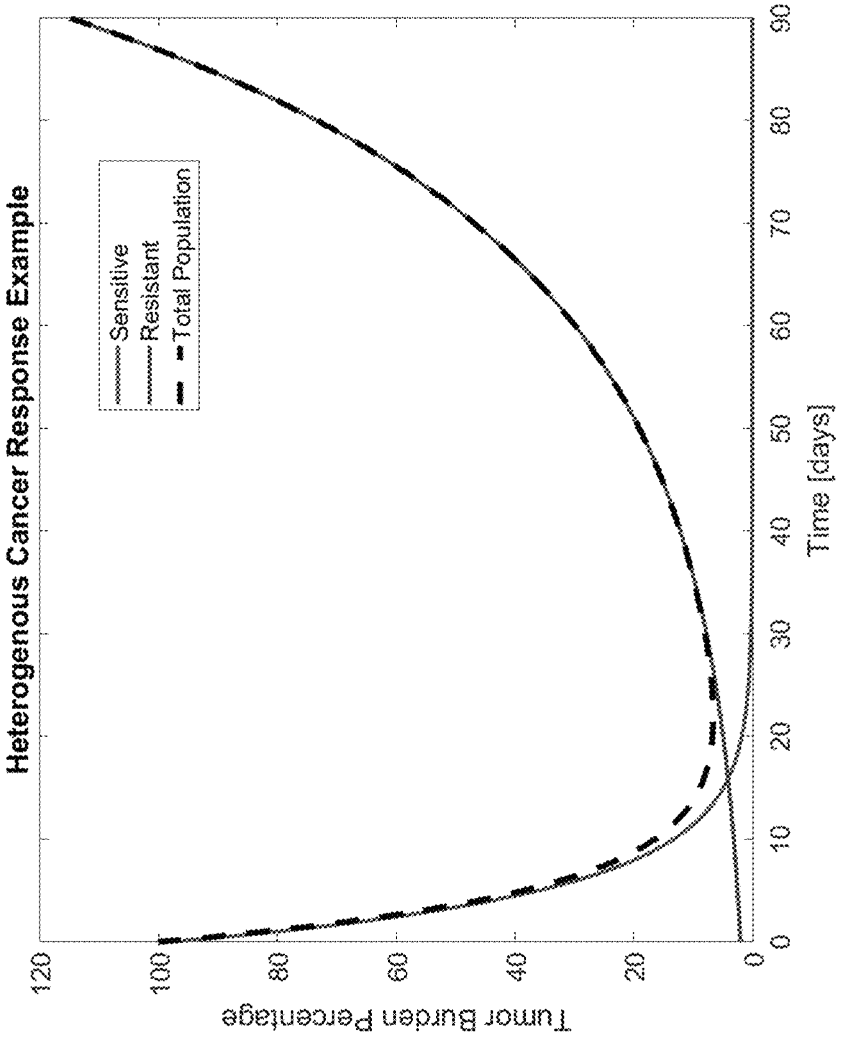
FIGS. 26A, 26B, 26C and 26D show growth of MM.1 cells with and without dexamethasone, according to aspects of the present disclosure.

In a previous example, both sensitive (MM.1S) and resistant (MM.1R) cells were treated with various therapeutics separately. However, in some types of cancer, the cancer may be heterologous, with different sub-populations having different mutations and different sensitivities. Thus, a particular type of cancer in an individual may comprise populations of cells that are sensitive and resistant to a particular drug. In such cases, it is desirable to identify a drug that will treat all of the cancer cells to prevent or reduce recurrence or resistance of the cancer. If the administered drug primarily affects the sensitive cells, but not the resistant cells, then treatment can ultimately fail and the resistant form of the cancer may continue to grow and spread. In cases in which the sensitive cells significantly outnumber the resistant cells, it may appear that the administered therapy is working, as a reduction in tumor mass may be observed due to elimination of the sensitive cells. However, long term, the resistant cells will grow and repopulate, causing to patient to undergo subsequent rounds of treatment. FIG. 26A shows the cancer mass being initially depleted, but the resistant cells were able to repopulate over time and dominate. Thus, it is desirable to identify the correct drug or combination of drugs to effectively treat the cancer in its entirety.

For this example, resistant and sensitive cells (e.g., cells susceptible to drugs) are mixed together in order to represent a heterogeneous patient sample. Thus, some cells of the mixed population may respond to therapy, while other cells may not respond. In various implementations, the different cell types may be different cell lines. Some example techniques described herein are directed towards distinguishing between heterogeneous populations of cells, in order to identify the optimal drug for the heterogeneous population.

An example protocol may include plating about $2.5\times10^5$ cells in each plate of a twelve well plate. Ideally, each well will have the same or about the same total number of cells. The population of cells may be a mixed combination of resistant and sensitive cells, of varying percentages. Once plated, the therapeutic(s) may be added, and the cells may be imaged every 15 minutes for 8-24 hours. In various implementations, cell lines may be mixed in known ratios, to measure drug response on mixed populations. For example, a sample may be created that includes 50% of cells from cell line A and 50% of cells from cell line B, to measure drug response on a 50/50 population. Another sample may be created that includes 75% of cells from cell line A, and 25% of cells from cell line B, to measure drug response on a 75/25 population.

Figure 26B:
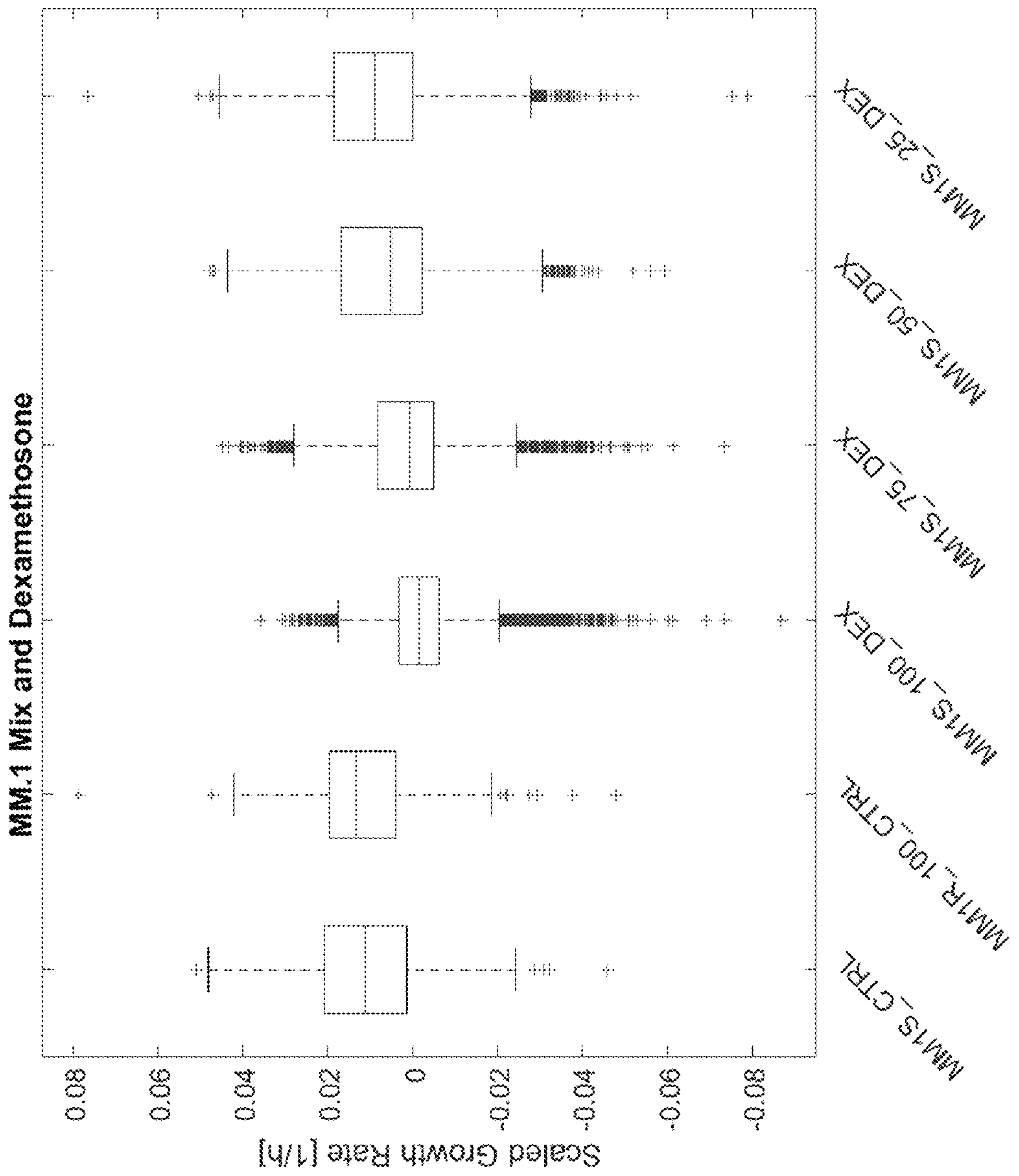
Figure 26C:
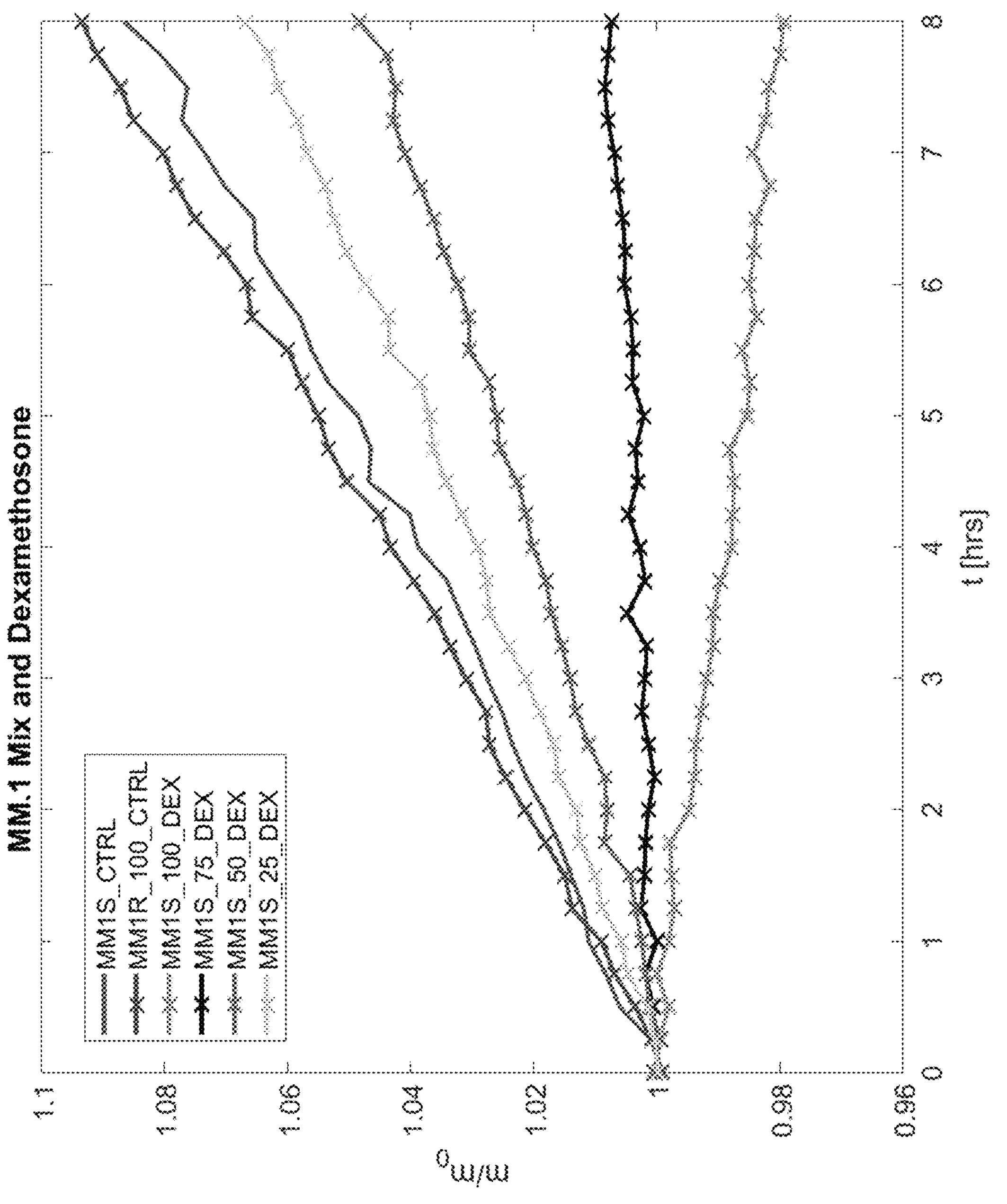

In FIGS. 26B and 26C, experimental results are shown of mixed amounts of resistant and sensitive cells. In these examples, 200 nM dexamethasone is applied to cells, some of which are mixed populations: (1) 0% sensitive cells, 100% resistant cells; (2) 25% sensitive cells, 75% resistant cells; (3) 50% sensitive cells, 50% resistant cells; (4) 75% sensitive cells, 25% resistant cells; and (5) 0% sensitive cells, 100% resistant cells. In addition, two unmixed control wells with no drug were used as controls.

As shown by the results, in a population of mixed MM.1S and MM.1R cells, the growth rate was titratable. After 8 hours, clear differences in growth rates were determined for each mixed population. The percentage of sensitive cells was directly correlated with average growth inhibition, such that as the percentage of sensitive cells increased, the average growth rate decreased. A statistically significant difference from control cells was observed even when only 25% of cells were sensitive.

Figure 26D:
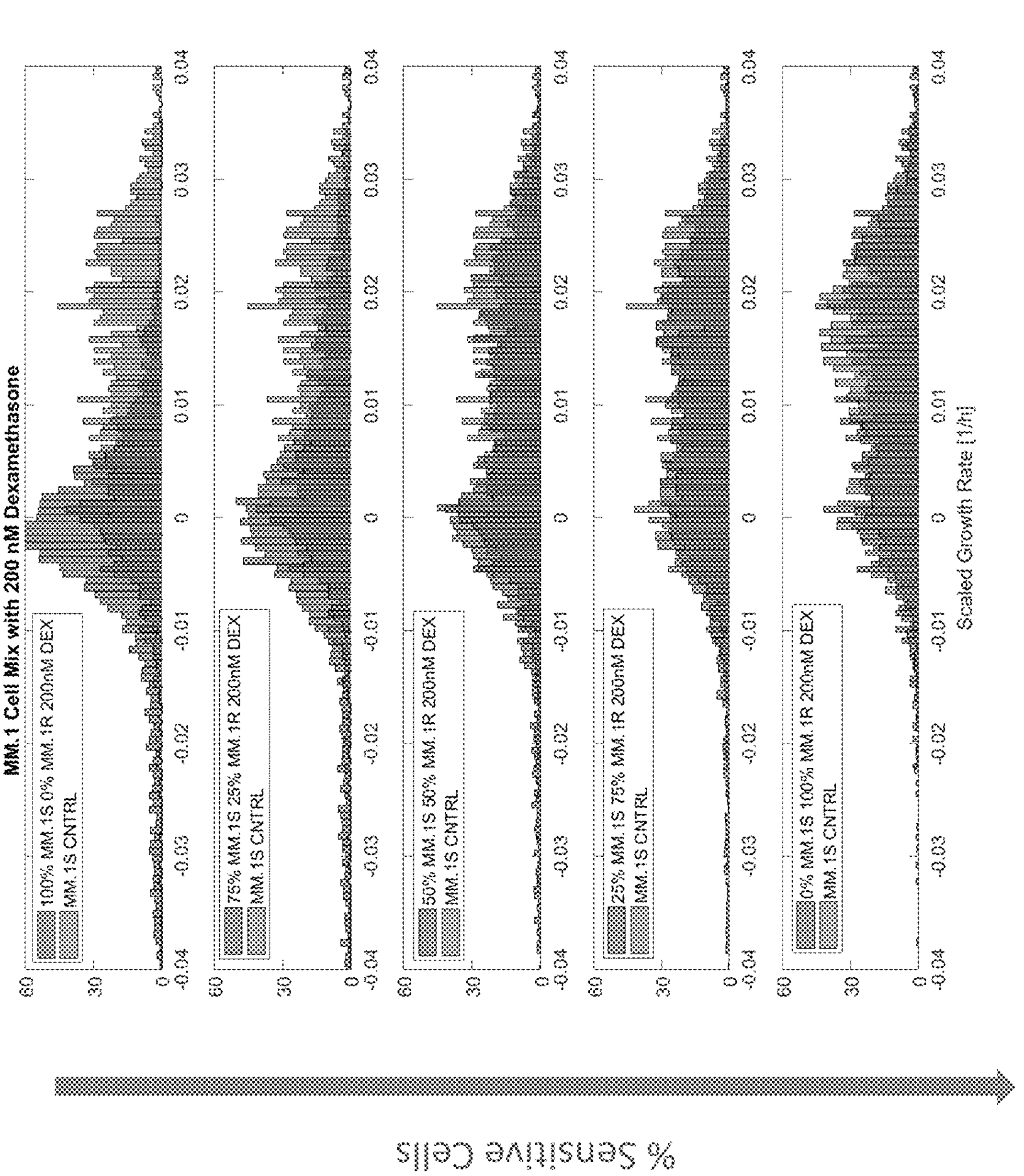

FIG. 26D shows the results in histogram format. As LCI is a single cell screening technique, heterogeneity in the population may be determined by looking at distribution of growth rates. As the percentage of sensitive cells decreases, and thus, resistant cells increase, the population resembles a population with no drug. Once identified, each population may be evaluated (e.g., by comparing to other population(s)), to determine whether heterogeneity of a cell population is present in response to a treatment with a chemotherapeutic.

In various implementations, a system may run population dynamics on cell samples to identify possible cells that may have resistance to a drug, which could create problems in the future. For example, FIG. 26A illustrates that while a drug may have a promising effect at reducing certain cells initially, other cells that are resistant to the drug may start growing over time. Comparing curves of population dynamics for multiple populations (such as in the example of FIG. 26D), may allow for analysis to see which drugs work best on a cell population. For example, a drug that inhibits growth of all cell types of a sample population may compare favorably to a drug that shows a stronger initial cell decline in the overall sample population but then allows a resistant cell type to grow over time.

Figure 27A:
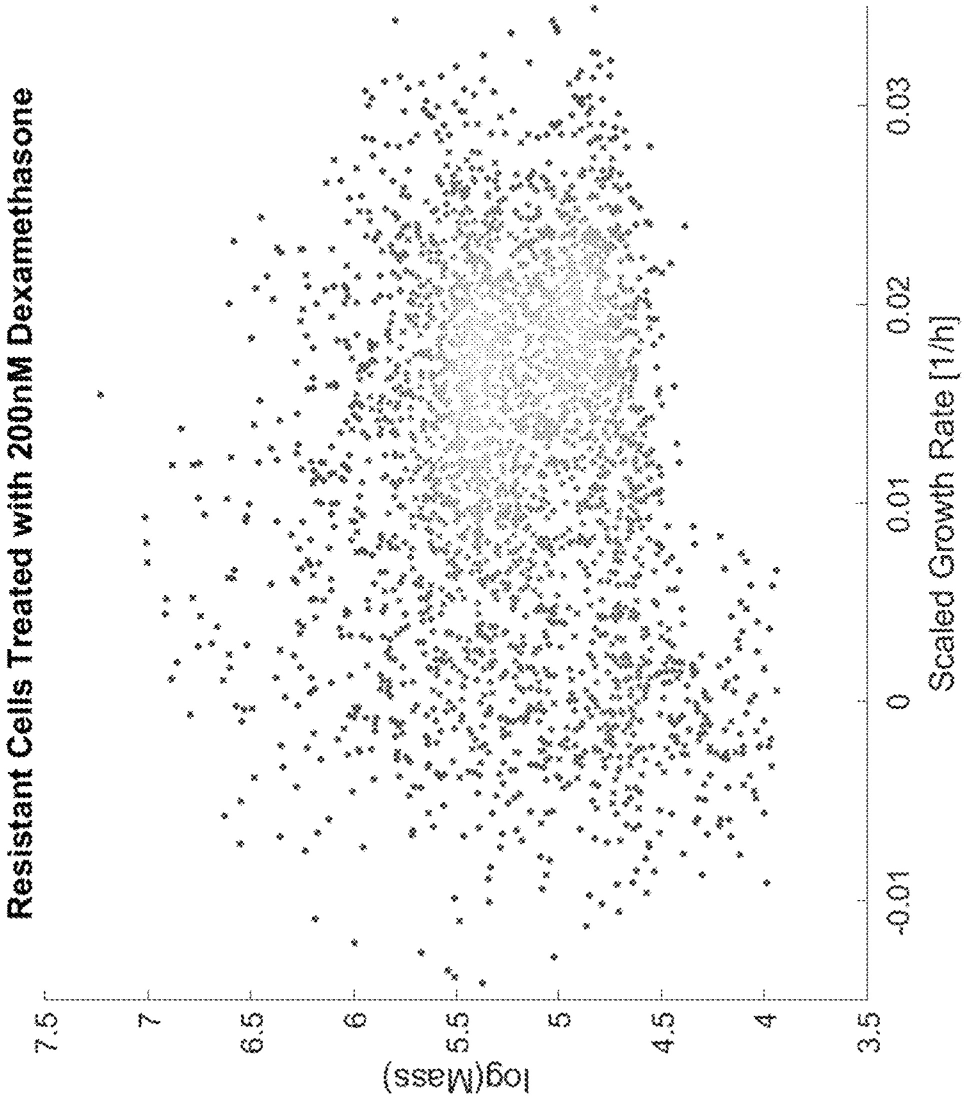
FIGS. 27A, 27B, 27C, 27D and 27E show growth for sensitive and resistant cells in a mixed population, with and without dexamethasone, according to aspects of the present disclosure.
Figure 27B:
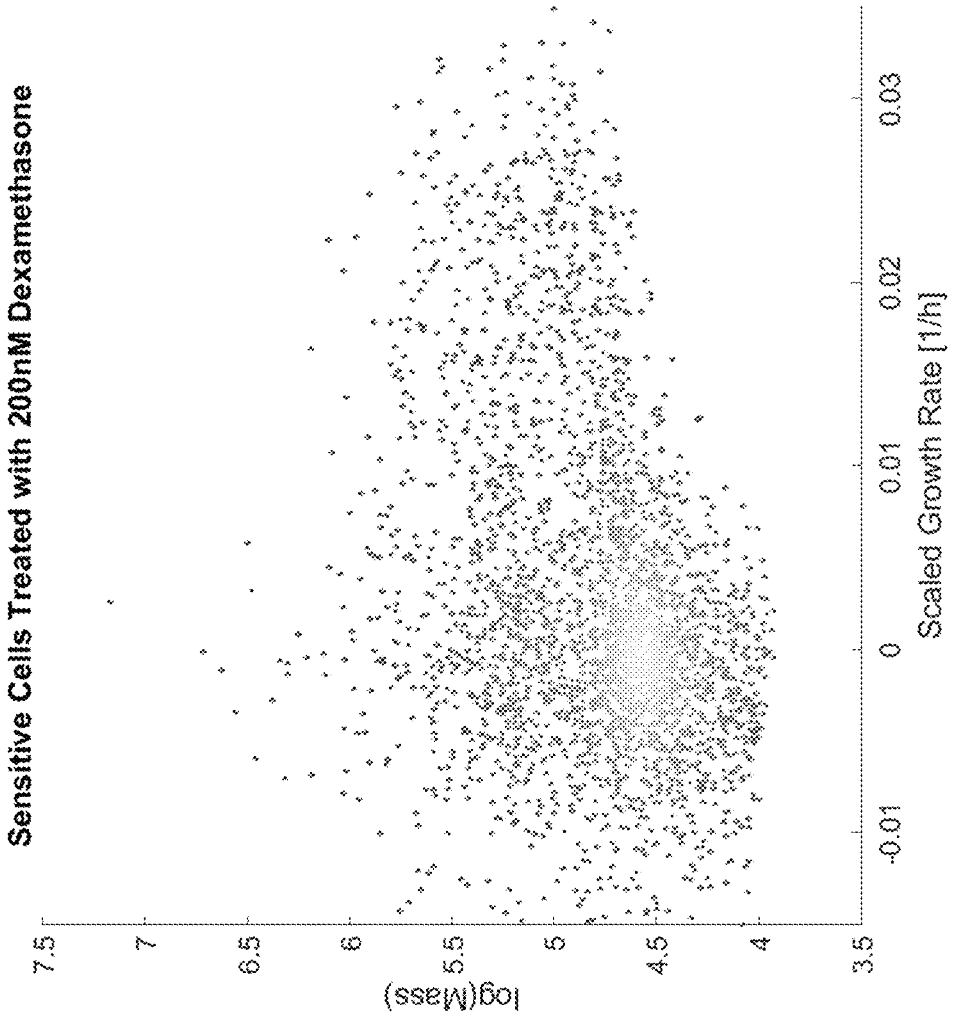

FIGS. 27A and 27B show log(mass) and growth rate distributions of a population of resistant cells (FIG. 27A) and a population of sensitive cells (FIG. 27B.) Both populations were treated with the same concentration of therapeutic, in this case, 200 nM dexamethasone.

Figure 27C:
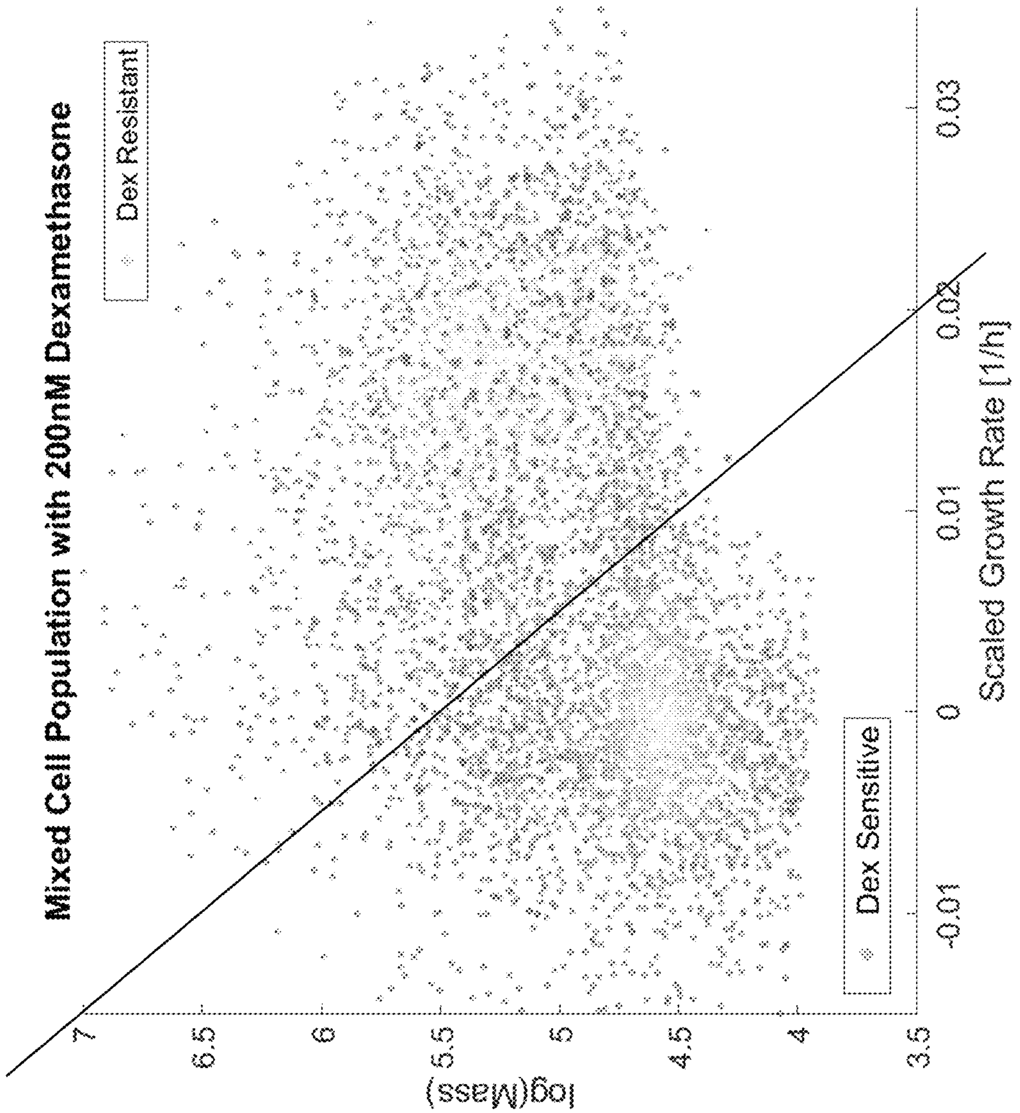

FIG. 27C, a superposition of FIGS. 27A and 27B, shows a combination of both sensitive and resistant cells with significant overlap. Factors that may affect overlap include, but are limited to: similarity between cell lines, cells that were isolated from same patient, an increasing number of features to track, and/or cell line contamination. FIG. 27C shows the combined cell populations of resistant and sensitive cells. These sensitive and resistant cells have different growth distributions, with the sensitive cells being concentrated in the lower left quadrant corresponding to a reduced growth rate, and the resistant cells being concentrated in the upper quadrant corresponding to an increased growth rate.

This figure also shows an example of generating a simple model with which to analyze mixed populations of sensitive and resistant cells. In this example, a line is used to separate the two populations of cells. Cells below the line are considered to be sensitive, while cells above the line are considered to be resistant. Any suitable manner of partitioning the data, including the use of more complex models with non-linear functions is contemplated herein.

Due to the distribution and variability within a population of cells, some of the resistant cells may be present in the lower quadrant, and some of the sensitive cells may be present within the upper quadrant. Therefore, this model may be refined by assuming overlap between the sensitive and resistant cell populations. For instance, the MM.1S population below the user defined line may be assumed to have a sensitive cell percentage of $S_s$=69.25% and a resistant cell percentage of $R_s$=30.75%. Similarly, the MM.1R population above the user defined line may be assumed to have a sensitive cell percentage of $S_r$=20.04% and a resistant cell percentage of $R_r$=79.96%, in order to estimate overlapping populations of sensitive and resistant cells.

Using this overlap assumption and the following formula, the mixing percentages of the cells may be calculated using the following equations:

$$\%\ s_{mix} = mixRatio_s S_s + mixRatio_r S_r$$

$$\%\ r_{mix} = mixRatio_r S_s + mixRatio_r S_r$$

For example, using the overlap assumption and presuming different mixing ratios of sensitive and resistant cells, e.g., a 25% sensitive/75% resistant mix of cells, a 50% sensitive/50% resistant mix of cells and a 75% sensitive/25% resistant mix of cells, the mixing ratios may be calculated as:

$$\% \ s_{mix} = 0.25 \times 0.6925 + 0.75 \times 0.2004 = 0.173 + .150 = .323$$

$$\% \ s_{mix} = 0.50 \times 0.6925 + 0.50 \times 0.2004 = 0.346 + .100 = .447$$

$$\% \ s_{mix} = 0.75 \times 0.6925 + 0.25 \times 0.2004 = 0.519 + .050 = .570$$

Figures 27D, 27E:
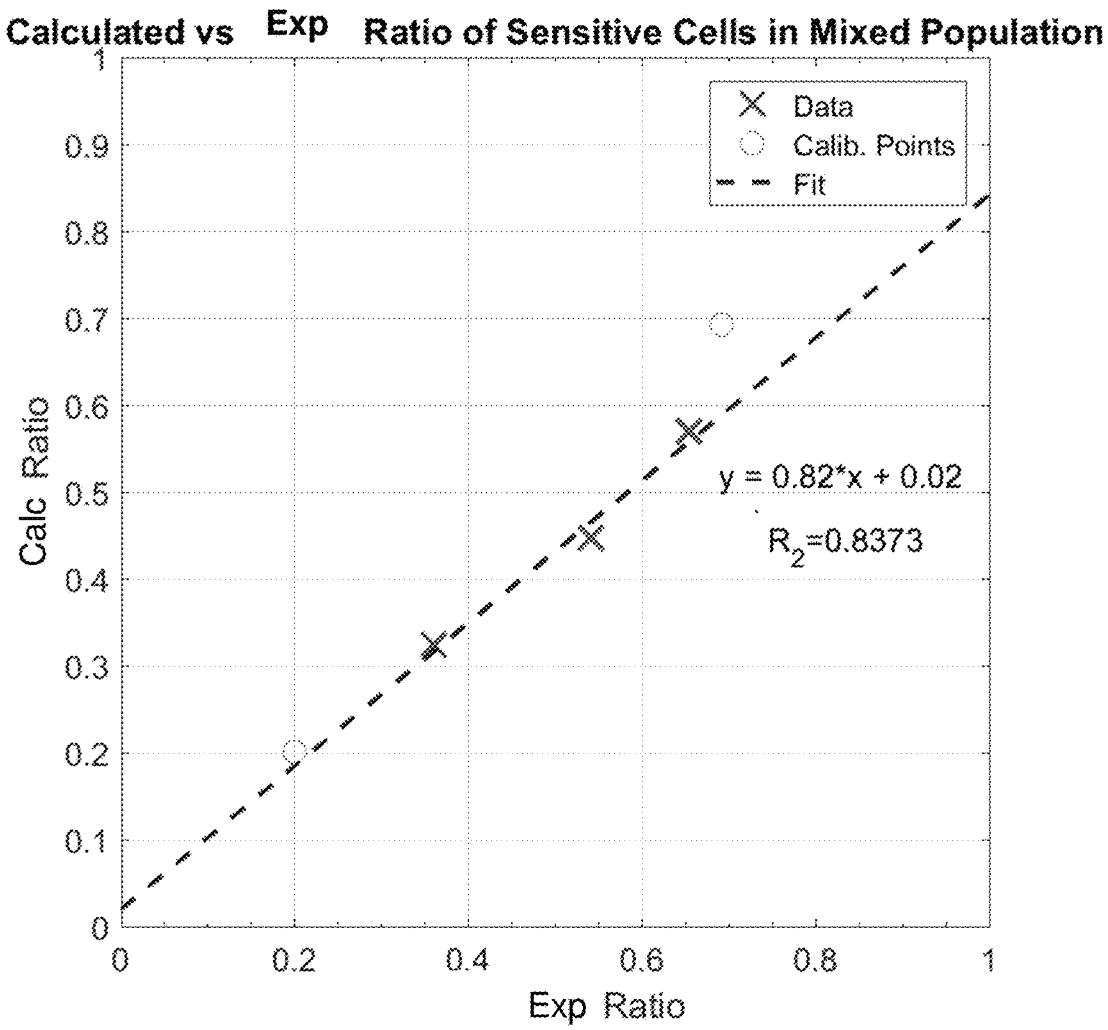

The experimental results were compared to the calculated results, which were in relatively good agreement. FIG. 27D shows a table of experimental and calculated sensitive mixing ratios. FIG. 27E shows a graphical representation of the experimental ratios and calculated ratios fitted with a linear model, which were found to be in reasonable agreement.

This example illustrates the types of analysis that may be performed to determine sensitive versus resistant populations in a patient. For example, in this example, different ratios of sensitive and resistant cells correspond to different growth rates, in between growth rates for a 100% resistant subpopulation and a 100% sensitive subpopulation. More complex models may be used to infer subpopulations for a particular patient.

In some aspects, the present techniques may be used to isolate different subpopulations of cells with different sensitivities, and the individual subpopulations may be assayed separately to determine optimal therapeutics for each subpopulation. Once the subpopulations are identified, the subpopulations may be optionally combined and tested with the optimal combination of therapeutics for each subpopulation. Example techniques for selecting and isolating desirable T lymphocytes by change in mass responses are described in U.S. Pat. No. 10,900,956, titled "Selecting and isolating desirable t lymphocytes by change in mass responses," which issued Jan. 26, 2021, and is incorporated herein by reference.

These techniques may be used to select an optimal drug for treatment of tumors with mixed populations of cells, which are sensitive to some therapeutics but not others. For example, models may be used to estimate the mix of sensitive and resistance cells, and may be used to select the optimal therapeutic(s) for eliminating both the sensitive and resistant cells. For example, if a therapeutic was shown to greatly impact growth rates of sensitive cells but not resistant cells, this therapeutic would not be selected. Instead, another therapeutic eliminating both populations of cells would be selected, even if the other therapeutic needs a longer period of time to eliminate the cancer cells.

Many different types of data analysis are contemplated herein, and all such types may be performed on a patient sample to determine sub-populations of cells.

Example 7. LCI for Media Development

Serum-free media has historically not been beneficial for growth or function of NK cells, such as NK-92, haNK, taNK, and aNK cells. As serum-based media such as FBS is derived from blood-based sources, it may be subject to contamination and/or infection with a variety of diseases. Additionally, serum-based media increases variability in cell culture (e.g., due to varying concentrations or components), making it difficult for researchers to precisely reproduce results. Accordingly, it is desirable to develop serum-free media for growth and culture of NK cells.

The present LCI techniques may be used to identify serum-free media, optionally in combination with one or more additives, suitable for growth of NK cells. In some aspects, NK cells may be placed in various types of serum-free media, which may additionally comprise one or more additives. LCI techniques may be used to assess changes in NK growth (e.g., haNK growth) as a function of time. In some aspects, a multi-well plate (e.g., a 48 well plate, a 96 well plate, etc.) may be used. In some aspects, each well in the multi-well plate may contain a different media. In other aspects and for statistical significance, groups of wells (e.g., two or more, three or more, four or more, five or more, six or more, etc.) may contain the same serum-free media. LCI techniques may be used to generate a growth curve for each well and the results for each well may be combined into a single growth curve to determine statistical significance.

In some aspects, the multi-well plates may be subjected to imaging under LCI for at least 8 hours, for at least 10 hours, for at least 12 hours, for at least 14 hours, for at least 16 hours or longer to differentiate haNK growth rates. Present techniques offer a substantial advantage as compared to traditional techniques, as such techniques employ rapid and quantitative measures for assessing NK cell growth using LCI in various media. Additionally, the present LCI techniques allow for screening a wide variety of medium conditions in a short timeframe, in some aspects, within 8 to 16 hours, or within about 8 to 12 hours. These techniques provide greatly accelerated experimental workflows with low volumes. In some aspects, 40 different medium compositions may be screened within hours.

In some aspects, serum-based media may be used as a control and may be analyzed concurrently with the serum-free media. For example, a well plate may include one or more wells with serum-based media and other wells with serum-free media. The serum-based and serum-free portions of the plate may be analyzed by LCI over an eight to a 12 hour timeframe (or longer), and the serum-free results may be compared to the serum-based (control results) to assess performance of the serum-free media as compared to accepted standard media.

Additives may include poly-D-lysine, etc. In other aspects, additives may include Pluronic F68, which is used to prevent or reduce NK cell clumping or adhesion.

In other aspects, LCI may be used to assess NK growth differences. Media with varying levels of serum may be tested to determine a minimum amount of serum to obtain a suitable growth rate.

Figure 28:
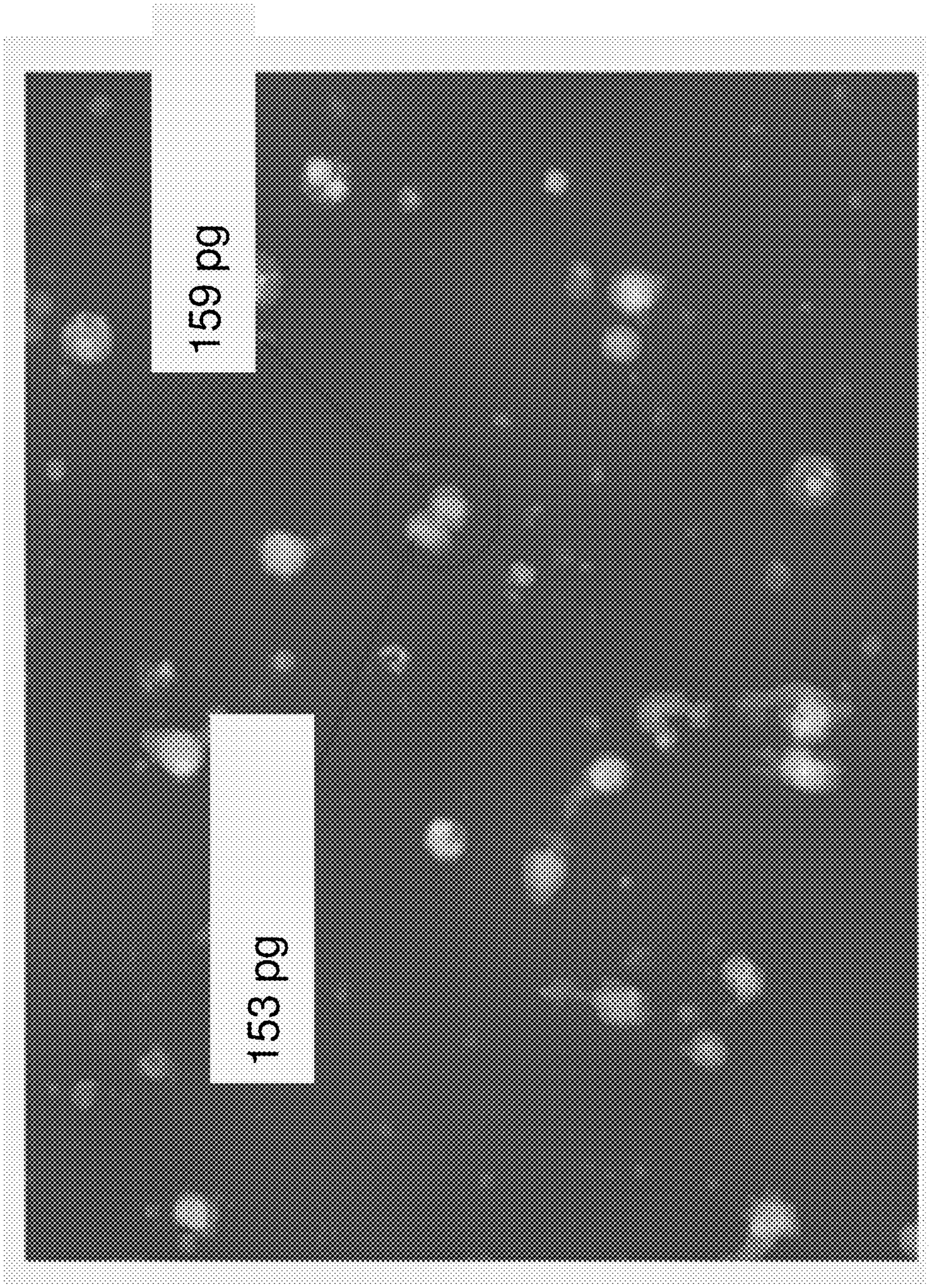
FIG. 28 shows NK cells imaged by live cell interferometry systems, according to aspects of the present disclosure.

FIG. 28 shows images of haNK cells which have recently undergone mitosis and LCI measures of initial mass.

Figure 29:
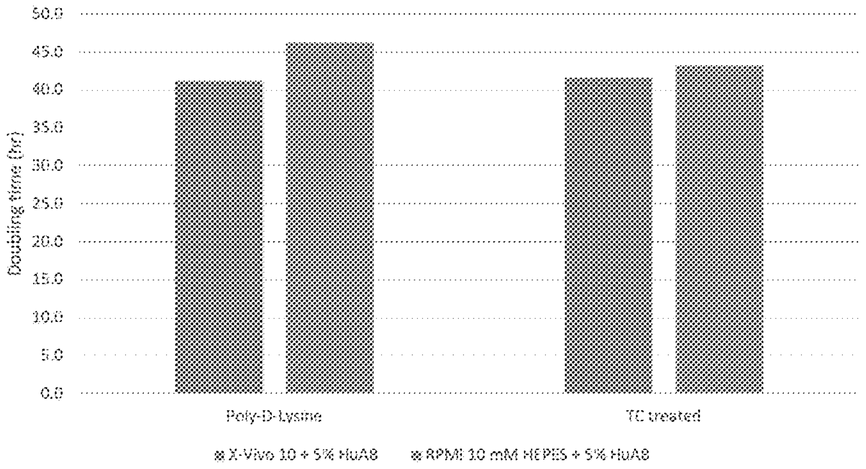
FIG. 29 shows growth of NK cells with and without poly-D-lysine, according to aspects of the present disclosure.
Figure 30:
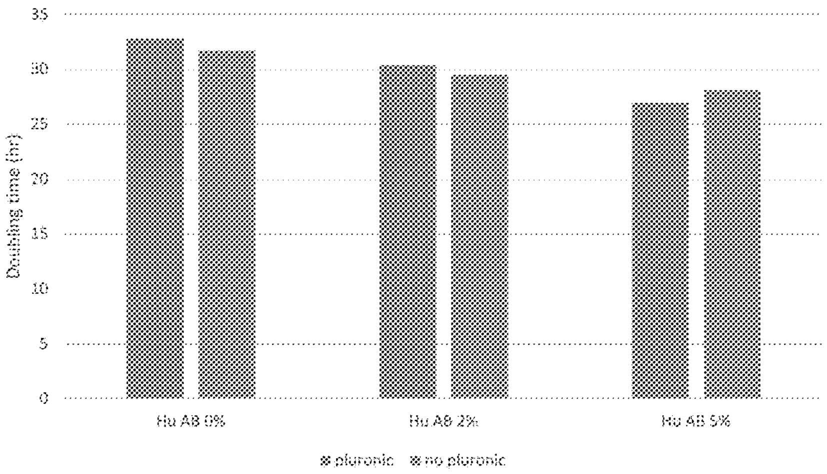
FIG. 30 shows growth of NK cells with and without Pluronic F68, according to aspects of the present disclosure.

FIGS. 29-30 show examples of assessing variations in media composition using LCI. Poly-D-lysine is commonly used on non-adherent cells to allow higher fidelity imaging using LCI. However, manufacturing conditions may not include poly-D-lysine, and therefore, assays were performed to determine the effect of poly-D-lysine on haNK growth.

FIG. 29 shows the results of LCI performed on haNK cells with and without poly-D-lysine, wherein the growth rate was determined to be similar between the two conditions. Using LCI, within 15 hours of plating the cells, growth rates were determined using standard TC-treated plates and plates coated with poly-D-lysine. The growth rates were found to be comparable. This type of assay may be extended to compare growth rate differences for any additive.

As shown in FIG. 30, a similar assay was performed using Pluronic F68. Cells were plated and monitored over a period of 15 hours for growth rates. Addition of Pluronic F68 was determined to have no measurable effect on growth rates for the range of serum conditions tested. In this experiment, serum titrations of 2% and 5% human AB serum (HuAB) showed a 7% and 18% decrease in doubling time, as compared to serum-free conditions (0% HuAB, no Pluronic acid). These conditions were monitored using LCI over 18-30 hours of cell growth. Without Pluronic acid, clumping of haNKs was prevalent and LCI results were skewed toward lower growth. With Pluronic acid, serum titrations of 2% and 5% Hu AB showed a 13% and 21% decrease in doubling time compared to serum-free conditions.

These experiments revealed that standard TC-treated plates are suitable for monitoring LCI media and that poly-d-lysine was not required. Additionally, Pluronic F68 was determined to have a minor effect on growth rates. In general, the highest-quality data was obtained using LCI images within 15 hours of plating the cells.

Figure 31A:
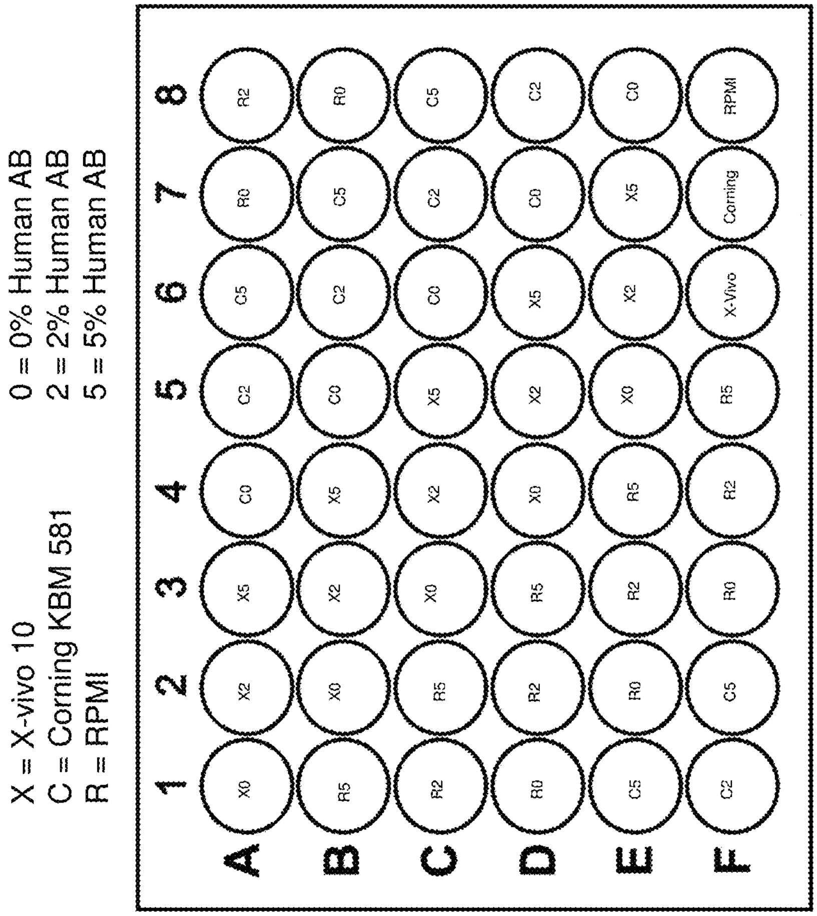
FIGS. 31A, 31B, 31C, 31D, 31E and 31F show assays involving growth of NK cells in various types of media, according to aspects of the present disclosure.

FIGS. 31A-31E show various aspects of using LCI to assess variations in media. FIG. 31A shows an example well configuration for assessing different types of media. In this setup, three types of media are compared (e.g., X-vivo 10 (X), RPMI (R), and Corning's KBM 581 serum free media (C)).

About 30,000 cells suspended in 200 μL of media were plated in each well. Cells were centrifuged at 300×g, for about 5 minutes, and LCI was performed immediately.

As shown in FIG. 31A, nine media conditions (5 repeats of each condition) were assayed using LCI. In a first set of experiments, wells were imaged for 15 hours, and 5 image positions per well were obtained for a total of 25 image positions per condition. About 500 useful tracks per condition or about 20 useful tracks per position were obtained. In a second set of experiments, wells were imaged for 20 hours, and about 6 image positions per well were obtained for a total of 30 image positions per condition. About 900 useful tracks per condition, or about 30 useful tracks per position were obtained.

Figure 31B:
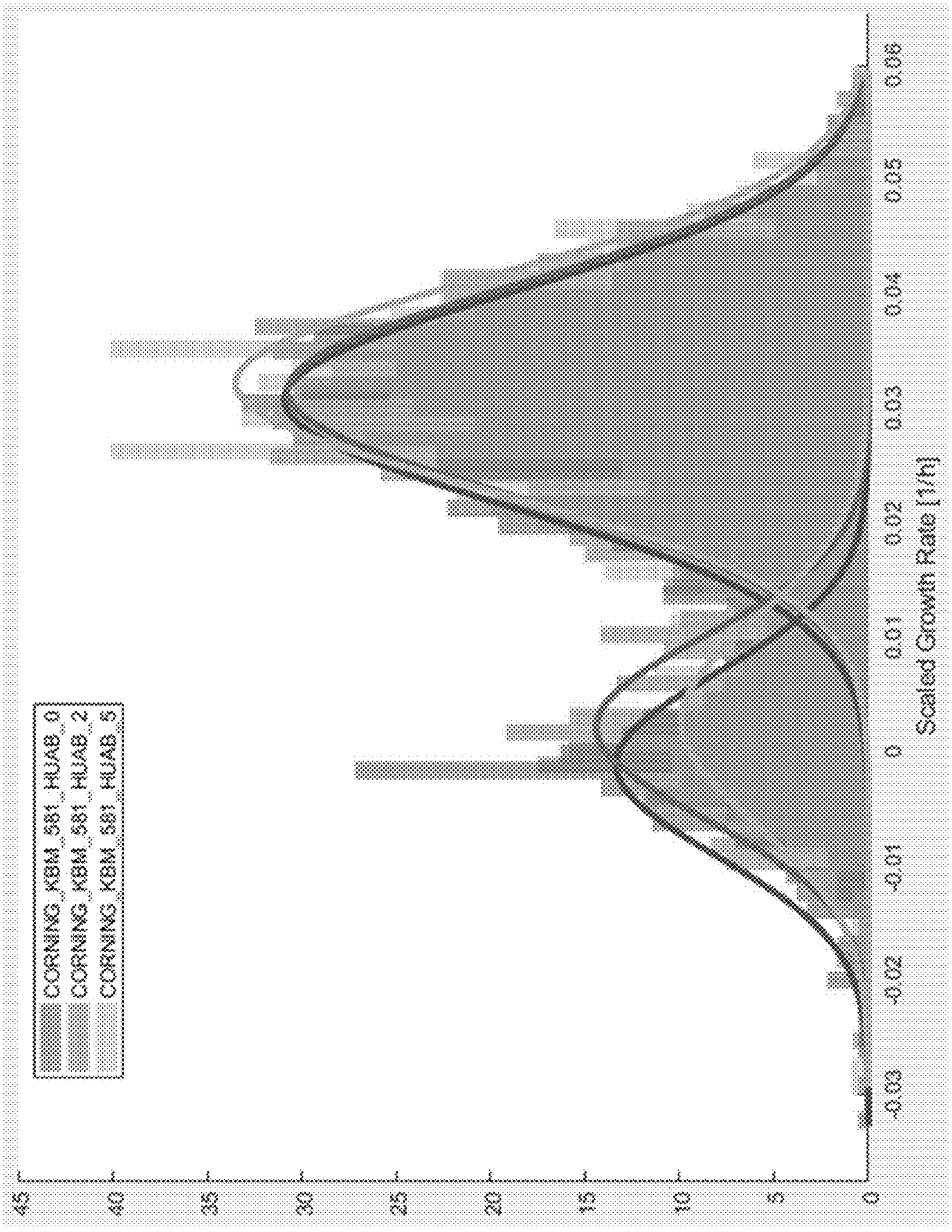

FIG. 31B shows a histogram of LCI results, which provides information on individual haNK cells from which global trends can be extracted. haNKs were separated into dual populations of stalled growth (bump on left of histogram) and healthy growing cells (large bump on right of histogram). Larger growth rates were observed at all titrations of serum.

Figure 31C:
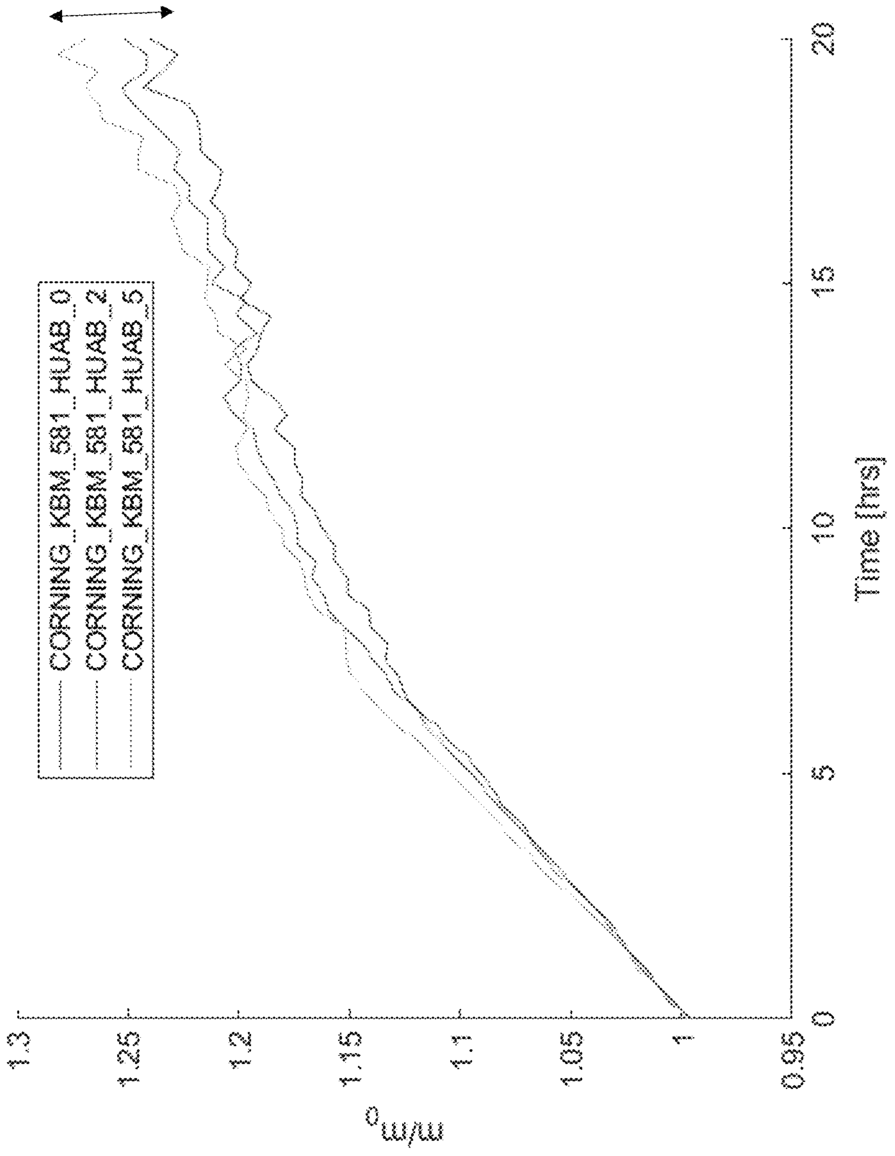
Figure 31D:
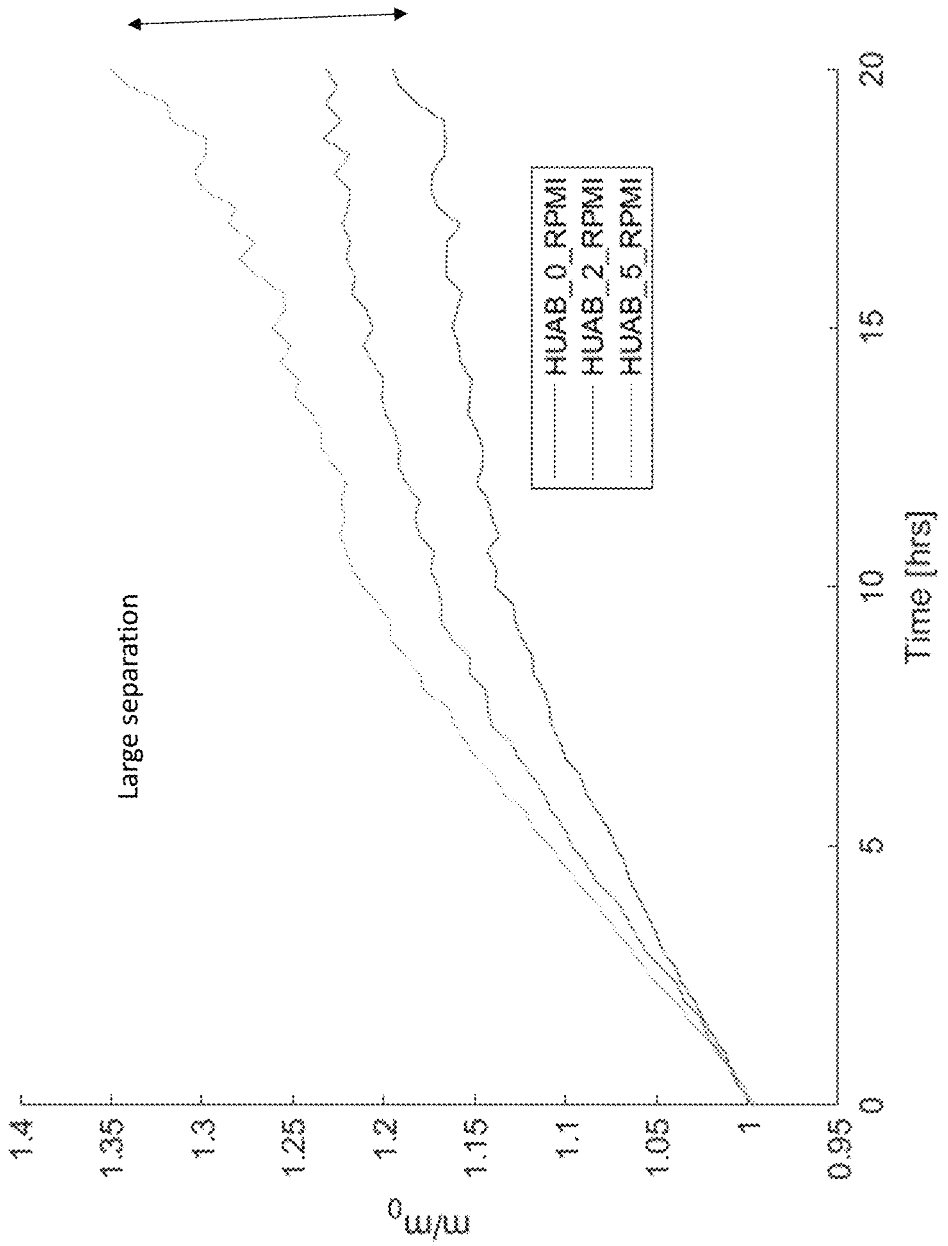
Figure 31E:
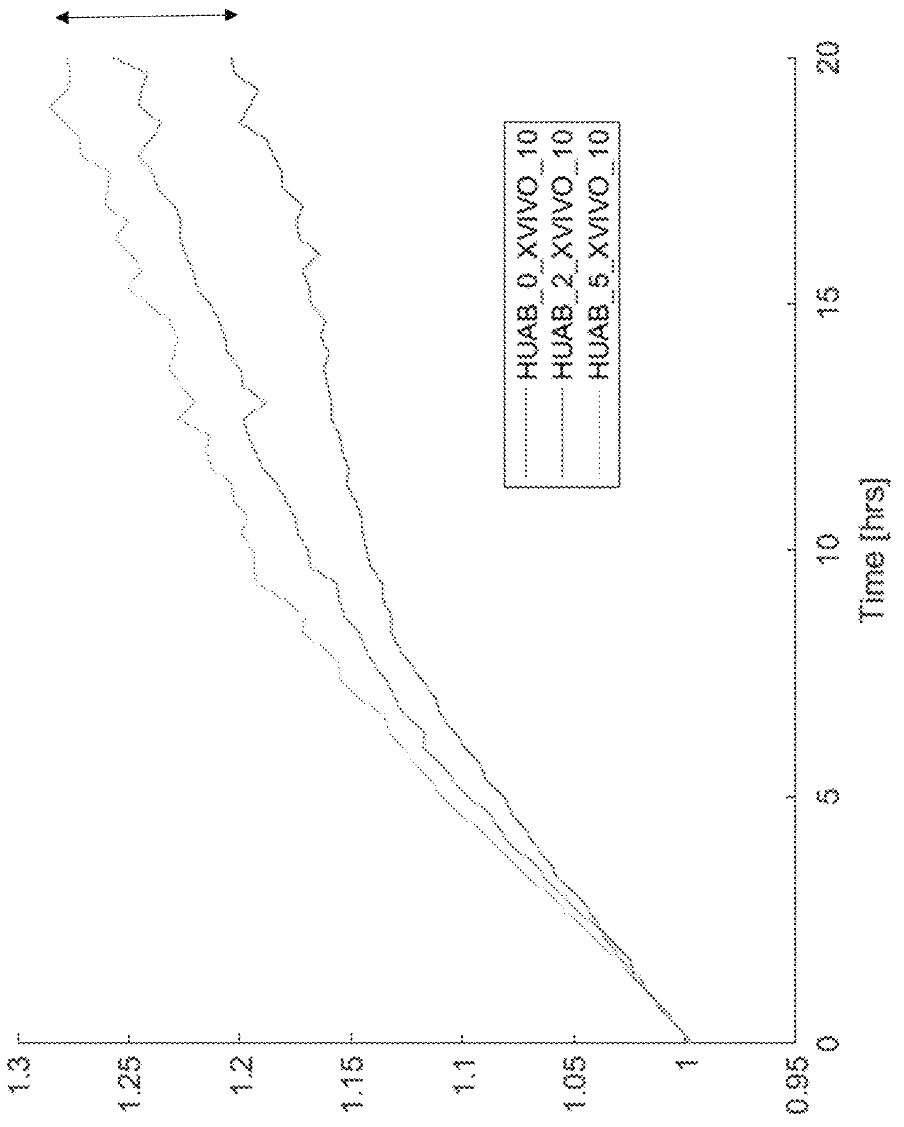

FIGS. 31C-31E show results of growth trajectories in different media. FIG. 31C corresponds to Corning KBM media in various concentrations of HuAB. FIG. 31D corresponds to RPMI media in various concentrations of HuAB. FIG. 31E corresponds to X vivo media in various concentrations of HuAB. In this experiment, the largest separation between the trials appeared in FIG. 31D.

X-vivo 10 with 5% Hu AB is the current standard in production. As shown in FIG. 31E, decreasing the amount of serum with X-vivo media worsened growth, although the results were not much worse when using 2% Hu AB. For RPMI media, significant variation was observed when using 2% Hu Ab, and both the 2% Hu Ab and 0% Hu Ab had reductions in growth rate. The RPMI media performed about as well as X-vivo 10 (the industry standard) at 5% Hu AB serum. The Corning media, under serum free and serum conditions outperformed on average the X-vivo 10 and RPMI media with less variation.

Figure 31F:
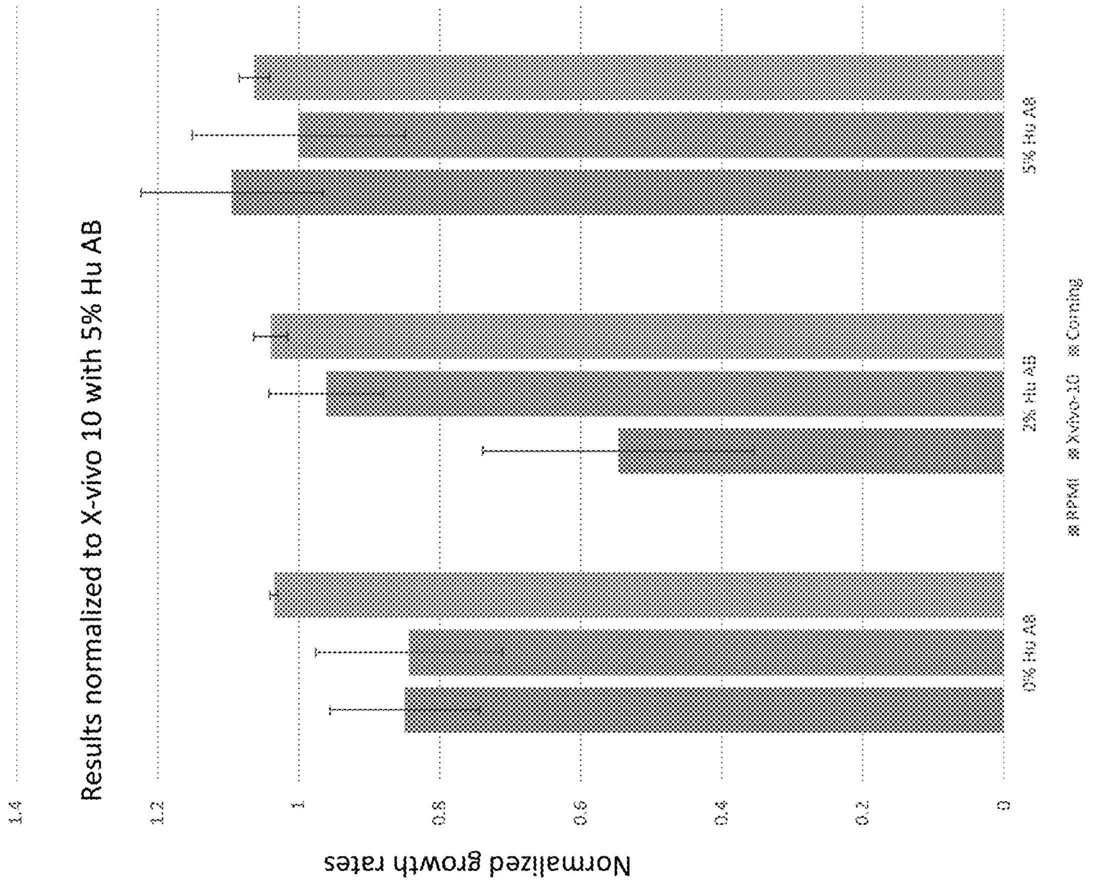

FIG. 31F summarizes the growth rates of cells in different media (e.g., RPMI, Xvivo-10 and Corning).

Example 7. Cell Mediated Elimination of Target Cells

LCI techniques may also be used to determine the ability of immune cells to eradicate cancer cells. For example, the ability of NK cells to eliminate cancer cells or for T-cells (CAR T cells) to eliminate cancer cells (by targeting an epitope on the cancer cell) may be assessed. This type of assay would allow screening of a drug, an antibody, and/or cell-mediated killing to inhibit and/or destroy cancer cells on a single plate to be performed within 24 hours. The average growth rate of target (stained) cells without effector cells may be compared to the growth rates of target cells with effector cells. Cells that are attacked and eliminated by effector cells may release contents (including fluorescent dyes or molecules) into the media, and therefore, the background fluorescence may also be evaluated as an indication of cell elimination rate.

Figure 32A:
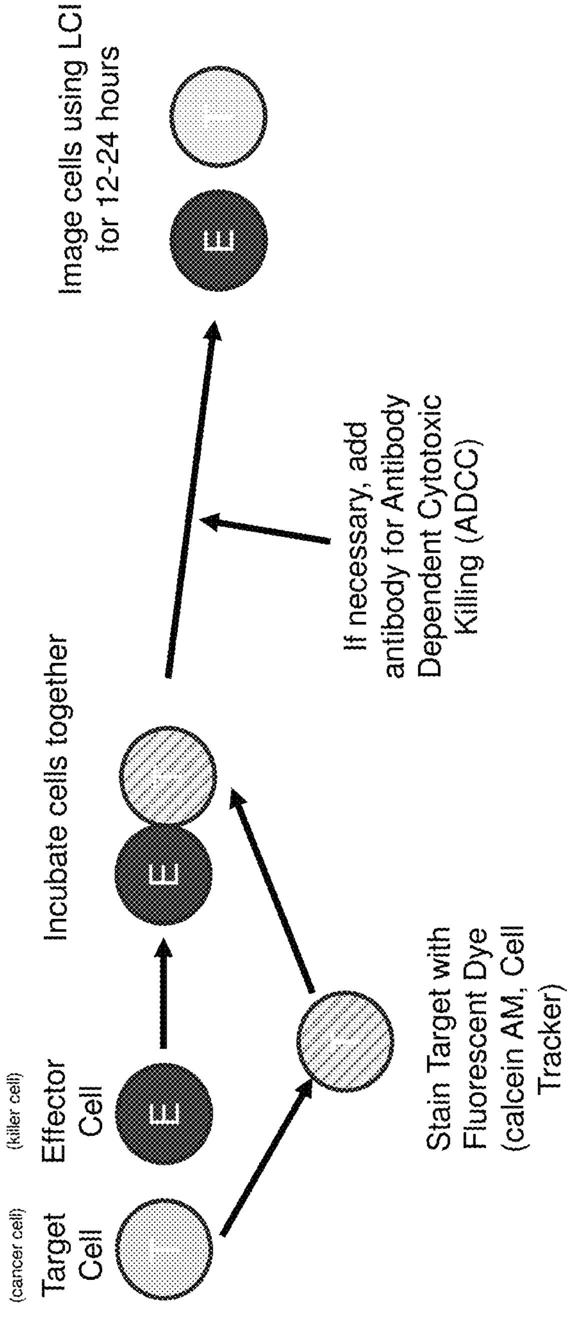
FIGS. 32A-32B show aspects of imaging target and effector cell interactions using interferometry based systems, according to aspects of the present disclosure.

FIG. 32A shows an example method of performing LCI on target cells and effector cells. For example, the target cell and the effector cell may be incubated together. In some cases, a stain specific for the target may be added (e.g., prior to incubation with the effector cell). The stain may be a fluorescent dye such as calcein AM, cell tracker, etc. In some cases, an antibody for ACDD may be added to the mix of effector cells and target cells.

This technique may also be used to identify heterologous cell populations. For example, if there are two populations of cancer cells obtained from the biological sample, and the effector cell or effector cell/ADCC antibody is only able to eliminate part of the cells, then the cells are heterologous. For example, the two populations of cells may be expressing different antigens on their respective cell surfaces and therefore, only one population will be targeted by an effector cell that recognizes a specific epitope on the target cell. Once appropriate incubation conditions have been established, the cells may be imaged using LCI every 12-24 hours.

Figure 32B:
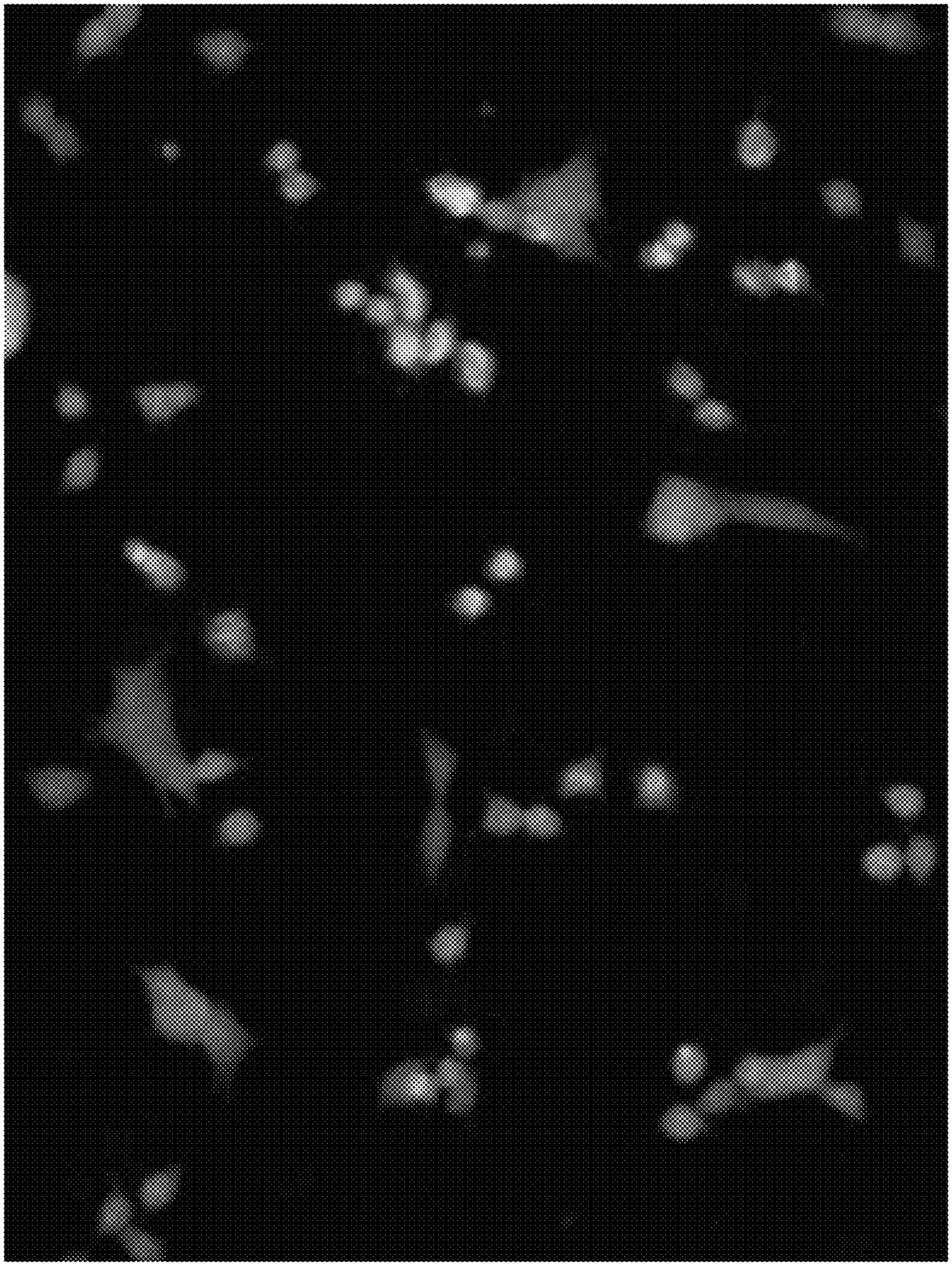

FIG. 32B shows EC.7 and dsRED cells mixed together in culture medium. dsRED cells were made from HEK293 cells stably transfected with dsRED protein. Tagging different cells with different markers allows analysis of separate populations and consideration of heterogeneous growth. Target versus killer cell and resistant versus sensitive cells may be analyzed.

Techniques for labeling cells are well known in the art and may include fluorescent dyes, incubation with fluorescent proteins, incorporation of genes encoding for fluorescent labels, etc. For cells that have multiple fluorescent labels, microscopic images may be taken using different channels and combined to generate a single image with multiple labels.

FIG. 32B shows a fluorescent image of cells comprising two different fluorescent markers. Thus, cells may be fluorescently tagged to differentiate between heterogeneous populations.

Figure 33:
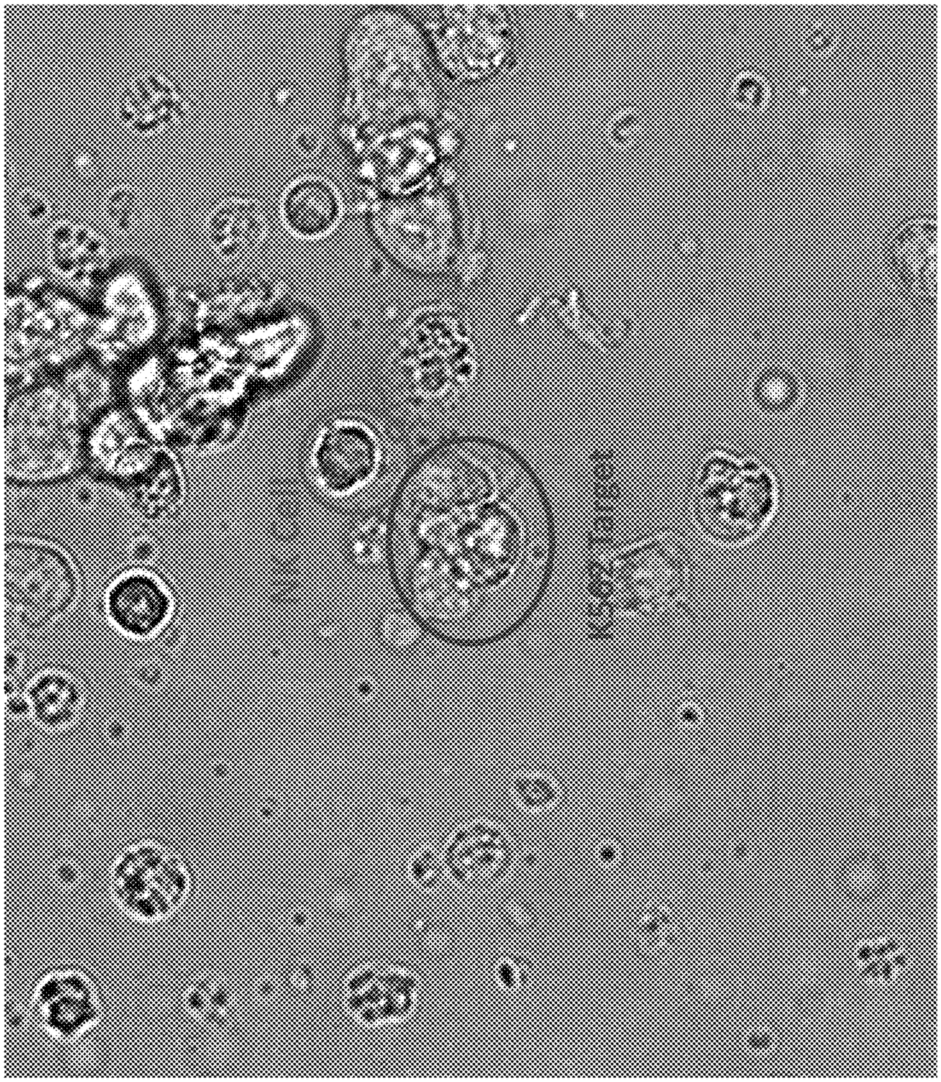
FIG. 33 shows an example of cell-cell interactions using interferometry based systems, according to embodiments of the present disclosure.

FIG. 33 shows an image of a NK cell targeting a K562 cell for destruction.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

It should be apparent to those skilled in the art that many more modifications besides those already described are possible without departing from the concepts provided herein. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. The examples presented herein are not intended to be limited with respect to a particular order of operations. Where the specification claims refers to at least one of something selected from the group consisting of A, B, C . . . and N, the text should be interpreted as requiring only one element from the group, not A plus N, or B plus N, etc.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. The phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer-implemented method of detecting mass changes of cells, wherein the cells are on a surface, the method comprising:

exposing a first group of cells to a control condition and a second group of cells to a non-control condition, wherein the non-control condition comprises a chemotherapeutic;

measuring masses of individual cells in the first group and in the second group using live cell interferometry (LCI) as a function of time;

identifying at least two subpopulations of cells using LCI, wherein a first one of the subpopulations is sensitive to the chemotherapeutic and a second one of the subpopulations is resistant to the chemotherapeutic;

determining an aggregate mass for the first group and an aggregate mass for the second group; and determining whether the aggregate mass of the second group has decreased relative to the aggregate mass of the first group for the time series.

2. The method of claim 1, wherein the cells are cancer cells and the non-control condition comprises a compound capable of inhibiting cancer growth.

3. The method of claim 1, further comprising determining whether the aggregate mass of the second group has decreased relative to the aggregate mass of the first group within four to twelve hours.

4. The method of claim 1, further comprising:

partitioning the second group of cells into a plurality of subgroups, and exposing each subgroup to a different non-control condition, each non-control condition comprising at least one therapeutic;

measuring masses of individual cells in the first group and in each subgroup in each image of the time series;

determining an aggregate mass for the first group and an aggregate mass for each subgroup; and determining whether the aggregate mass of each subgroup has decreased relative to the aggregate mass of the first group for the time series.

5. The method of claim 1, wherein the cells include at least one of H929 cells, MM.1 cells, patient-derived cells, multiple myeloma cancer cells, breast cancer cells, lung cancer cells, leukemia cells, and lymphoma cells.

6. The method of claim 1, wherein the non-control condition comprises at least one therapeutic, and the at least one therapeutic is a small molecule, a protein, an antibody or fragment thereof, a NK cell, or a CAR T cell.

7. The method of claim 1, wherein the non-control condition comprises immune cells and the second group of cells expresses a surface ligand to which the immune cells bind.

8. The method of claim 1, wherein the cells are immune cells and the non-control condition comprises a compound capable of activating the immune cells.

9. The method of claim 1, further comprising using machine learning to classify the cells into a first subpopulation of cells sensitive to a therapeutic and into a second population of cells resistant to a therapeutic.

10. The method of claim 1, further comprising using machine learning to identify immune cells that eliminate target cancer cells.

11. An imaging system for detecting mass changes of cells, wherein the cells are on a surface, the imaging system comprising at least one processor configured to:

expose a first group of cells to a control condition and a second group of cells to a non-control condition, wherein the non-control condition comprises a chemotherapeutic;

measure masses of individual cells in the first group and in the second group using live cell interferometry (LCI) as a function of time;

identify at least two subpopulations of cells using LCI, wherein a first one of the subpopulations is sensitive to the chemotherapeutic and a second one of the subpopulations is resistant to the chemotherapeutic;

determine an aggregate mass for the first group and an aggregate mass for the second group; and determine whether the aggregate mass of the second group has decreased relative to the aggregate mass of the first group for the time series.

12. The imaging system of claim 11, wherein the cells are cancer cells and the non-control condition comprises a compound capable of inhibiting cancer growth.

13. The imaging system of claim 11, wherein the at least one processor is configured to determine whether the aggregate mass of the second group has decreased relative to the aggregate mass of the first group within four to twelve hours.

14. The imaging system of claim 11, wherein the at least one processor is configured to:

partition the second group of cells into a plurality of subgroups, and expose each subgroup to a different non-control condition, each non-control condition comprising at least one therapeutic;

measure masses of individual cells in the first group and in each subgroup in each image of the time series;

determine an aggregate mass for the first group and an aggregate mass for each subgroup; and determine whether the aggregate mass of each subgroup has decreased relative to the aggregate mass of the first group for the time series.

15. The imaging system of claim 11, wherein the cells include at least one of H929 cells, MM.1 cells, patient-derived cells, multiple myeloma cancer cells, breast cancer cells, lung cancer cells, leukemia cells, and lymphoma cells.

16. The imaging system of claim 11, wherein the non-control condition comprises at least one therapeutic, and the at least one therapeutic is a small molecule, a protein, an antibody or fragment thereof, a NK cell, or a CAR T cell.

17. The imaging system of claim 11, wherein the non-control condition comprises immune cells and the second group of cells expresses a surface ligand to which the immune cells bind.

18. A computer program product for detecting mass changes of cells, wherein the cells are on a surface, the computer program product comprising a non-transitory computer readable storage medium having program instructions embodied therewith, the program instructions executable by a processor to cause the processor to:

expose a first group of cells to a control condition and a second group of cells to a non-control condition, wherein the non-control condition comprises a chemotherapeutic;

measure masses of individual cells in the first group and in the second group using live cell interferometry (LCI) as a function of time;

identify at least two subpopulations of cells using LCI, wherein a first one of the subpopulations is sensitive to the chemotherapeutic and a second one of the subpopulations is resistant to the chemotherapeutic;

determine an aggregate mass for the first group and an aggregate mass for the second group; and determine whether the aggregate mass of the second group has decreased relative to the aggregate mass of the first group for the time series.

19. A computer-implemented method of detecting mass changes of cells, wherein the cells are on a surface, the method comprising:

exposing a first group of cells to a control condition and a second group of cells to a non-control condition;

partitioning the second group of cells into a plurality of subgroups, and exposing each subgroup to a different non-control condition, each non-control condition comprising at least one therapeutic;

measuring masses of individual cells in the first group and in each of the plurality of subgroups of the second group using live cell interferometry (LCI) as a function of time, in each image of a timer series;

determining an aggregate mass for the first group and an aggregate mass for each of the plurality of subgroups of the second group; and determining whether the aggregate mass of each of the plurality of subgroups of the second group has decreased relative to the aggregate mass of the first group for the time series.

20. An imaging system for detecting mass changes of cells, wherein the cells are on a surface, the imaging system comprising at least one processor configured to:

expose a first group of cells to a control condition and a second group of cells to a non-control condition;

partition the second group of cells into a plurality of subgroups, and expose each subgroup to a different non-control condition, each non-control condition comprising at least one therapeutic;

measure masses of individual cells in the first group and in each of the plurality of subgroups of the second group using live cell interferometry (LCI) as a function of time, in each image of a timer series;

determine an aggregate mass for the first group and an aggregate mass for each of the plurality of subgroups of the second group; and determine whether the aggregate mass of each of the plurality of subgroups of the second group has decreased relative to the aggregate mass of the first group for the time series.

* * * * *